(12) United States Patent
Hayter et al.

(10) Patent No.: US 10,685,749 B2
(45) Date of Patent: Jun. 16, 2020

(54) INSULIN DELIVERY APPARATUSES CAPABLE OF BLUETOOTH DATA TRANSMISSION

(71) Applicant: ABBOTT DIABETES CARE INC., Alameda, CA (US)

(72) Inventors: Gary A. Hayter, Oakland, CA (US); Timothy C. Dunn, San Francisco, CA (US)

(73) Assignee: Abbott Diabetes Care Inc., Alameda, CA (US)

( * ) Notice: Subject to any disclaimer, the term of this patent is extended or adjusted under 35 U.S.C. 154(b) by 1113 days.

(21) Appl. No.: 14/981,863

(22) Filed: Dec. 28, 2015

(65) Prior Publication Data

US 2016/0106919 A1    Apr. 21, 2016

Related U.S. Application Data

(63) Continuation of application No. 12/242,799, filed on Sep. 30, 2008, now abandoned, which is a
(Continued)

(51) Int. Cl.
*G16H 50/50* (2018.01)
*H04W 4/80* (2018.01)
(Continued)

(52) U.S. Cl.
CPC .......... *G16H 50/50* (2018.01); *A61M 5/142* (2013.01); *A61M 5/1723* (2013.01);
(Continued)

(58) Field of Classification Search
CPC ............ A61B 5/14532; G06F 19/3418; G06F 19/3456; G06F 19/3437; G06F 19/325;
(Continued)

(56) References Cited

U.S. PATENT DOCUMENTS 3,581,062 A    5/1971 Aston
3,926,760 A    12/1975 Allen et al.
(Continued)

FOREIGN PATENT DOCUMENTS

EP    0098592    1/1984
EP    0127958    12/1984
(Continued)

OTHER PUBLICATIONS

WO, PCT/US2008/087857 ISR and Written Opinion, dated Mar. 20, 2009.
(Continued)

*Primary Examiner* — Joseph D Burgess
(74) *Attorney, Agent, or Firm* — Vorys, Sater, Seymour and Pease LLP

(57) ABSTRACT

Method and system including displaying a first representation of a medication treatment parameter profile, displaying a first representation of a physiological profile associated with the medication treatment parameter profile, detecting a modification to a segment of the medication treatment parameter profile, displaying a modified representation of the medication treatment parameter profile and the physiological profile based on the detected modification to the segment of the medication treatment parameter profile, modifying an attribute of the first representation of the medication treatment parameter profile, and modifying an attribute of the first representation of the physiological profile are provided.

20 Claims, 27 Drawing Sheets

Related U.S. Application Data continuation-in-part of application No. 12/024,082, filed on Jan. 31, 2008, now abandoned.

(60) Provisional application No. 61/015,185, filed on Dec. 19, 2007.

(51) Int. Cl.

| | | |
|---|---|---|
| *G06F 19/00* | (2018.01) | |
| *G06F 3/0484* | (2013.01) | |
| *G06Q 50/22* | (2018.01) | |
| *G06K 9/00* | (2006.01) | |
| *A61M 5/142* | (2006.01) | |
| *A61M 5/172* | (2006.01) | |
| *G16H 40/63* | (2018.01) | |

(52) U.S. Cl.
CPC ...... *G06F 3/04847* (2013.01); *G06F 19/3468* (2013.01); *G06K 9/0055* (2013.01); *G06Q 50/22* (2013.01); *G16H 40/63* (2018.01); *H04W 4/80* (2018.02); *A61M 2005/14208* (2013.01); *A61M 2205/18* (2013.01); *A61M 2205/3584* (2013.01); *A61M 2205/50* (2013.01); *A61M 2205/502* (2013.01); *A61M 2205/52* (2013.01); *A61M 2205/582* (2013.01); *A61M 2230/005* (2013.01); *A61M 2230/201* (2013.01)

(58) Field of Classification Search
CPC .... G06F 19/3468; G06Q 50/22; G16H 40/20; G16H 40/63; G16H 50/20; G16H 10/60; G16H 50/30; G16H 70/20; G16H 70/60
See application file for complete search history.

(56) References Cited

U.S. PATENT DOCUMENTS

| | | | |
|---|---|---|---|
| 3,949,388 A | 4/1976 | Fuller | |
| 3,960,497 A | 6/1976 | Acord et al. | |
| 3,978,856 A | 9/1976 | Michel | |
| 4,036,749 A | 7/1977 | Anderson | |
| 4,055,175 A | 10/1977 | Clemens et al. | |
| 4,129,128 A | 12/1978 | McFarlane | |
| 4,245,634 A | 1/1981 | Albisser et al. | |
| 4,327,725 A | 5/1982 | Cortese et al. | |
| 4,344,438 A | 8/1982 | Schultz | |
| 4,349,728 A | 9/1982 | Phillips et al. | |
| 4,373,527 A | 2/1983 | Fischell | |
| 4,392,849 A | 7/1983 | Petre et al. | |
| 4,425,920 A | 1/1984 | Bourland et al. | |
| 4,431,004 A | 2/1984 | Bessman et al. | |
| 4,441,968 A | 4/1984 | Emmer et al. | |
| 4,462,048 A | 7/1984 | Ross | |
| 4,464,170 A | 8/1984 | Clemens et al. | |
| 4,478,976 A | 10/1984 | Goertz et al. | |
| 4,494,950 A | 1/1985 | Fischell | |
| 4,509,531 A | 4/1985 | Ward | |
| 4,527,240 A | 7/1985 | Kvitash | |
| 4,538,616 A | 9/1985 | Rogoff | |
| 4,545,382 A | 10/1985 | Higgins et al. | |
| 4,619,793 A | 10/1986 | Lee | |
| 4,671,288 A | 6/1987 | Gough | |
| 4,703,756 A | 11/1987 | Gough et al. | |
| 4,711,245 A | 12/1987 | Higgins et al. | |
| 4,731,051 A | 3/1988 | Fischell | |
| 4,731,726 A | 3/1988 | Allen, III | |
| 4,749,985 A | 6/1988 | Corsberg | |
| 4,757,022 A | 7/1988 | Shults et al. | |
| 4,759,366 A | 7/1988 | Callaghan | |
| 4,777,953 A | 10/1988 | Ash et al. | |
| 4,779,618 A | 10/1988 | Mund et al. | |
| 4,847,785 A | 7/1989 | Stephens | |
| 4,854,322 A | 8/1989 | Ash et al. | |
| 4,871,351 A | 10/1989 | Feingold | |
| 4,890,620 A | 1/1990 | Gough | |
| 4,925,268 A | 5/1990 | Iyer et al. | |
| 4,947,845 A | 8/1990 | Davis | |
| 4,953,552 A | 9/1990 | DeMarzo | |
| 4,986,271 A | 1/1991 | Wilkins | |
| 4,995,402 A | 2/1991 | Smith et al. | |
| 5,000,180 A | 3/1991 | Kuypers et al. | |
| 5,002,054 A | 3/1991 | Ash et al. | |
| 5,019,974 A | 5/1991 | Beckers | |
| 5,050,612 A | 9/1991 | Matsumura | |
| 5,051,688 A | 9/1991 | Murase et al. | |
| 5,055,171 A | 10/1991 | Peck | |
| 5,068,536 A | 11/1991 | Rosenthal | |
| 5,077,476 A | 12/1991 | Rosenthal | |
| 5,082,550 A | 1/1992 | Rishpon et al. | |
| 5,106,365 A | 4/1992 | Hernandez | |
| 5,113,869 A | 5/1992 | Nappholz et al. | |
| 5,122,925 A | 6/1992 | Inpyn | |
| 5,135,004 A | 8/1992 | Adams et al. | |
| 5,148,812 A | 9/1992 | Verrier et al. | |
| 5,165,407 A | 11/1992 | Wilson et al. | |
| 5,202,261 A | 4/1993 | Musho et al. | |
| 5,203,326 A | 4/1993 | Collins | |
| 5,204,264 A | 4/1993 | Kaminer et al. | |
| 5,210,778 A | 5/1993 | Massart | |
| 5,228,449 A | 7/1993 | Christ et al. | |
| 5,199,428 A | 8/1993 | Obel et al. | |
| 5,231,988 A | 8/1993 | Wernicke et al. | |
| 5,246,867 A | 9/1993 | Lakowicz et al. | |
| 5,251,126 A | 10/1993 | Kahn et al. | |
| 5,262,035 A | 11/1993 | Gregg et al. | |
| 5,262,305 A | 11/1993 | Heller et al. | |
| 5,264,104 A | 11/1993 | Gregg et al. | |
| 5,264,105 A | 11/1993 | Gregg et al. | |
| 5,279,294 A | 1/1994 | Anderson et al. | |
| 5,284,425 A | 2/1994 | Holtermann et al. | |
| 5,285,792 A | 2/1994 | Sjoquist et al. | |
| 5,293,877 A | 3/1994 | O'Hara et al. | |
| 5,299,571 A | 4/1994 | Mastrototaro | |
| 5,312,762 A | 5/1994 | Guiseppi-Elie | |
| 5,313,953 A | 5/1994 | Yomtov et al. | |
| 5,320,715 A | 6/1994 | Berg | |
| 5,320,725 A | 6/1994 | Gregg et al. | |
| 5,322,063 A | 6/1994 | Allen et al. | |
| 5,328,460 A | 7/1994 | Lord et al. | |
| 5,330,634 A | 7/1994 | Wong et al. | |
| 5,340,722 A | 8/1994 | Wolfbeis et al. | |
| 5,342,789 A | 8/1994 | Chick et al. | |
| 5,356,786 A | 10/1994 | Heller et al. | |
| 5,360,404 A | 11/1994 | Novacek et al. | |
| 5,365,426 A | 11/1994 | Siegel et al. | |
| 5,372,427 A | 12/1994 | Padovani et al. | |
| 5,376,070 A | 12/1994 | Purvis et al. | |
| 5,379,238 A | 1/1995 | Stark | |
| 5,384,547 A | 1/1995 | Lynk et al. | |
| 5,390,671 A | 2/1995 | Lord et al. | |
| 5,391,250 A | 2/1995 | Cheney, II et al. | |
| 5,400,795 A | 3/1995 | Murphy et al. | |
| 5,408,999 A | 4/1995 | Singh et al. | |
| 5,410,326 A | 4/1995 | Goldstein | |
| 5,411,647 A | 5/1995 | Johnson et al. | |
| 5,425,749 A | 6/1995 | Adams | |
| 5,425,868 A | 6/1995 | Pedersen | |
| 5,429,602 A | 7/1995 | Hauser | |
| 5,431,160 A | 7/1995 | Wilkins | |
| 5,431,921 A | 7/1995 | Thombre | |
| 5,438,983 A | 8/1995 | Falcone | |
| 5,462,645 A | 10/1995 | Albery et al. | |
| 5,472,317 A | 12/1995 | Field et al. | |
| 5,489,414 A | 2/1996 | Schreiber et al. | |
| 5,497,772 A | 3/1996 | Schulman et al. | |
| 5,505,828 A | 4/1996 | Wong et al. | |
| 5,507,288 A | 4/1996 | Bocker et al. | |
| 5,509,410 A | 4/1996 | Hill et al. | |
| 5,514,718 A | 5/1996 | Lewis et al. | |
| 5,520,191 A | 5/1996 | Karlsson et al. | |
| 5,531,878 A | 7/1996 | Vadgama et al. | |
| 5,532,686 A | 7/1996 | Urbas et al. | |

(56) References Cited

U.S. PATENT DOCUMENTS

| | | |
|---|---|---|
| 5,543,326 A | 8/1996 | Heller et al. |
| 5,552,997 A | 9/1996 | Massart |
| 5,568,400 A | 10/1996 | Stark et al. |
| 5,568,806 A | 10/1996 | Cheney, II et al. |
| 5,569,186 A | 10/1996 | Lord et al. |
| 5,582,184 A | 12/1996 | Erickson et al. |
| 5,586,553 A | 12/1996 | Halili et al. |
| 5,593,852 A | 1/1997 | Heller et al. |
| 5,601,435 A | 2/1997 | Quy |
| 5,609,575 A | 3/1997 | Larson et al. |
| 5,619,631 A | 4/1997 | Schott |
| 5,628,310 A | 5/1997 | Rao et al. |
| 5,628,324 A | 5/1997 | Sarbach |
| 5,628,890 A | 5/1997 | Nigel et al. |
| 5,634,468 A | 6/1997 | Platt et al. |
| 5,640,954 A | 6/1997 | Pfeiffer et al. |
| 5,653,239 A | 8/1997 | Pompei et al. |
| 5,660,163 A | 8/1997 | Schulman et al. |
| 5,665,222 A | 9/1997 | Heller et al. |
| 5,707,502 A | 1/1998 | McCaffrey et al. |
| 5,711,001 A | 1/1998 | Bussan et al. |
| 5,711,861 A | 1/1998 | Ward et al. |
| 5,720,295 A | 2/1998 | Greenhut et al. |
| 5,724,030 A | 3/1998 | Urbas et al. |
| 5,726,646 A | 3/1998 | Bane et al. |
| 5,733,259 A | 3/1998 | Valcke et al. |
| 5,735,285 A | 4/1998 | Albert et al. |
| 5,738,220 A | 4/1998 | Geszler |
| 5,741,211 A | 4/1998 | Renirie et al. |
| 5,748,103 A | 5/1998 | Flach et al. |
| 5,749,907 A | 5/1998 | Mann |
| 5,771,891 A | 6/1998 | Gozani |
| 5,772,586 A | 6/1998 | Heinonen et al. |
| 5,785,660 A | 7/1998 | van Lake et al. |
| 5,791,344 A | 8/1998 | Schulman et al. |
| 5,792,065 A | 8/1998 | Xue et al. |
| 5,804,047 A | 9/1998 | Karube et al. |
| 5,820,551 A | 10/1998 | Hills et al. |
| 5,822,715 A | 10/1998 | Worthington et al. |
| 5,833,603 A | 11/1998 | Kovacs et al. |
| 5,842,189 A | 11/1998 | Keeler et al. |
| 5,891,047 A | 4/1999 | Lander et al. |
| 5,891,049 A | 4/1999 | Cyrus et al. |
| 5,899,855 A | 5/1999 | Brown |
| 5,914,026 A | 6/1999 | Blubaugh, Jr. et al. |
| 5,918,603 A | 7/1999 | Brown |
| 5,925,021 A | 7/1999 | Castellano et al. |
| 5,935,224 A | 8/1999 | Svancarek et al. |
| 5,942,979 A | 8/1999 | Luppino |
| 5,951,485 A | 9/1999 | Cyrus et al. |
| 5,957,854 A | 9/1999 | Besson et al. |
| 5,960,797 A | 10/1999 | Kramer et al. |
| 5,961,451 A | 10/1999 | Reber et al. |
| 5,964,993 A | 10/1999 | Blubaugh, Jr. et al. |
| 5,965,380 A | 10/1999 | Heller et al. |
| 5,971,922 A | 10/1999 | Arita et al. |
| 5,972,199 A | 10/1999 | Heller et al. |
| 5,980,708 A | 11/1999 | Champagne et al. |
| 5,995,860 A | 11/1999 | Sun et al. |
| 6,001,067 A | 12/1999 | Shults et al. |
| 6,016,443 A | 1/2000 | Ekwall et al. |
| 6,021,350 A | 2/2000 | Mathson |
| 6,024,699 A | 2/2000 | Surwit et al. |
| 6,028,413 A | 2/2000 | Brockmann |
| 6,038,469 A | 3/2000 | Karlsson et al. |
| 6,049,727 A | 4/2000 | Crothall |
| 6,052,565 A | 4/2000 | Ishikura et al. |
| 6,066,243 A | 5/2000 | Anderson et al. |
| 6,071,391 A | 6/2000 | Gotoh et al. |
| 6,073,031 A | 6/2000 | Helstab et al. |
| 6,083,710 A | 7/2000 | Heller et al. |
| 6,088,608 A | 7/2000 | Schulman et al. |
| 6,091,976 A | 7/2000 | Pfeiffer et al. |
| 6,091,987 A | 7/2000 | Thompson |
| 6,093,172 A | 7/2000 | Funderburk et al. |
| 6,096,364 A | 8/2000 | Bok et al. |
| 6,103,033 A | 8/2000 | Say et al. |
| 6,108,577 A | 8/2000 | Benser |
| 6,112,116 A | 8/2000 | Fischell |
| 6,117,290 A | 9/2000 | Say et al. |
| 6,119,028 A | 9/2000 | Schulman et al. |
| 6,120,676 A | 9/2000 | Heller et al. |
| 6,121,009 A | 9/2000 | Heller et al. |
| 6,121,611 A | 9/2000 | Lindsay et al. |
| 6,122,351 A | 9/2000 | Schlueter, Jr. et al. |
| 6,128,526 A | 10/2000 | Stadler et al. |
| 6,130,623 A | 10/2000 | MacLellan et al. |
| 6,134,461 A | 10/2000 | Say et al. |
| 6,115,628 A | 11/2000 | Stadler et al. |
| 6,143,164 A | 11/2000 | Heller et al. |
| 6,144,837 A | 11/2000 | Quy |
| 6,144,871 A | 11/2000 | Saito et al. |
| 6,159,147 A | 12/2000 | Lichter et al. |
| 6,161,095 A | 12/2000 | Brown |
| 6,162,611 A | 12/2000 | Heller et al. |
| 6,175,752 B1 | 1/2001 | Say et al. |
| 6,200,265 B1 | 3/2001 | Walsh et al. |
| 6,212,416 B1 | 4/2001 | Ward et al. |
| 6,219,574 B1 | 4/2001 | Cormier et al. |
| 6,233,471 B1 | 5/2001 | Berner et al. |
| 6,233,486 B1 | 5/2001 | Ekwall et al. |
| 6,248,067 B1 | 6/2001 | Causey, III et al. |
| 6,249,705 B1 | 6/2001 | Snell |
| 6,254,586 B1 | 7/2001 | Mann et al. |
| 6,256,538 B1 | 7/2001 | Ekwall |
| 6,264,606 B1 | 7/2001 | Ekwall et al. |
| 6,270,455 B1 | 8/2001 | Brown |
| 6,272,379 B1 | 8/2001 | Fischell et al. |
| 6,275,717 B1 | 8/2001 | Gross et al. |
| 6,283,761 B1 | 9/2001 | Joao |
| 6,284,478 B1 | 9/2001 | Heller et al. |
| 6,291,200 B1 | 9/2001 | LeJeune et al. |
| 6,293,925 B1 | 9/2001 | Safabash et al. |
| 6,294,997 B1 | 9/2001 | Paratore et al. |
| 6,295,506 B1 | 9/2001 | Heinonen et al. |
| 6,296,571 B1 | 10/2001 | McVicar |
| 6,299,347 B1 | 10/2001 | Pompei |
| 6,299,757 B1 | 10/2001 | Feldman et al. |
| 6,306,104 B1 | 10/2001 | Cunningham et al. |
| 6,309,884 B1 | 10/2001 | Cooper et al. |
| 6,314,317 B1 | 11/2001 | Willis |
| 6,329,161 B1 | 12/2001 | Heller et al. |
| 6,338,790 B1 | 1/2002 | Feldman et al. |
| 6,348,640 B1 | 2/2002 | Navot et al. |
| 6,359,270 B1 | 3/2002 | Bridson |
| 6,359,444 B1 | 3/2002 | Grimes |
| 6,360,888 B1 | 3/2002 | McIvor et al. |
| 6,361,503 B1 | 3/2002 | Starobin et al. |
| 6,366,794 B1 | 4/2002 | Moussy et al. |
| 6,377,828 B1 | 4/2002 | Chaiken et al. |
| 6,377,852 B1 | 4/2002 | Bornzin et al. |
| 6,377,894 B1 | 4/2002 | Deweese et al. |
| 6,379,301 B1 | 4/2002 | Worthington et al. |
| 6,381,493 B1 | 4/2002 | Stadler et al. |
| 6,387,048 B1 | 5/2002 | Schulman et al. |
| 6,400,974 B1 | 6/2002 | Lesho |
| 6,405,066 B1 | 6/2002 | Essenpreis et al. |
| 6,413,393 B1 | 7/2002 | Van Antwerp et al. |
| 6,416,471 B1 | 7/2002 | Kumar et al. |
| 6,418,346 B1 | 7/2002 | Nelson et al. |
| 6,424,847 B1 | 7/2002 | Mastrototaro et al. |
| 6,427,088 B1 | 7/2002 | Bowman, IV et al. |
| 6,440,068 B1 | 8/2002 | Brown et al. |
| 6,461,496 B1 | 10/2002 | Feldman et al. |
| 6,471,689 B1 | 10/2002 | Joseph et al. |
| 6,478,736 B1 | 11/2002 | Mault |
| 6,484,046 B1 | 11/2002 | Say et al. |
| 6,493,069 B1 | 12/2002 | Nagashimada et al. |
| 6,496,729 B2 | 12/2002 | Thompson |
| 6,497,655 B1 | 12/2002 | Linberg et al. |
| 6,498,043 B1 | 12/2002 | Schulman et al. |
| 6,501,983 B1 | 12/2002 | Natarajan et al. |
| 6,503,381 B1 | 1/2003 | Gotoh et al. |
| 6,514,460 B1 | 2/2003 | Fendrock |

(56) References Cited

U.S. PATENT DOCUMENTS

| | | |
|---|---|---|
| 6,514,718 B2 | 2/2003 | Heller et al. |
| 6,520,326 B2 | 2/2003 | McIvor et al. |
| 6,540,891 B1 | 4/2003 | Stewart et al. |
| 6,544,212 B2 | 4/2003 | Galley et al. |
| 6,546,268 B1 | 4/2003 | Ishikawa et al. |
| 6,549,796 B2 | 4/2003 | Sohrab |
| 6,551,494 B1 | 4/2003 | Heller et al. |
| 6,554,798 B1 | 4/2003 | Mann et al. |
| 6,558,320 B1 | 5/2003 | Causey, III et al. |
| 6,558,321 B1 | 5/2003 | Burd et al. |
| 6,558,351 B1 | 5/2003 | Steil et al. |
| 6,560,471 B1 | 5/2003 | Heller et al. |
| 6,561,975 B1 | 5/2003 | Pool et al. |
| 6,561,978 B1 | 5/2003 | Conn et al. |
| 6,562,001 B2 | 5/2003 | Lebel et al. |
| 6,564,105 B2 | 5/2003 | Starkweather et al. |
| 6,565,509 B1 | 5/2003 | Say et al. |
| 6,571,128 B2 | 5/2003 | Lebel et al. |
| 6,572,542 B1 | 6/2003 | Houben et al. |
| 6,572,545 B2 | 6/2003 | Knobbe et al. |
| 6,574,490 B2 | 6/2003 | Abbink et al. |
| 6,574,510 B2 | 6/2003 | Von Arx et al. |
| 6,576,101 B1 | 6/2003 | Heller et al. |
| 6,577,899 B2 | 6/2003 | Lebel et al. |
| 6,579,231 B1 | 6/2003 | Phipps |
| 6,579,690 B1 | 6/2003 | Bonnecaze et al. |
| 6,585,644 B2 | 7/2003 | Lebel et al. |
| 6,591,125 B1 | 7/2003 | Buse et al. |
| 6,592,745 B1 | 7/2003 | Feldman et al. |
| 6,595,919 B2 | 7/2003 | Berner et al. |
| 6,600,997 B2 | 7/2003 | Deweese et al. |
| 6,605,200 B1 | 8/2003 | Mao et al. |
| 6,605,201 B1 | 8/2003 | Mao et al. |
| 6,607,509 B2 | 8/2003 | Bobroff et al. |
| 6,610,012 B2 | 8/2003 | Mault |
| 6,616,819 B1 | 9/2003 | Liamos et al. |
| 6,618,934 B1 | 9/2003 | Feldman et al. |
| 6,622,045 B2 | 9/2003 | Snell et al. |
| 6,633,772 B2 | 10/2003 | Ford et al. |
| 6,635,014 B2 | 10/2003 | Starkweather et al. |
| 6,635,167 B1 | 10/2003 | Batman et al. |
| 6,641,533 B2 | 11/2003 | Causey, III et al. |
| 6,648,821 B2 | 11/2003 | Lebel et al. |
| 6,650,471 B2 | 11/2003 | Doi |
| 6,654,625 B1 | 11/2003 | Say et al. |
| 6,656,114 B1 | 12/2003 | Poulson et al. |
| 6,658,396 B1 | 12/2003 | Tang et al. |
| 6,659,948 B2 | 12/2003 | Lebel et al. |
| 6,668,196 B1 | 12/2003 | Villegas et al. |
| 6,675,030 B2 | 1/2004 | Ciuczak et al. |
| 6,676,816 B2 | 1/2004 | Mao et al. |
| 6,687,546 B2 | 2/2004 | Lebel et al. |
| 6,689,056 B1 | 2/2004 | Kilcoyne et al. |
| 6,694,191 B2 | 2/2004 | Starkweather et al. |
| 6,695,860 B1 | 2/2004 | Ward et al. |
| 6,698,269 B2 | 3/2004 | Baber et al. |
| 6,702,857 B2 | 3/2004 | Brauker et al. |
| 6,730,200 B1 | 5/2004 | Stewart et al. |
| 6,731,976 B2 | 5/2004 | Penn et al. |
| 6,731,985 B2 | 5/2004 | Poore et al. |
| 6,733,446 B2 | 5/2004 | Lebel et al. |
| 6,735,183 B2 | 5/2004 | O'Toole et al. |
| 6,736,957 B1 | 5/2004 | Forrow et al. |
| 6,740,072 B2 * | 5/2004 | Starkweather .... A61M 5/14276 604/504 |
| 6,740,075 B2 | 5/2004 | Lebel et al. |
| 6,740,518 B1 | 5/2004 | Duong et al. |
| 6,741,877 B1 | 5/2004 | Shults et al. |
| 6,746,582 B2 | 6/2004 | Heller et al. |
| 6,749,740 B2 | 6/2004 | Liamos et al. |
| 6,758,810 B2 | 7/2004 | Lebel et al. |
| 6,764,581 B1 | 7/2004 | Forrow et al. |
| 6,770,030 B1 | 8/2004 | Schaupp et al. |
| 6,773,671 B1 | 8/2004 | Lewis et al. |
| 6,789,195 B1 | 9/2004 | Prihoda et al. |
| 6,790,178 B1 | 9/2004 | Mault et al. |
| 6,804,558 B2 | 10/2004 | Haller et al. |
| 6,809,653 B1 | 10/2004 | Mann et al. |
| 6,810,290 B2 | 10/2004 | Lebel et al. |
| 6,811,533 B2 | 11/2004 | Lebel et al. |
| 6,811,534 B2 | 11/2004 | Bowman, IV et al. |
| 6,813,519 B2 | 11/2004 | Lebel et al. |
| 6,850,790 B2 | 2/2005 | Berner et al. |
| 6,862,465 B2 | 3/2005 | Shults et al. |
| 6,865,407 B2 | 3/2005 | Kimball et al. |
| 6,873,268 B2 | 3/2005 | Lebel et al. |
| 6,878,112 B2 | 4/2005 | Linberg et al. |
| 6,881,551 B2 | 4/2005 | Heller et al. |
| 6,882,940 B2 | 4/2005 | Potts et al. |
| 6,892,085 B2 | 5/2005 | McIvor et al. |
| 6,893,545 B2 | 5/2005 | Gotoh et al. |
| 6,895,263 B2 | 5/2005 | Shin et al. |
| 6,895,265 B2 | 5/2005 | Silver |
| 6,923,763 B1 | 8/2005 | Kovatchev et al. |
| 6,923,764 B2 | 8/2005 | Aceti et al. |
| 6,931,327 B2 | 8/2005 | Goode, Jr. et al. |
| 6,932,892 B2 | 8/2005 | Chen et al. |
| 6,932,894 B2 | 8/2005 | Mao et al. |
| 6,936,006 B2 | 8/2005 | Sabra |
| 6,940,403 B2 | 9/2005 | Kail, IV |
| 6,941,163 B2 | 9/2005 | Ford et al. |
| 6,942,518 B2 | 9/2005 | Liamos et al. |
| 6,950,708 B2 | 9/2005 | Bowman, IV et al. |
| 6,958,705 B2 | 10/2005 | Lebel et al. |
| 6,968,294 B2 | 11/2005 | Gutta et al. |
| 6,971,274 B2 | 12/2005 | Olin |
| 6,974,437 B2 | 12/2005 | Lebel et al. |
| 6,978,286 B2 | 12/2005 | Francis et al. |
| 6,983,176 B2 | 1/2006 | Gardner et al. |
| 6,990,366 B2 | 1/2006 | Say et al. |
| 6,997,907 B2 | 2/2006 | Safabash et al. |
| 6,998,247 B2 | 2/2006 | Monfre et al. |
| 7,003,336 B2 | 2/2006 | Holker et al. |
| 7,003,340 B2 | 2/2006 | Say et al. |
| 7,003,341 B2 | 2/2006 | Say et al. |
| 7,009,511 B2 | 3/2006 | Mazar et al. |
| 7,010,345 B2 | 3/2006 | Hill et al. |
| 7,015,817 B2 | 3/2006 | Copley et al. |
| 7,016,713 B2 | 3/2006 | Gardner et al. |
| 7,016,720 B2 | 3/2006 | Kroll |
| 7,020,508 B2 | 3/2006 | Stivoric et al. |
| 7,022,072 B2 | 4/2006 | Fox et al. |
| 7,022,219 B2 | 4/2006 | Mansouri et al. |
| 7,024,236 B2 | 4/2006 | Ford et al. |
| 7,024,245 B2 | 4/2006 | Lebel et al. |
| 7,025,425 B2 | 4/2006 | Kovatchev et al. |
| 7,027,848 B2 | 4/2006 | Robinson et al. |
| 7,027,931 B1 | 4/2006 | Jones et al. |
| 7,029,443 B2 | 4/2006 | Kroll |
| 7,029,444 B2 | 4/2006 | Shin et al. |
| 7,041,068 B2 | 5/2006 | Freeman et al. |
| 7,041,468 B2 | 5/2006 | Drucker et al. |
| 7,043,287 B1 | 5/2006 | Khalil et al. |
| 7,043,305 B2 | 5/2006 | KenKnight et al. |
| 7,046,153 B2 | 5/2006 | Oja et al. |
| 7,052,483 B2 | 5/2006 | Wojcik |
| 7,056,302 B2 | 6/2006 | Douglas |
| 7,058,453 B2 | 6/2006 | Nelson et al. |
| 7,060,031 B2 | 6/2006 | Webb et al. |
| 7,074,307 B2 | 7/2006 | Simpson et al. |
| 7,076,300 B1 | 7/2006 | Kroll et al. |
| 7,081,195 B2 | 7/2006 | Simpson et al. |
| 7,082,334 B2 | 7/2006 | Boute et al. |
| 7,092,891 B2 | 8/2006 | Maus et al. |
| 7,096,064 B2 | 8/2006 | Deno et al. |
| 7,098,803 B2 | 8/2006 | Mann et al. |
| 7,103,412 B1 | 9/2006 | Kroll |
| 7,108,778 B2 | 9/2006 | Simpson et al. |
| 7,110,803 B2 | 9/2006 | Shults et al. |
| 7,113,821 B1 | 9/2006 | Sun et al. |
| 7,118,667 B2 | 10/2006 | Lee |
| 7,123,950 B2 | 10/2006 | Mannheimer |
| 7,125,382 B2 | 10/2006 | Zhou et al. |
| 7,134,999 B2 | 11/2006 | Brauker et al. |

(56) References Cited

U.S. PATENT DOCUMENTS

| | | |
|---|---|---|
| 7,136,689 B2 | 11/2006 | Shults et al. |
| 7,142,911 B2 | 11/2006 | Boileau et al. |
| 7,153,265 B2 | 12/2006 | Vachon |
| 7,155,290 B2 | 12/2006 | Von Arx et al. |
| 7,167,818 B2 | 1/2007 | Brown |
| 7,171,274 B2 | 1/2007 | Starkweather et al. |
| 7,174,199 B2 | 2/2007 | Berner et al. |
| 7,190,988 B2 | 3/2007 | Say et al. |
| 7,192,450 B2 | 3/2007 | Brauker et al. |
| 7,198,606 B2 | 4/2007 | Boecker et al. |
| 7,203,549 B2 | 4/2007 | Schommer et al. |
| 7,207,974 B2 | 4/2007 | Safabash et al. |
| 7,225,091 B2 | 5/2007 | Tivig et al. |
| 7,225,535 B2 | 6/2007 | Feldman et al. |
| 7,226,442 B2 | 6/2007 | Sheppard et al. |
| 7,226,978 B2 | 6/2007 | Tapsak et al. |
| 7,228,182 B2 | 6/2007 | Healy et al. |
| 7,237,712 B2 | 7/2007 | DeRocco et al. |
| 7,258,673 B2 | 8/2007 | Racchini et al. |
| 7,267,665 B2 | 9/2007 | Steil et al. |
| 7,272,436 B2 | 9/2007 | Gill et al. |
| 7,276,029 B2 | 10/2007 | Goode, Jr. et al. |
| 7,278,983 B2 | 10/2007 | Ireland et al. |
| 7,286,894 B1 | 10/2007 | Grant et al. |
| 7,295,867 B2 | 11/2007 | Berner et al. |
| 7,297,114 B2 | 11/2007 | Gill et al. |
| 7,299,082 B2 | 11/2007 | Feldman et al. |
| 7,310,544 B2 | 12/2007 | Brister et al. |
| 7,317,938 B2 | 1/2008 | Lorenz et al. |
| 7,335,294 B2 | 2/2008 | Heller et al. |
| 7,354,420 B2 | 4/2008 | Steil et al. |
| 7,364,592 B2 | 4/2008 | Carr-Brendel et al. |
| 7,366,556 B2 | 4/2008 | Brister et al. |
| 7,347,819 B2 | 5/2008 | Lebel et al. |
| 7,379,765 B2 | 5/2008 | Petisce et al. |
| 7,384,397 B2 | 6/2008 | Zhang et al. |
| 7,387,010 B2 | 6/2008 | Sunshine et al. |
| 7,399,277 B2 | 7/2008 | Saidara et al. |
| 7,402,153 B2 | 7/2008 | Steil et al. |
| 7,404,796 B2 | 7/2008 | Ginsberg |
| 7,419,573 B2 | 9/2008 | Gundel |
| 7,424,318 B2 | 9/2008 | Brister et al. |
| 7,429,255 B2 | 9/2008 | Thompson |
| 7,460,898 B2 | 12/2008 | Brister et al. |
| 7,467,003 B2 | 12/2008 | Brister et al. |
| 7,471,972 B2 | 12/2008 | Rhodes et al. |
| 7,474,992 B2 | 1/2009 | Ariyur |
| 7,492,254 B2 | 2/2009 | Bandy et al. |
| 7,494,465 B2 | 2/2009 | Brister et al. |
| 7,497,827 B2 | 3/2009 | Brister et al. |
| 7,499,002 B2 | 3/2009 | Blasko et al. |
| 7,502,644 B2 | 3/2009 | Gill et al. |
| 7,519,408 B2 | 4/2009 | Rasdal et al. |
| 7,524,287 B2 | 4/2009 | Bharmi |
| 7,547,281 B2 | 6/2009 | Hayes et al. |
| 7,563,588 B2 | 7/2009 | Gao et al. |
| 7,565,197 B2 | 7/2009 | Haubrich et al. |
| 7,569,030 B2 | 8/2009 | Lebel et al. |
| 7,574,266 B2 | 8/2009 | Dudding et al. |
| 7,583,990 B2 | 9/2009 | Goode, Jr. et al. |
| 7,591,801 B2 | 9/2009 | Brauker et al. |
| 7,599,726 B2 | 10/2009 | Goode, Jr. et al. |
| 7,602,310 B2 | 10/2009 | Mann et al. |
| 7,604,178 B2 | 10/2009 | Stewart |
| 7,613,491 B2 | 11/2009 | Boock et al. |
| 7,615,007 B2 | 11/2009 | Shults et al. |
| 7,618,369 B2 | 11/2009 | Hayter et al. |
| 7,630,748 B2 | 12/2009 | Budiman |
| 7,632,228 B2 | 12/2009 | Brauker et al. |
| 7,635,594 B2 | 12/2009 | Holmes et al. |
| 7,637,868 B2 | 12/2009 | Saint et al. |
| 7,640,048 B2 | 12/2009 | Dobbles et al. |
| 7,651,596 B2 | 1/2010 | Petisce et al. |
| 7,651,845 B2 | 1/2010 | Doyle, III et al. |
| 7,653,425 B2 | 1/2010 | Hayter et al. |
| 7,654,956 B2 | 2/2010 | Brister et al. |
| 7,659,823 B1 | 2/2010 | Killian et al. |
| 7,668,596 B2 | 2/2010 | Von Arx et al. |
| 7,699,775 B2 | 4/2010 | Desai et al. |
| 7,699,964 B2 | 4/2010 | Feldman et al. |
| 7,711,402 B2 | 5/2010 | Shults et al. |
| 7,713,574 B2 | 5/2010 | Brister et al. |
| 7,715,893 B2 | 5/2010 | Kamath et al. |
| 7,736,310 B2 | 6/2010 | Taub et al. |
| 7,741,734 B2 | 6/2010 | Joannopoulos et al. |
| 7,766,829 B2 | 8/2010 | Sloan et al. |
| 7,768,386 B2 | 8/2010 | Hayter et al. |
| 7,768,387 B2 | 8/2010 | Fennell et al. |
| 7,771,352 B2 | 8/2010 | Shults et al. |
| 7,774,145 B2 | 8/2010 | Bruaker et al. |
| 7,775,444 B2 | 8/2010 | DeRocco et al. |
| 7,778,680 B2 | 8/2010 | Goode, Jr. et al. |
| 7,779,332 B2 | 8/2010 | Karr et al. |
| 7,782,192 B2 | 8/2010 | Jeckelmann et al. |
| 7,783,333 B2 | 8/2010 | Brister et al. |
| 7,791,467 B2 | 9/2010 | Mazar et al. |
| 7,792,562 B2 | 9/2010 | Shults et al. |
| 7,811,231 B2 | 10/2010 | Jin et al. |
| 7,813,809 B2 | 10/2010 | Strother et al. |
| 7,826,382 B2 | 11/2010 | Sicurello et al. |
| 7,826,981 B2 | 11/2010 | Goode, Jr. et al. |
| 7,831,310 B2 | 11/2010 | Lebel et al. |
| 7,860,574 B2 | 12/2010 | Von Arx et al. |
| 7,866,026 B1 | 1/2011 | Wang et al. |
| 7,882,611 B2 | 2/2011 | Shah et al. |
| 7,889,069 B2 | 2/2011 | Fifolt et al. |
| 7,899,511 B2 | 3/2011 | Shults et al. |
| 7,899,545 B2 | 3/2011 | John |
| 7,905,833 B2 | 3/2011 | Brister et al. |
| 7,912,674 B2 | 3/2011 | Killoren Clark et al. |
| 7,914,450 B2 | 3/2011 | Goode, Jr. et al. |
| 7,916,013 B2 | 3/2011 | Stevenson |
| 7,920,906 B2 | 4/2011 | Goode, Jr. et al. |
| 7,928,850 B2 | 4/2011 | Hayter et al. |
| 7,938,797 B2 | 5/2011 | Estes |
| 7,941,200 B2 | 5/2011 | Weinart et al. |
| 7,946,985 B2 | 5/2011 | Mastrototaro et al. |
| 7,955,258 B2 | 6/2011 | Goscha et al. |
| 7,970,448 B2 | 6/2011 | Shults et al. |
| 7,972,296 B2 | 7/2011 | Braig et al. |
| 7,974,672 B2 | 7/2011 | Shults et al. |
| 7,976,466 B2 | 7/2011 | Ward et al. |
| 7,978,063 B2 | 7/2011 | Baldus et al. |
| 7,999,674 B2 | 8/2011 | Kamen |
| 8,010,174 B2 | 8/2011 | Goode, Jr. et al. |
| 8,010,256 B2 | 8/2011 | Oowada |
| 8,160,900 B2 | 4/2012 | Taub et al. |
| 8,192,394 B2 | 6/2012 | Estes et al. |
| 8,216,138 B1 | 7/2012 | McGarraugh et al. |
| 8,282,549 B2 | 10/2012 | Brauker et al. |
| 8,461,985 B2 | 6/2013 | Fennell et al. |
| 8,478,557 B2 | 7/2013 | Hayter et al. |
| 8,597,570 B2 | 12/2013 | Terashima et al. |
| 2001/0037366 A1 | 11/2001 | Webb et al. |
| 2001/0048362 A1 | 12/2001 | Spencer |
| 2002/0019022 A1 | 2/2002 | Dunn et al. |
| 2002/0019612 A1 | 2/2002 | Watanabe et al. |
| 2002/0042090 A1 | 4/2002 | Heller et al. |
| 2002/0054320 A1 | 5/2002 | Ogino |
| 2002/0068860 A1 | 6/2002 | Clark |
| 2002/0072784 A1 | 6/2002 | Sheppard et al. |
| 2002/0095076 A1 | 7/2002 | Krausman et al. |
| 2002/0103499 A1 | 8/2002 | Perez et al. |
| 2002/0106709 A1 | 8/2002 | Potts et al. |
| 2002/0128594 A1 | 9/2002 | Das et al. |
| 2002/0130779 A1 | 9/2002 | Ford |
| 2002/0143266 A1 | 10/2002 | Bock |
| 2002/0147135 A1 | 10/2002 | Schnell |
| 2002/0161288 A1 | 10/2002 | Shin et al. |
| 2002/0169439 A1 | 11/2002 | Flaherty et al. |
| 2002/0169635 A1 | 11/2002 | Shillingburg |
| 2002/0193679 A1 | 12/2002 | Malave et al. |
| 2003/0004403 A1 | 1/2003 | Drinan et al. |
| 2003/0023461 A1 | 1/2003 | Quintanilla et al. |

(56) References Cited

U.S. PATENT DOCUMENTS

| | | |
|---|---|---|
| 2003/0028089 A1 | 2/2003 | Galley et al. |
| 2003/0032867 A1 | 2/2003 | Crothall et al. |
| 2003/0042137 A1 | 3/2003 | Mao et al. |
| 2003/0050546 A1 | 3/2003 | Desai et al. |
| 2003/0055380 A1 | 3/2003 | Flaherty et al. |
| 2003/0060692 A1 | 3/2003 | Ruchti et al. |
| 2003/0060753 A1 | 3/2003 | Starkweather et al. |
| 2003/0065308 A1 | 4/2003 | Lebel et al. |
| 2003/0100040 A1 | 5/2003 | Bonnecaze et al. |
| 2003/0100821 A1 | 5/2003 | Heller et al. |
| 2003/0114897 A1 | 6/2003 | Von Arx et al. |
| 2003/0125612 A1 | 7/2003 | Fox et al. |
| 2003/0130616 A1 | 7/2003 | Steil et al. |
| 2003/0134347 A1 | 7/2003 | Heller et al. |
| 2003/0147515 A1 | 8/2003 | Kai et al. |
| 2003/0167035 A1 | 9/2003 | Flaherty et al. |
| 2003/0168338 A1 | 9/2003 | Gao et al. |
| 2003/0176933 A1 | 9/2003 | Lebel et al. |
| 2003/0187338 A1 | 10/2003 | Say et al. |
| 2003/0191377 A1 | 10/2003 | Robinson et al. |
| 2003/0199790 A1 | 10/2003 | Boecker et al. |
| 2003/0208113 A1 | 11/2003 | Mault et al. |
| 2003/0212317 A1 | 11/2003 | Kovatchev et al. |
| 2003/0212379 A1 | 11/2003 | Bylund et al. |
| 2003/0216630 A1 | 11/2003 | Jersey-Willuhn et al. |
| 2003/0217966 A1 | 11/2003 | Tapsak et al. |
| 2003/0225361 A1 | 12/2003 | Sabra |
| 2004/0010186 A1 | 1/2004 | Kimball et al. |
| 2004/0010207 A1 | 1/2004 | Flaherty et al. |
| 2004/0015131 A1 | 1/2004 | Flaherty et al. |
| 2004/0024553 A1 | 2/2004 | Monfre et al. |
| 2004/0034289 A1 | 2/2004 | Teller et al. |
| 2004/0039298 A1 | 2/2004 | Abreu |
| 2004/0040840 A1 | 3/2004 | Mao et al. |
| 2004/0041749 A1 | 3/2004 | Dixon |
| 2004/0045879 A1 | 3/2004 | Shults et al. |
| 2004/0054263 A1 | 3/2004 | Moerman et al. |
| 2004/0063435 A1 | 4/2004 | Sakamoto et al. |
| 2004/0064068 A1 | 4/2004 | DeNuzzio et al. |
| 2004/0064088 A1 | 4/2004 | Gorman et al. |
| 2004/0064096 A1 | 4/2004 | Flaherty et al. |
| 2004/0099529 A1 | 5/2004 | Mao et al. |
| 2004/0106858 A1 | 6/2004 | Say et al. |
| 2004/0122353 A1 | 6/2004 | Shahmirian et al. |
| 2004/0133164 A1 | 7/2004 | Funderburk et al. |
| 2004/0133390 A1 | 7/2004 | Osorio et al. |
| 2004/0135684 A1 | 7/2004 | Steinthal et al. |
| 2004/0138588 A1 | 7/2004 | Saikley et al. |
| 2004/0138716 A1 | 7/2004 | Kon et al. |
| 2004/0146909 A1 | 7/2004 | Duong et al. |
| 2004/0147872 A1 | 7/2004 | Thompson |
| 2004/0152622 A1 | 8/2004 | Keith et al. |
| 2004/0153032 A1 | 8/2004 | Garribotto et al. |
| 2004/0167464 A1 | 8/2004 | Ireland et al. |
| 2004/0167801 A1 | 8/2004 | Say et al. |
| 2004/0171921 A1 | 9/2004 | Say et al. |
| 2004/0172307 A1 | 9/2004 | Gruber |
| 2004/0176672 A1 | 9/2004 | Silver et al. |
| 2004/0186362 A1 | 9/2004 | Brauker et al. |
| 2004/0186365 A1 | 9/2004 | Jin et al. |
| 2004/0193090 A1 | 9/2004 | Lebel et al. |
| 2004/0197846 A1 | 10/2004 | Hockersmith et al. |
| 2004/0199056 A1 | 10/2004 | Husemann et al. |
| 2004/0199059 A1 | 10/2004 | Brauker et al. |
| 2004/0204687 A1 | 10/2004 | Mogensen et al. |
| 2004/0204868 A1 | 10/2004 | Maynard et al. |
| 2004/0208780 A1 | 10/2004 | Faries, Jr. et al. |
| 2004/0219664 A1 | 11/2004 | Heller et al. |
| 2004/0225338 A1 | 11/2004 | Lebel et al. |
| 2004/0236200 A1 | 11/2004 | Say et al. |
| 2004/0249420 A1 | 12/2004 | Olson et al. |
| 2004/0254433 A1 | 12/2004 | Bandis et al. |
| 2004/0254434 A1 | 12/2004 | Goodnow et al. |
| 2004/0260478 A1 | 12/2004 | Schwamm |
| 2004/0267300 A1 | 12/2004 | Mace |
| 2005/0001024 A1 | 1/2005 | Kusaka et al. |
| 2005/0003470 A1 | 1/2005 | Nelson et al. |
| 2005/0004439 A1 | 1/2005 | Shin et al. |
| 2005/0004494 A1 | 1/2005 | Perez et al. |
| 2005/0010087 A1 | 1/2005 | Banet et al. |
| 2005/0010269 A1 | 1/2005 | Lebel et al. |
| 2005/0016276 A1 | 1/2005 | Guan et al. |
| 2005/0017864 A1 | 1/2005 | Tsoukalis |
| 2005/0027177 A1 | 2/2005 | Shin et al. |
| 2005/0027180 A1 | 2/2005 | Goode, Jr. et al. |
| 2005/0027181 A1 | 2/2005 | Goode, Jr. et al. |
| 2005/0027462 A1 | 2/2005 | Goode, Jr. et al. |
| 2005/0027463 A1 | 2/2005 | Goode, Jr. et al. |
| 2005/0031689 A1 | 2/2005 | Shults et al. |
| 2005/0038332 A1 | 2/2005 | Saidara et al. |
| 2005/0043598 A1 | 2/2005 | Goode, Jr. et al. |
| 2005/0049179 A1 | 3/2005 | Davidson et al. |
| 2005/0070774 A1 | 3/2005 | Addison et al. |
| 2005/0070777 A1 | 3/2005 | Cho et al. |
| 2005/0090607 A1 | 4/2005 | Tapsak et al. |
| 2005/0096516 A1 | 5/2005 | Soykan et al. |
| 2005/0113886 A1 | 5/2005 | Fischell et al. |
| 2005/0114068 A1 | 5/2005 | Chey et al. |
| 2005/0116683 A1 | 6/2005 | Cheng et al. |
| 2005/0121322 A1 | 6/2005 | Say et al. |
| 2005/0131346 A1 | 6/2005 | Douglas |
| 2005/0137530 A1 | 6/2005 | Campbell et al. |
| 2005/0143635 A1 | 6/2005 | Kamath et al. |
| 2005/0176136 A1 | 8/2005 | Burd et al. |
| 2005/0177398 A1 | 8/2005 | Watanabe et al. |
| 2005/0182306 A1 | 8/2005 | Sloan |
| 2005/0187442 A1 | 8/2005 | Cho et al. |
| 2005/0192494 A1 | 9/2005 | Ginsberg |
| 2005/0192557 A1 | 9/2005 | Brauker et al. |
| 2005/0195930 A1 | 9/2005 | Spital et al. |
| 2005/0199494 A1 | 9/2005 | Say et al. |
| 2005/0203360 A1 | 9/2005 | Brauker et al. |
| 2005/0204134 A1 | 9/2005 | Von Arx et al. |
| 2005/0214892 A1 | 9/2005 | Kovatchev et al. |
| 2005/0236361 A1 | 10/2005 | Ufer et al. |
| 2005/0239154 A1 | 10/2005 | Feldman et al. |
| 2005/0241957 A1 | 11/2005 | Mao et al. |
| 2005/0245795 A1 | 11/2005 | Goode, Jr. et al. |
| 2005/0245799 A1 | 11/2005 | Brauker et al. |
| 2005/0245839 A1 | 11/2005 | Stivoric et al. |
| 2005/0245904 A1 | 11/2005 | Estes et al. |
| 2005/0251033 A1 | 11/2005 | Scarantino et al. |
| 2005/0272985 A1 | 12/2005 | Kotulla et al. |
| 2005/0277912 A1 | 12/2005 | John |
| 2005/0287620 A1 | 12/2005 | Heller et al. |
| 2005/0288725 A1 | 12/2005 | Hettrick et al. |
| 2006/0001538 A1 | 1/2006 | Kraft et al. |
| 2006/0001551 A1 | 1/2006 | Kraft et al. |
| 2006/0004270 A1 | 1/2006 | Bedard et al. |
| 2006/0010098 A1 | 1/2006 | Goodnow et al. |
| 2006/0015020 A1 | 1/2006 | Neale et al. |
| 2006/0015024 A1 | 1/2006 | Brister et al. |
| 2006/0016700 A1 | 1/2006 | Brister et al. |
| 2006/0017923 A1 | 1/2006 | Ruchti et al. |
| 2006/0019327 A1 | 1/2006 | Brister et al. |
| 2006/0020187 A1 | 1/2006 | Brister et al. |
| 2006/0020188 A1 | 1/2006 | Kamath et al. |
| 2006/0020189 A1 | 1/2006 | Brister et al. |
| 2006/0020190 A1 | 1/2006 | Kamath et al. |
| 2006/0020191 A1 | 1/2006 | Brister et al. |
| 2006/0020192 A1 | 1/2006 | Brister et al. |
| 2006/0020300 A1 | 1/2006 | Nghiem et al. |
| 2006/0025663 A1 | 2/2006 | Talbot et al. |
| 2006/0029177 A1 | 2/2006 | Cranford, Jr. et al. |
| 2006/0031094 A1 | 2/2006 | Cohen et al. |
| 2006/0036139 A1 | 2/2006 | Brister et al. |
| 2006/0036140 A1 | 2/2006 | Brister et al. |
| 2006/0036141 A1 | 2/2006 | Kamath et al. |
| 2006/0036142 A1 | 2/2006 | Brister et al. |
| 2006/0036143 A1 | 2/2006 | Brister et al. |
| 2006/0036144 A1 | 2/2006 | Brister et al. |
| 2006/0036145 A1 | 2/2006 | Brister et al. |
| 2006/0058588 A1 | 3/2006 | Zdeblick |
| 2006/0079740 A1 | 4/2006 | Silver et al. |

(56) References Cited

U.S. PATENT DOCUMENTS

| | | |
|---|---|---|
| 2006/0091006 A1 | 5/2006 | Wang et al. |
| 2006/0142651 A1 | 6/2006 | Brister et al. |
| 2006/0154642 A1 | 7/2006 | Scannell |
| 2006/0155180 A1 | 7/2006 | Brister et al. |
| 2006/0156796 A1 | 7/2006 | Burke et al. |
| 2006/0166629 A1 | 7/2006 | Reggiardo |
| 2006/0173260 A1 | 8/2006 | Gaoni et al. |
| 2006/0173406 A1 | 8/2006 | Hayes et al. |
| 2006/0173444 A1 | 8/2006 | Choy et al. |
| 2006/0183985 A1 | 8/2006 | Brister et al. |
| 2006/0189863 A1 | 8/2006 | Peyser et al. |
| 2006/0193375 A1 | 8/2006 | Lee et al. |
| 2006/0202805 A1 | 9/2006 | Schulman et al. |
| 2006/0211072 A1 | 9/2006 | Ryan et al. |
| 2006/0222566 A1 | 10/2006 | Brauker et al. |
| 2006/0224109 A1 | 10/2006 | Steil et al. |
| 2006/0224141 A1 | 10/2006 | Rush et al. |
| 2006/0226985 A1 | 10/2006 | Goodnow et al. |
| 2006/0229512 A1 | 10/2006 | Petisce et al. |
| 2006/0247508 A1 | 11/2006 | Fennell |
| 2006/0247685 A1 | 11/2006 | Bharmi |
| 2006/0247710 A1 | 11/2006 | Goetz et al. |
| 2006/0247985 A1 | 11/2006 | Liamos et al. |
| 2006/0253296 A1 | 11/2006 | Liisberg et al. |
| 2006/0258929 A1 | 11/2006 | Goode et al. |
| 2006/0264785 A1 | 11/2006 | Dring et al. |
| 2006/0272652 A1* | 12/2006 | Stocker .................. G16H 50/50 128/898 |
| 2006/0281985 A1 | 12/2006 | Ward et al. |
| 2006/0287691 A1 | 12/2006 | Drew |
| 2006/0290496 A1 | 12/2006 | Peeters et al. |
| 2006/0293607 A1 | 12/2006 | Alt et al. |
| 2007/0007133 A1 | 1/2007 | Mang et al. |
| 2007/0010950 A1 | 1/2007 | Abensour et al. |
| 2007/0016381 A1 | 1/2007 | Kamath et al. |
| 2007/0017983 A1 | 1/2007 | Frank et al. |
| 2007/0027381 A1 | 2/2007 | Stafford |
| 2007/0032706 A1 | 2/2007 | Kamath et al. |
| 2007/0032717 A1 | 2/2007 | Brister et al. |
| 2007/0033074 A1 | 2/2007 | Nitzan et al. |
| 2007/0038044 A1 | 2/2007 | Dobbles et al. |
| 2007/0055799 A1 | 3/2007 | Koehler et al. |
| 2007/0056858 A1 | 3/2007 | Chen et al. |
| 2007/0060803 A1 | 3/2007 | Liljeryd et al. |
| 2007/0060814 A1 | 3/2007 | Stafford |
| 2007/0060869 A1 | 3/2007 | Tolle et al. |
| 2007/0060979 A1 | 3/2007 | Strother et al. |
| 2007/0066873 A1 | 3/2007 | Kamath et al. |
| 2007/0066956 A1 | 3/2007 | Finkel |
| 2007/0068807 A1 | 3/2007 | Feldman et al. |
| 2007/0071681 A1 | 3/2007 | Gadkar et al. |
| 2007/0073129 A1 | 3/2007 | Shah et al. |
| 2007/0078320 A1 | 4/2007 | Stafford |
| 2007/0078321 A1 | 4/2007 | Mazza et al. |
| 2007/0078322 A1 | 4/2007 | Stafford |
| 2007/0078323 A1 | 4/2007 | Reggiardo et al. |
| 2007/0078818 A1 | 4/2007 | Zvitz et al. |
| 2007/0093786 A1 | 4/2007 | Goldsmith et al. |
| 2007/0094216 A1 | 4/2007 | Mathias et al. |
| 2007/0095661 A1 | 5/2007 | Wang et al. |
| 2007/0100222 A1 | 5/2007 | Mastrototaro et al. |
| 2007/0106135 A1 | 5/2007 | Sloan et al. |
| 2007/0108048 A1 | 5/2007 | Wang et al. |
| 2007/0118405 A1 | 5/2007 | Campbell et al. |
| 2007/0124002 A1 | 5/2007 | Estes et al. |
| 2007/0149875 A1 | 6/2007 | Ouyang et al. |
| 2007/0153705 A1 | 7/2007 | Rosar et al. |
| 2007/0156094 A1 | 7/2007 | Safabash et al. |
| 2007/0168224 A1 | 7/2007 | Letzt et al. |
| 2007/0173706 A1 | 7/2007 | Neinast et al. |
| 2007/0173709 A1 | 7/2007 | Petisce et al. |
| 2007/0173710 A1 | 7/2007 | Petisce et al. |
| 2007/0173761 A1 | 7/2007 | Kanderian et al. |
| 2007/0179349 A1 | 8/2007 | Hoyme et al. |
| 2007/0179352 A1 | 8/2007 | Randlov et al. |
| 2007/0179434 A1 | 8/2007 | Weinert et al. |
| 2007/0191701 A1 | 8/2007 | Feldman et al. |
| 2007/0191702 A1 | 8/2007 | Yodfat et al. |
| 2007/0203407 A1 | 8/2007 | Hoss et al. |
| 2007/0203966 A1 | 8/2007 | Brauker et al. |
| 2007/0208246 A1 | 9/2007 | Brauker et al. |
| 2007/0213657 A1 | 9/2007 | Jennewine et al. |
| 2007/0228071 A1 | 10/2007 | Kamen et al. |
| 2007/0232877 A1 | 10/2007 | He |
| 2007/0232878 A1 | 10/2007 | Kovatchev et al. |
| 2007/0232880 A1 | 10/2007 | Siddiqui et al. |
| 2007/0235331 A1 | 10/2007 | Simpson et al. |
| 2007/0244383 A1 | 10/2007 | Talbot et al. |
| 2007/0249922 A1 | 10/2007 | Peyser et al. |
| 2007/0055348 A1 | 11/2007 | Holtzclaw |
| 2007/0253021 A1 | 11/2007 | Mehta et al. |
| 2007/0255321 A1 | 11/2007 | Gelber et al. |
| 2007/0255531 A1 | 11/2007 | Drew |
| 2007/0258395 A1 | 11/2007 | Jollota et al. |
| 2007/0270672 A1 | 11/2007 | Hayter |
| 2007/0271285 A1 | 11/2007 | Eichorn et al. |
| 2007/0282299 A1 | 12/2007 | Hellwig |
| 2007/0285238 A1 | 12/2007 | Batra |
| 2007/0287931 A1 | 12/2007 | Dilorenzo |
| 2007/0299617 A1 | 12/2007 | Willis |
| 2008/0009692 A1 | 1/2008 | Stafford |
| 2008/0017522 A1 | 1/2008 | Heller et al. |
| 2008/0018433 A1 | 1/2008 | Pitt-Pladdy |
| 2008/0021436 A1 | 1/2008 | Wolpert et al. |
| 2008/0021666 A1 | 1/2008 | Goode, Jr. et al. |
| 2008/0029391 A1 | 2/2008 | Mao et al. |
| 2008/0033254 A1 | 2/2008 | Kamath et al. |
| 2008/0039702 A1 | 2/2008 | Hayter et al. |
| 2008/0045824 A1 | 2/2008 | Tapsak et al. |
| 2008/0057484 A1 | 3/2008 | Miyata et al. |
| 2008/0058625 A1 | 3/2008 | McGarraugh et al. |
| 2008/0058626 A1 | 3/2008 | Miyata et al. |
| 2008/0058678 A1 | 3/2008 | Miyata et al. |
| 2008/0058773 A1 | 3/2008 | John |
| 2008/0060955 A1 | 3/2008 | Goodnow |
| 2008/0061961 A1 | 3/2008 | John |
| 2008/0064937 A1 | 3/2008 | McGarraugh et al. |
| 2008/0064943 A1 | 3/2008 | Talbot et al. |
| 2008/0071156 A1 | 3/2008 | Brister et al. |
| 2008/0071157 A1 | 3/2008 | McGarraugh et al. |
| 2008/0071158 A1 | 3/2008 | McGarraugh et al. |
| 2008/0071328 A1 | 3/2008 | Haubrich et al. |
| 2008/0081977 A1 | 4/2008 | Hayter et al. |
| 2008/0083617 A1 | 4/2008 | Simpson et al. |
| 2008/0086042 A1 | 4/2008 | Brister et al. |
| 2008/0086044 A1 | 4/2008 | Brister et al. |
| 2008/0086273 A1 | 4/2008 | Shults et al. |
| 2008/0092638 A1 | 4/2008 | Brenneman et al. |
| 2008/0097289 A1 | 4/2008 | Steil et al. |
| 2008/0108942 A1 | 5/2008 | Brister et al. |
| 2008/0114228 A1 | 5/2008 | McCluskey et al. |
| 2008/0119703 A1 | 5/2008 | Brister et al. |
| 2008/0119705 A1 | 5/2008 | Patel et al. |
| 2008/0139910 A1 | 6/2008 | Mastrototaro et al. |
| 2008/0154513 A1 | 6/2008 | Kovatchev et al. |
| 2008/0161666 A1 | 7/2008 | Feldman et al. |
| 2008/0167543 A1 | 7/2008 | Say et al. |
| 2008/0167572 A1 | 7/2008 | Stivoric et al. |
| 2008/0172205 A1 | 7/2008 | Breton et al. |
| 2008/0177149 A1 | 7/2008 | Weinert et al. |
| 2008/0182537 A1 | 7/2008 | Manku et al. |
| 2008/0183060 A1 | 7/2008 | Steil et al. |
| 2008/0183061 A1 | 7/2008 | Goode, Jr. et al. |
| 2008/0183399 A1 | 7/2008 | Goode, Jr. et al. |
| 2008/0188731 A1 | 8/2008 | Brister et al. |
| 2008/0188796 A1 | 8/2008 | Steil et al. |
| 2008/0189051 A1 | 8/2008 | Goode et al. |
| 2008/0194934 A1 | 8/2008 | Ray et al. |
| 2008/0194935 A1 | 8/2008 | Brister et al. |
| 2008/0194936 A1 | 8/2008 | Goode et al. |
| 2008/0194937 A1 | 8/2008 | Goode et al. |
| 2008/0194938 A1 | 8/2008 | Brister et al. |
| 2008/0195232 A1 | 8/2008 | Carr-Brendel et al. |
| 2008/0195967 A1 | 8/2008 | Goode et al. |

(56) References Cited

U.S. PATENT DOCUMENTS

| | | |
|---|---|---|
| 2008/0197024 A1 | 8/2008 | Simpson et al. |
| 2008/0200788 A1 | 8/2008 | Brister et al. |
| 2008/0200789 A1 | 8/2008 | Brister et al. |
| 2008/0200791 A1 | 8/2008 | Simpson et al. |
| 2008/0201325 A1 | 8/2008 | Doniger et al. |
| 2008/0208025 A1 | 8/2008 | Shults et al. |
| 2008/0208026 A1 | 8/2008 | Noujaim et al. |
| 2008/0208113 A1 | 8/2008 | Damiano et al. |
| 2008/0214900 A1 | 9/2008 | Fennell et al. |
| 2008/0214915 A1 | 9/2008 | Brister et al. |
| 2008/0214918 A1 | 9/2008 | Brister et al. |
| 2008/0228051 A1 | 9/2008 | Shults et al. |
| 2008/0228054 A1 | 9/2008 | Shults et al. |
| 2008/0228055 A1 | 9/2008 | Sher |
| 2008/0234663 A1 | 9/2008 | Yodfat et al. |
| 2008/0234943 A1 | 9/2008 | Ray et al. |
| 2008/0235469 A1 | 9/2008 | Drew |
| 2008/0242961 A1 | 10/2008 | Brister et al. |
| 2008/0242963 A1 | 10/2008 | Essenpreis et al. |
| 2008/0254544 A1 | 10/2008 | Modzelewski et al. |
| 2008/0255434 A1 | 10/2008 | Hayter et al. |
| 2008/0255437 A1 | 10/2008 | Hayter |
| 2008/0255438 A1 | 10/2008 | Saidara et al. |
| 2008/0255808 A1 | 10/2008 | Hayter |
| 2008/0256048 A1 | 10/2008 | Hayter |
| 2008/0262469 A1 | 10/2008 | Brister et al. |
| 2008/0267823 A1 | 10/2008 | Wang et al. |
| 2008/0269714 A1 | 10/2008 | Mastrototaro et al. |
| 2008/0269723 A1 | 10/2008 | Mastrototaro et al. |
| 2008/0275313 A1 | 11/2008 | Brister et al. |
| 2008/0287761 A1 | 11/2008 | Hayter |
| 2008/0287762 A1 | 11/2008 | Hayter |
| 2008/0287763 A1 | 11/2008 | Hayter |
| 2008/0287764 A1 | 11/2008 | Rasdal et al. |
| 2008/0287765 A1 | 11/2008 | Rasdal et al. |
| 2008/0287766 A1 | 11/2008 | Rasdal et al. |
| 2008/0288180 A1 | 11/2008 | Hayter |
| 2008/0288204 A1 | 11/2008 | Hayter et al. |
| 2008/0296155 A1 | 12/2008 | Shults et al. |
| 2008/0300572 A1* | 12/2008 | Rankers ............ A61B 5/14532 604/504 |
| 2008/0306368 A1 | 12/2008 | Goode et al. |
| 2008/0306434 A1 | 12/2008 | Dobbles et al. |
| 2008/0306435 A1 | 12/2008 | Kamath et al. |
| 2008/0306444 A1 | 12/2008 | Brister et al. |
| 2008/0312518 A1 | 12/2008 | Jina et al. |
| 2008/0312841 A1 | 12/2008 | Hayter |
| 2008/0312842 A1 | 12/2008 | Hayter |
| 2008/0312844 A1 | 12/2008 | Hayter et al. |
| 2008/0312845 A1 | 12/2008 | Hayter et al. |
| 2008/0312859 A1 | 12/2008 | Skyggebjerg et al. |
| 2008/0314395 A1 | 12/2008 | Kovatchev et al. |
| 2008/0319085 A1 | 12/2008 | Wright et al. |
| 2008/0319279 A1 | 12/2008 | Ramsay et al. |
| 2008/0319295 A1 | 12/2008 | Bernstein et al. |
| 2008/0319296 A1 | 12/2008 | Bernstein et al. |
| 2009/0005665 A1 | 1/2009 | Hayter et al. |
| 2009/0005666 A1 | 1/2009 | Shin et al. |
| 2009/0006034 A1 | 1/2009 | Hayter et al. |
| 2009/0006061 A1 | 1/2009 | Thukral et al. |
| 2009/0006133 A1 | 1/2009 | Weinert et al. |
| 2009/0012376 A1 | 1/2009 | Agus |
| 2009/0012379 A1 | 1/2009 | Goode, Jr. et al. |
| 2009/0018424 A1 | 1/2009 | Kamath et al. |
| 2009/0018425 A1 | 1/2009 | Ouyang et al. |
| 2009/0030294 A1 | 1/2009 | Petisce et al. |
| 2009/0033482 A1 | 2/2009 | Hayter et al. |
| 2009/0036747 A1 | 2/2009 | Hayter et al. |
| 2009/0036760 A1 | 2/2009 | Hayter |
| 2009/0036763 A1 | 2/2009 | Brauker et al. |
| 2009/0040022 A1 | 2/2009 | Finkenzeller |
| 2009/0043181 A1 | 2/2009 | Brauker et al. |
| 2009/0043182 A1 | 2/2009 | Brauker et al. |
| 2009/0043525 A1 | 2/2009 | Brauker et al. |
| 2009/0043541 A1 | 2/2009 | Brauker et al. |
| 2009/0043542 A1 | 2/2009 | Brauker et al. |
| 2009/0045055 A1 | 2/2009 | Rhodes et al. |
| 2009/0048503 A1 | 2/2009 | Dalal et al. |
| 2009/0054745 A1 | 2/2009 | Jennewine et al. |
| 2009/0054747 A1 | 2/2009 | Fennell |
| 2009/0054748 A1 | 2/2009 | Feldman et al. |
| 2009/0055149 A1 | 2/2009 | Hayter et al. |
| 2009/0062633 A1 | 3/2009 | Brauker et al. |
| 2009/0062635 A1 | 3/2009 | Brauker et al. |
| 2009/0062767 A1 | 3/2009 | VanAntwerp et al. |
| 2009/0063402 A1 | 3/2009 | Hayter |
| 2009/0076356 A1 | 3/2009 | Simpson et al. |
| 2009/0076360 A1 | 3/2009 | Brister et al. |
| 2009/0076361 A1 | 3/2009 | Kamath et al. |
| 2009/0082693 A1 | 3/2009 | Stafford |
| 2009/0085768 A1 | 4/2009 | Patel et al. |
| 2009/0085873 A1 | 4/2009 | Betts et al. |
| 2009/0088614 A1 | 4/2009 | Taub et al. |
| 2009/0093687 A1 | 4/2009 | Telfort et al. |
| 2009/0099436 A1 | 4/2009 | Brister et al. |
| 2009/0105554 A1 | 4/2009 | Stahmann et al. |
| 2009/0105560 A1 | 4/2009 | Solomon |
| 2009/0105570 A1 | 4/2009 | Sloan et al. |
| 2009/0105571 A1 | 4/2009 | Fennell et al. |
| 2009/0105636 A1 | 4/2009 | Hayter et al. |
| 2009/0112478 A1 | 4/2009 | Mueller, Jr. et al. |
| 2009/0118589 A1 | 5/2009 | Ueshima et al. |
| 2009/0124877 A1 | 5/2009 | Shariati et al. |
| 2009/0124878 A1 | 5/2009 | Goode, Jr. et al. |
| 2009/0124879 A1 | 5/2009 | Brister et al. |
| 2009/0124964 A1 | 5/2009 | Leach et al. |
| 2009/0131768 A1 | 5/2009 | Simpson et al. |
| 2009/0131769 A1 | 5/2009 | Leach et al. |
| 2009/0131776 A1 | 5/2009 | Simpson et al. |
| 2009/0131777 A1 | 5/2009 | Simpson et al. |
| 2009/0137886 A1 | 5/2009 | Shariati et al. |
| 2009/0137887 A1 | 5/2009 | Shariati et al. |
| 2009/0143659 A1 | 6/2009 | Li et al. |
| 2009/0143660 A1 | 6/2009 | Brister et al. |
| 2009/0150186 A1 | 6/2009 | Cohen et al. |
| 2009/0156919 A1 | 6/2009 | Brister et al. |
| 2009/0156924 A1 | 6/2009 | Shariati et al. |
| 2009/0163790 A1 | 6/2009 | Brister et al. |
| 2009/0163791 A1 | 6/2009 | Brister et al. |
| 2009/0164190 A1 | 6/2009 | Hayter |
| 2009/0164239 A1 | 6/2009 | Hayter et al. |
| 2009/0164251 A1 | 6/2009 | Hayter |
| 2009/0178459 A1 | 7/2009 | Li et al. |
| 2009/0182217 A1 | 7/2009 | Li et al. |
| 2009/0189738 A1 | 7/2009 | Hermle |
| 2009/0192366 A1 | 7/2009 | Mensinger et al. |
| 2009/0192380 A1 | 7/2009 | Shariati et al. |
| 2009/0192722 A1 | 7/2009 | Shariati et al. |
| 2009/0192724 A1 | 7/2009 | Brauker et al. |
| 2009/0192745 A1 | 7/2009 | Kamath et al. |
| 2009/0192751 A1 | 7/2009 | Kamath et al. |
| 2009/0198118 A1 | 8/2009 | Hayter et al. |
| 2009/0203981 A1 | 8/2009 | Brauker et al. |
| 2009/0204341 A1 | 8/2009 | Brauker et al. |
| 2009/0216100 A1 | 8/2009 | Ebner et al. |
| 2009/0216103 A1 | 8/2009 | Brister et al. |
| 2009/0227855 A1 | 9/2009 | Hill et al. |
| 2009/0234200 A1 | 9/2009 | Husheer |
| 2009/0240120 A1 | 9/2009 | Mensinger et al. |
| 2009/0240128 A1 | 9/2009 | Mensinger et al. |
| 2009/0240193 A1 | 9/2009 | Mensinger et al. |
| 2009/0240440 A1 | 9/2009 | Shurabura et al. |
| 2009/0242399 A1 | 10/2009 | Kamath et al. |
| 2009/0242425 A1 | 10/2009 | Kamath et al. |
| 2009/0247855 A1 | 10/2009 | Boock et al. |
| 2009/0247856 A1 | 10/2009 | Boock et al. |
| 2009/0247857 A1 | 10/2009 | Harper et al. |
| 2009/0247931 A1 | 10/2009 | Damgaard-Sorensen |
| 2009/0253973 A1 | 10/2009 | Bashan et al. |
| 2009/0267765 A1 | 10/2009 | Greene et al. |
| 2009/0287073 A1 | 11/2009 | Boock et al. |
| 2009/0287074 A1 | 11/2009 | Shults et al. |
| 2009/0289796 A1 | 11/2009 | Blumberg |
| 2009/0292188 A1 | 11/2009 | Hoss et al. |

(56) References Cited

U.S. PATENT DOCUMENTS

| | | |
|---|---|---|
| 2009/0296742 A1 | 12/2009 | Sicurello et al. |
| 2009/0298182 A1 | 12/2009 | Schulat et al. |
| 2009/0299155 A1 | 12/2009 | Yang et al. |
| 2009/0299156 A1 | 12/2009 | Simpson et al. |
| 2009/0299162 A1 | 12/2009 | Brauker et al. |
| 2009/0299276 A1 | 12/2009 | Brauker et al. |
| 2010/0010324 A1 | 1/2010 | Brauker et al. |
| 2010/0010329 A1 | 1/2010 | Taub et al. |
| 2010/0010331 A1 | 1/2010 | Brauker et al. |
| 2010/0010332 A1 | 1/2010 | Brauker et al. |
| 2010/0016687 A1 | 1/2010 | Brauker et al. |
| 2010/0016698 A1 | 1/2010 | Rasdal et al. |
| 2010/0022855 A1 | 1/2010 | Brauker et al. |
| 2010/0030038 A1 | 2/2010 | Brauker et al. |
| 2010/0030053 A1 | 2/2010 | Goode, Jr. et al. |
| 2010/0030484 A1 | 2/2010 | Brauker et al. |
| 2010/0030485 A1 | 2/2010 | Brauker et al. |
| 2010/0036215 A1 | 2/2010 | Goode, Jr. et al. |
| 2010/0036216 A1 | 2/2010 | Goode, Jr. et al. |
| 2010/0036222 A1 | 2/2010 | Goode, Jr. et al. |
| 2010/0036223 A1 | 2/2010 | Goode, Jr. et al. |
| 2010/0036225 A1 | 2/2010 | Goode, Jr. et al. |
| 2010/0041971 A1 | 2/2010 | Goode, Jr. et al. |
| 2010/0045465 A1 | 2/2010 | Brauker et al. |
| 2010/0049024 A1 | 2/2010 | Saint et al. |
| 2010/0056992 A1 | 3/2010 | Hayter et al. |
| 2010/0057040 A1 | 3/2010 | Hayter |
| 2010/0057041 A1 | 3/2010 | Hayter |
| 2010/0057042 A1 | 3/2010 | Hayter |
| 2010/0057044 A1 | 3/2010 | Hayter |
| 2010/0057057 A1 | 3/2010 | Hayter et al. |
| 2010/0063372 A1 | 3/2010 | Potts et al. |
| 2010/0063373 A1 | 3/2010 | Kamath et al. |
| 2010/0076283 A1 | 3/2010 | Simpson et al. |
| 2010/0081906 A1 | 4/2010 | Hayter et al. |
| 2010/0081908 A1 | 4/2010 | Dobbles et al. |
| 2010/0081909 A1 | 4/2010 | Budiman et al. |
| 2010/0081910 A1 | 4/2010 | Brister et al. |
| 2010/0087724 A1 | 4/2010 | Brauker et al. |
| 2010/0096259 A1 | 4/2010 | Zhang et al. |
| 2010/0099970 A1 | 4/2010 | Shults et al. |
| 2010/0099971 A1 | 4/2010 | Shults et al. |
| 2010/0105999 A1 | 4/2010 | Dixon et al. |
| 2010/0119693 A1 | 5/2010 | Tapsak et al. |
| 2010/0121169 A1 | 5/2010 | Petisce et al. |
| 2010/0141656 A1 | 6/2010 | Krieftewirth |
| 2010/0152554 A1 | 6/2010 | Steine et al. |
| 2010/0160759 A1 | 6/2010 | Celentano et al. |
| 2010/0168538 A1 | 7/2010 | Keenan et al. |
| 2010/0168546 A1 | 7/2010 | Kamath et al. |
| 2010/0174266 A1 | 7/2010 | Estes |
| 2010/0185175 A1 | 7/2010 | Kamen et al. |
| 2010/0190435 A1 | 7/2010 | Cook et al. |
| 2010/0191082 A1 | 7/2010 | Brister et al. |
| 2010/0204557 A1 | 8/2010 | Kiaie et al. |
| 2010/0213080 A1 | 8/2010 | Celentano et al. |
| 2010/0234710 A1 | 9/2010 | Budiman et al. |
| 2010/0240975 A1 | 9/2010 | Goode, Jr. et al. |
| 2010/0274111 A1 | 10/2010 | Say et al. |
| 2010/0280441 A1 | 11/2010 | Willinska et al. |
| 2010/0312176 A1 | 12/2010 | Lauer et al. |
| 2010/0313105 A1 | 12/2010 | Neekoomaram et al. |
| 2011/0004276 A1 | 1/2011 | Blair et al. |
| 2011/0024043 A1 | 2/2011 | Boock et al. |
| 2011/0024307 A1 | 2/2011 | Simpson et al. |
| 2011/0027127 A1 | 2/2011 | Simpson et al. |
| 2011/0027453 A1 | 2/2011 | Boock et al. |
| 2011/0027458 A1 | 2/2011 | Boock et al. |
| 2011/0028815 A1 | 2/2011 | Simpson et al. |
| 2011/0028816 A1 | 2/2011 | Simpson et al. |
| 2011/0031986 A1 | 2/2011 | Bhat et al. |
| 2011/0077490 A1 | 3/2011 | Simpson et al. |
| 2011/0148905 A1 | 6/2011 | Simmons et al. |
| 2011/0152637 A1 | 6/2011 | Kateraas et al. |
| 2011/0208027 A1 | 8/2011 | Wagner et al. |
| 2011/0208155 A1 | 8/2011 | Palerm et al. |
| 2011/0257895 A1 | 10/2011 | Brauker et al. |
| 2011/0287528 A1 | 11/2011 | Fern et al. |
| 2011/0320130 A1 | 12/2011 | Valdes et al. |
| 2012/0078071 A1 | 3/2012 | Bohm et al. |
| 2012/0108934 A1 | 5/2012 | Valdes et al. |
| 2012/0165626 A1 | 6/2012 | Irina et al. |
| 2012/0165640 A1 | 6/2012 | Galley et al. |
| 2012/0173200 A1 | 7/2012 | Breton et al. |
| 2012/0190989 A1 | 7/2012 | Kaiser et al. |
| 2012/0215462 A1 | 8/2012 | Goode et al. |
| 2013/0035575 A1 | 2/2013 | Mayou et al. |
| 2013/0235166 A1 | 9/2013 | Jones et al. |

FOREIGN PATENT DOCUMENTS

| | | |
|---|---|---|
| EP | 0320109 | 6/1989 |
| EP | 0390390 | 10/1990 |
| EP | 0396788 | 11/1990 |
| EP | 0286118 | 1/1995 |
| EP | 1677668 | 7/2010 |
| WO | WO-2000/059370 | 10/2000 |
| WO | WO-2001/052935 | 7/2001 |
| WO | WO-2001/054753 | 8/2001 |
| WO | WO-2003/082091 | 10/2003 |
| WO | WO-2007/097754 | 8/2007 |
| WO | WO-2008/143943 | 11/2008 |

OTHER PUBLICATIONS

WO, PCT/US2009/055453 ISR and Written Opinion, dated Oct. 20, 2009.

WO, PCT/US2009/055454 ISR and Written Opinion, dated Oct. 20, 2009.

WO, PCT/US2009/055455 ISR and Written Opinion, dated Oct. 7, 2009.

WO, PCT/US2009/055457 ISR and Written Opinion, dated Nov. 13, 2009.

WO, PCT/US2009/055458 ISR and Written Opinion, dated Oct. 7, 2009.

WO, PCT/US2009/055459 ISR and Written Opinion, dated Oct. 22, 2009.

WO, PCT/US2009/058894 ISR and Written Opinion, dated Nov. 30, 2009.

Armour, J. C., et al., "Application of Chronic Intravascular Blood Glucose Sensor in Dogs", *Diabetes*, vol. 39, 1990, pp. 1519-1526.

Aussedat, B., et al., "A User-Friendly Method for Calibrating a Subcutaneous Glucose Sensor-Based Hypoglycemic Alarm", Biosensors & Bioelectronics, vol. 12, No. 11, 1997, pp. 1061-1070.

Bennion, N., et al., "Alternate Site Glucose Testing: A Crossover Design", *Diabetes Technology & Therapeutics*, vol. 4, No. 1, 2002, pp. 25-33.

Blank, T. B., et al., "Clinical Results From a Non-Invasive Blood Glucose Monitor", *Optical Diagnostics and Sensing of Biological Fluids and Glucose and Cholesterol Monitoring II, Proceedings of SPIE*, vol. 4624, 2002, pp. 1-10.

Blendea, M. C., et al, "Heart Disease in Diabetic Patients", Current Diabetes Reports, vol. 3, 2003, pp. 223-229.

Bremer, T. M., et al., "Benchmark Data from the Literature for Evaluation of New Glucose Sensing Technologies", Diabetes Technology & Therapeutics, vol. 3, No. 3, 2001, pp. 409-418.

Brooks, S. L., et al., "Development of an On-Line Glucose Sensor for Fermentation Monitoring", *Biosensors*, vol. 3, 1987/88, pp. 45-56.

Cass, A. E., et al., "Ferrocene-Medicated Enzyme Electrode for Amperometric Determination of Glucose", *Analytical Chemistry*, vol. 56, No. 4, 1984, 667-671.

Cheyne, E. H., et al., "Performance of a Continuous Glucose Monitoring System During Controlled Hypoglycaemia in Healthy Volunteers", Diabetes Technology & Therapeutics, vol. 4, No. 5, 2002, pp. 607-613.

Csoregi, E., et al., "Design and Optimization of a Selective Subcutaneously Implantable Glucose Electrode Based on 'Wired' Glucose Oxidase", *Analytical Chemistry*, vol. 67, No. 7, 1995, pp. 1240-1244.

(56) References Cited

OTHER PUBLICATIONS

Diabetes Control and Complications Trial Research Group, "The Effect of Intensive Treatment of Diabetes on the Development and Progression of Long-Term Complications in Insulin-Dependent Diabetes Mellitus", New England J. Med., vol. 329, No. 13, 1993, pp. 977-986.

Eckert, B. et al. "Hypoglycaemia leads to an increased QT interval in normal men", Clinical Physiology, vol. 18, No. 6, 1998, pp. 570-575.

El-Khatib, F. H., et al., "Adaptive Closed-Loop Control Provides Blood-Glucose Regulation Using Subcutaneous Insulin and Glucagon Infusion in Diabetic Swine", Journal of Diabetes Science and Technology, vol. 1, No. 2, 2007, pp. 181-192.

Feldman, B., et al., "A Continuous Glucose Sensor Based on Wired Enzyme™ Technology—Results from a 3-Day Trial in Patients with Type 1 Diabetes", Diabetes Technology & Therapeutics, vol. 5, No. 5, 2003, pp. 769-779.

Feldman, B., et al., "Correlation of Glucose Concentrations in Interstitial Fluid and Venous Blood During Periods of Rapid Glucose Change", Abbott Diabetes Care, Inc. Freestyle Navigator Continous Glucose Monitor Pamphlet, 2004.

Garg, S., et al., "Improvement in Glycemic Excursions with a Transcutaneous, Real-Time Continuous Glucose Sensor", Diabetes Care, vol. 29, No. 1, 2006, pp. 44-50.

Georgescu, B., et al., "Real-Time Multi-model Tracking of Myocardium in Echocardiography Using Robust Information Fusion", Medical Image Computing and Computer-Assisted Intervention, 2004, pp. 777-785.

Goldman, J.M., et al., "Masimo Signal Extraction Pulse Oximetry", Journal of Clinical Monitoring and Computing, vol. 16, No. 7, 2000, pp. 475-483.

Harris, N. D., et al., "Can Changes in QT Interval be used to Predict the Onset of Hypoglycemia in Type 1 Diabetes?," Computers in Cardiology, vol. 27, 2000, pp. 375-378.

Heller, S. R., "Abnormalities of the electrocardiogram during hypoglycemia: the cause of the dead in bed syndrome?," International Journal of Clinical Practice, Suppl. No. 129, 2002, pp. 27-32.

Isermann, R., "Supervision, Fault-Detection and Fault-Diagnosis Methods— An Introduction", Control Engineering Practice, vol. 5, No. 5, 1997, pp. 639-652.

Isermann, R., et al., "Trends in the Application of Model-Based Fault Detection and Diagnosis of Technical Processes", Control Engineering Practice, vol. 5, No. 5, 1997, pp. 709-719.

Johnson, P. C., "Peripheral Circulation", John Wiley & Sons, 1978, pp. 198.

Jones, T. W., et al., "Mild Hypoglycemia and Impairment of Brain Stem and Cortical Evoked Potentials in Healthy Subjects," Diabetes, vol. 39, 1990, pp. 1550-1555.

Jungheim, K., et al., "How Rapid Does Glucose Concentration Change in Daily Life of Patients with Type 1 Diabetes?", 2002, pp. 250.

Jungheim, K., et al., "Risky Delay of Hypoglycemia Detection by Glucose Monitoring at the Arm", Diabetes Care, vol. 24, No. 7, 2001, pp. 1303-1304.

Kaplan, S. M., "Wiley Electrical and Electronics Engineering Dictionary", IEEE Press, 2004, pp. 141, 142, 548, 549.

Kuure-Kinsey, M., et al., "Dual-Rate Kalman Filter for Continuous Glucose Monitoring", Proceedings of the 28th IEEE, EMBS Annual International Conference, New York City, 2006, pp. 63-66.

Landstedt-Hallin, L., et al., "Increased QT dispersion during hypoglycaemia in patients with type 2 diabetes mellitus," Journal of Internal Medicine, vol. 246, 1999, pp. 299-307.

Li, Y., et al., "In Vivo Release From a Drug Delivery MEMS Device", Journal of Controlled Release, vol. 100, 2004, pp. 211-219.

Lo, B., et al., "Key Technical Challenges and Current Implementations of Body Sensor Networks", Body Sensor Networks, 2005, pp. 1-5.

Lodwig, V., et al., "Continuous Glucose Monitoring with Glucose Sensors: Calibration and Assessment Criteria", Diabetes Technology & Therapeutics, vol. 5. No. 4, 2003, pp. 573-587.

Lortz, J., et al., "What is Bluetooth? We Explain The Newest Short-Range Connectivity Technology", Smart Computing Learning Series, Wireless Computing, vol. 8, Issue 5, 2002, pp. 72-74.

Maher, R. C., "A Method for Extrapolation of Missing Digital Audio Data", Preprints of Papers Presented at the AES Convention, 1993, pp. 1-19.

Maher, R.C., "Audio Enhancement using Nonlinear Time-Frequency Filtering", AES 26th International Conference, 2005, pp. 1-9.

Malin, S. F., et al., "Noninvasive Prediction of Glucose by Near-Infrared Diffuse Reflectance Spectoscopy", Clinical Chemistry, vol. 45, No. 9, 1999, pp. 1651-1658.

Malmberg, K., "Prospective randomised study of intensive insulin treatment on long-term survival after acute myocardial infarction in patients with diabetes mellitus", British Medical Journal, vol. 314, 1997, pp. 1512-1515.

Markel, A., et al, "Hypoglycaemia-Induced Ischaemic ECG Changes", La Presse Medicale, vol. 23, No. 2, 1994, pp. 78-79.

McGarraugh, G., et al., "Glucose Measurements Using Blood Extracted from the Forearm and the Finger", TheraSense, Inc., 2001, 16 Pages.

McGarraugh, G., et al., "Physiological Influences on Off-Finger Glucose Testing", Diabetes Technology & Therapeutics, vol. 3, No. 3, 2001, pp. 367-376.

McKean, B. D., et al., "A Telemetry-Instrumentation System for Chronically Implanted Glucose and Oxygen Sensors", IEEE Transactions on Biomedical Engineering, vol. 35, No. 7, 1998, pp. 526-532.

Morbiducci, U., et al., "Improved Usability of the Minimal Model of Insulin Sensitivity Based on an Automated Approach and Genetic Algorithms for Parameter Estimation", Clinical Science, vol. 112, 2007, pp. 257-263.

Mougiakakou, et al., "A Real Time Simulation Model of Glucose-Insulin Metabolism for Type 1 Diabetes Patients", Proceedings of the 2005 IEEE 2005, pp. 298-301.

Okin, P. M., et al, "Electrocardiographic Repolarization Complexity and Abnormality Predict All-Cause and Cardiovascular Mortality in Diabetes," Diabetes, vol. 53, 2004, pp. 434-440.

Panteleon, A. E., et al., "The Role of the Independent Variable to Glucose Sensor Calibration", Diabetes Technology & Therapeutics, vol. 5, No. 3, 2003, pp. 401-410.

Parker, R., et al., "Robust H∞ Glucose Control in Diabetes Using a Physiological Model", AIChE Journal, vol. 46, No. 12, 2000, pp. 2537-2549.

Peterson, K.G., et al., "Regulation of Serum Potassium During Insulin-Induced Hypoglycemia", Diabetes, vol. 31, 1982, pp. 615-617.

Pickup, J., et al., "Implantable Glucose Sensors: Choosing the Appropriate Sensing Strategy", Biosensors, vol. 3, 1987/88, pp. 335-346.

Pickup, J., et al., "In Vivo Molecular Sensing in Diabetes Mellitus: An Implantable Glucose Sensor with Direct Electron Transfer", Diabetologia, vol. 32, 1989, pp. 213-217.

Pishko, M. V., et al., "Amperometric Glucose Microelectrodes Prepared Through Immobilization of Glucose Oxidase in Redox Hydrogels", Analytical Chemistry, vol. 63, No. 20, 1991, pp. 2268-2272.

Quinn, C. P., et al., "Kinetics of Glucose Delivery to Subcutaneous Tissue in Rats Measured with 0.3-mm Amperometric Microsensors", The American Physiological Society, 1995, E155-E161.

Rana, B. S., et al., "Relation of QT Interval Dispersion to the Number of Different Cardiac Abnormalities in Diabetes Mellitus", The American Journal of Cardiology, vol. 90, 2002, pp. 483-487.

Robinson, R. T. C. E., et al. "Changes in cardiac repolarization during clinical episodes of nocturnal hypoglycaemia in adults with Type 1 diabetes," Diabetologia, vol. 47, 2004, pp. 312-315.

Rodriguez, N., et al., "Flexible Communication and Control Protocol for Injectable Neuromuscular Interfaces", IEEE Transactions on Biomedical Circuits and Systems, vol. 1, No. 1, 2007, pp. 19-27.

(56) References Cited

OTHER PUBLICATIONS

Roe, J. N., et al., "Bloodless Glucose Measurements", *Critical Review in Therapeutic Drug Carrier Systems*, vol. 15, Issue 3, 1998, pp. 199-241.
Sakakida, M., et al., "Development of Ferrocene-Mediated Needle-Type Glucose Sensor as a Measure of True Subcutaneous Tissue Glucose Concentrations", *Artificial Organs Today*, vol. 2, No. 2, 1992, pp. 145-158.
Sakakida, M., et al., "Ferrocene-Mediated Needle-Type Glucose Sensor Covered with Newly Designed Biocompatible Membrane", *Sensors and Actuators B*, vol. 13-14, 1993, pp. 319-322.
Salehi, C., et al., "A Telemetry-Instrumentation System for Long-Term Implantable Glucose and Oxygen Sensors", *Analytical Letters*, vol. 29, No. 13, 1996, pp. 2289-2308.
Schmidtke, D. W., et al., "Measurement and Modeling of the Transient Difference Between Blood and Subcutaneous Glucose Concentrations in the Rat After Injection of Insulin", *Proceedings of the National Academy of Sciences*, vol. 95, 1998, pp. 294-299.
Shaw, G. W., et al., "In Vitro Testing of a Simply Constructed, Highly Stable Glucose Sensor Suitable for Implantation in Diabetic Patients", *Biosensors & Bioelectronics*, vol. 6, 1991, pp. 401-406.
Shichiri, M., et al., "Glycaemic Control in Pancreatectomized Dogs with a Wearable Artificial Endocrine Pancreas", *Diabetologia*, vol. 24, 1983, pp. 179-184.
Shichiri, M., et al., "In Vivo Characteristics of Needle-Type Glucose Sensor—Measurements of Subcutaneous Glucose Concentrations in Human Volunteers", *Hormone and Metabolic Research Supplement Series*, vol. 20, 1988, pp. 17-20.
Shichiri, M., et al., "Membrane Design for Extending the Long-Life of an Implantable Glucose Sensor", *Diabetes Nutrition and Metabolism*, vol. 2, 1989, pp. 309-313.
Shichiri, M., et al., "Needle-type Glucose Sensor for Wearable Artificial Endocrine Pancreas", *Implantable Sensors for Closed-Loop Prosthetic Systems*, Chapter 15, 1985, pp. 197-210.
Shichiri, M., et al., "Telemetry Glucose Monitoring Device With Needle-Type Glucose Sensor: A Useful Tool for Blood Glucose Monitoring in Diabetic Individuals", *Diabetes Care*, vol. 9, No. 3, 1986, pp. 298-301.
Shichiri, M., et al., "Wearable Artificial Endocrine Pancreas With Needle-Type Glucose Sensor", *The Lancet*, 1982, pp. 1129-1131.
Shults, M. C., et al., "A Telemetry-Instrumentation System for Monitoring Multiple Subcutaneously Implanted Glucose Sensors", *IEEE Transactions on Biomedical Engineering*, vol. 41, No. 10, 1994, pp. 937-942.
Steinhaus, B. M., et al., "The Information Content of the Cardiac Electrogram at the Stimulus Site," Annual International Conference of the IEEE Engineering in Medicine and Biology Society, vol. 12, No. 2, 1990, pp. 0607-0609.
Sternberg, R., et al., "Study and Development of Multilayer Needle-Type Enzyme-Based Glucose Microsensors", *Biosensors*, vol. 4, 1988, pp. 27-40.
Thompson, M., et al., "In Vivo Probes: Problems and Perspectives", *Clinical Biochemistry*, vol. 19, 1986, pp. 255-261.
Turner, A., et al., "Diabetes Mellitus: Biosensors for Research and Management", *Biosensors*, vol. 1, 1985, pp. 85-115.
Updike, S. J., et al., "Principles of Long-Term Fully Implanted Sensors with Emphasis on Radiotelemetric Monitoring of Blood Glucose from Inside a Subcutaneous Foreign Body Capsule (FBC)", *Biosensors in the Body: Continuous in vivo Monitoring*, Chapter 4, 1997, pp. 117-137.
Velho, G., et al., "Strategies for Calibrating a Subcutaneous Glucose Sensor", *Biomedica Biochimica Acta*, vol. 48, 1989, pp. 957-964.
Whipple, G., "Low Residual Noise Speech Enhancement Utilizing Time-Frequency", Proceedings of the International Conference on Acoustics, Speech, and Signal Processing, vol. 19, 1994, pp. I5-I8.
Wilson, G. S., et al., "Progress Toward the Development of an Implantable Sensor for Glucose", *Clinical Chemistry*, vol. 38, No. 9, 1992, pp. 1613-1617.
Wolfe, P. J., et al., "Interpolation of Missing Data Values for Audio Signal Restoration Using a Gabor Regression Model", 2005 IEEE International Conference on Acoustics, Speech, and Signal Processing, vol. 5, 2005, pp. 517-520.

\* cited by examiner

INSULIN DELIVERY APPARATUSES CAPABLE OF BLUETOOTH DATA TRANSMISSION

RELATED APPLICATIONS

The present application is a continuation of U.S. patent application Ser. No. 12/242,799, filed Sep. 30, 2008, which is a continuation in part of U.S. patent application Ser. No. 12/024,082, filed Jan. 31, 2008, which claims priority to U.S. Provisional Appl. No. 61/015,185, filed Dec. 19, 2007, the disclosure of each of which are incorporated herein by reference for all purposes.

BACKGROUND

Analyte, e.g., glucose, monitoring systems including continuous and discrete monitoring systems generally include a small, lightweight battery powered and microprocessor controlled system which is configured to detect signals proportional to the corresponding measured glucose levels using an electrometer, and radio frequency (RF) signals to transmit the collected data. One aspect of certain analyte monitoring systems include a transcutaneous or subcutaneous analyte sensor configuration which is, for example, partially mounted on the skin of a subject whose analyte level is to be monitored. The sensor cell may use a two or three-electrode (work, reference and counter electrodes) configuration driven by a controlled potential (potentiostat) analog circuit connected through a contact system.

With increasing use of pump therapy for Type 1 diabetic patients, young and old alike, the importance of controlling the infusion device such as external infusion pumps is evident. Indeed, presently available external infusion devices typically include an input mechanism such as buttons through which the patient may program and control the infusion device. Such infusion devices also typically include a user interface such as a display which is configured to display information relevant to the patient's infusion progress, status of the various components of the infusion device, as well as other programmable information such as patient specific basal profiles.

In the course of using the analyte monitoring system and the infusion device, data associated with a patient's physiological condition such as monitored analyte levels, insulin dosage information, for example, may be stored and processed. As the complexity of these systems and devices increase, so do the amount of data and information associated with the system/device.

SUMMARY

In accordance with the various embodiments of the present disclosure, there are provided method system including displaying a first representation of a medication treatment parameter profile, displaying a first representation of a physiological profile associated with the medication treatment parameter profile, detecting a modification to a segment of the medication treatment parameter profile, displaying a modified representation of the medication treatment parameter profile and the physiological profile based on the detected modification to the segment of the medication treatment parameter profile, modifying an attribute of the first representation of the medication treatment parameter profile, and modifying an attribute of the first representation of the physiological profile are provided.

These and other objects, features and advantages of the present disclosure will become more fully apparent from the following detailed description of the embodiments, the appended claims and the accompanying drawings.

DETAILED DESCRIPTION

Figure 1:
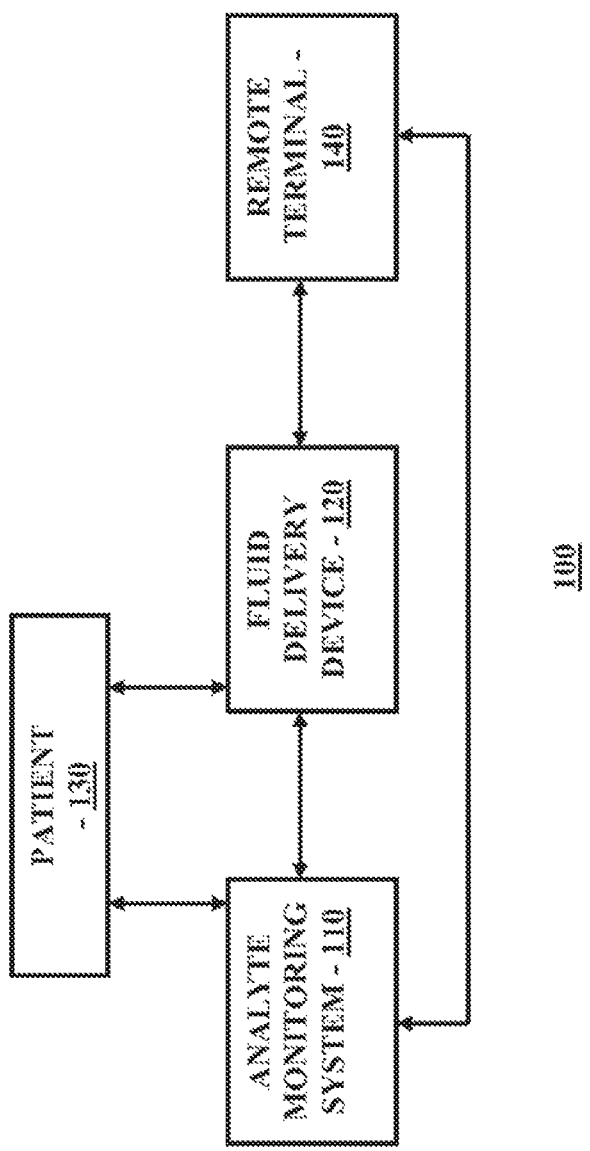
FIG. 1 is a block diagram illustrating a therapy management system for practicing one embodiment of the present disclosure.

FIG. 1 is a block diagram illustrating an insulin therapy management system for practicing one embodiment of the present disclosure. Referring to FIG. 1, the therapy management system 100 includes an analyte monitoring system 110 operatively coupled to a fluid delivery device 120, which may be in turn, operatively coupled to a remote terminal 140. As shown the Figure, the analyte monitoring system 110 is, in one embodiment, coupled to the patient 130 so as to monitor or measure the analyte levels of the patient. Moreover, the fluid delivery device 120 is coupled to the patient using, for example, and infusion set and tubing connected to a cannula (not shown) that is placed transcutaneously through the skin of the patient so as to infuse medication such as, for example, insulin, to the patient.

Referring to FIG. 1, in one embodiment, the analyte monitoring system 110 may include one or more analyte sensors subcutaneously positioned such that at least a portion of the analyte sensors are maintained in fluid contact with the patient's analytes. The analyte sensors may include, but not limited to, short term subcutaneous analyte sensors or transdermal analyte sensors, for example, which are configured to detect analyte levels of a patient over a predetermined time period, and after which, a replacement of the sensors is necessary.

The one or more analyte sensors of the analyte monitoring system 110 is coupled to a respective one or more of a data transmitter unit which is configured to receive one or more signals from the respective analyte sensors corresponding to the detected analyte levels of the patient, and to transmit the information corresponding to the detected analyte levels to a receiver device, and/or fluid delivery device 120. That is, over a communication link, the transmitter units may be configured to transmit data associated with the detected analyte levels periodically, and/or intermittently and repeatedly to one or more other devices such as the insulin delivery device and/or the remote terminal 140 for further data processing and analysis.

The transmitter units of the analyte monitoring system 110 may in one embodiment configured to transmit the analyte related data substantially in real time to the fluid delivery device 120 and/or the remote terminal 140 after receiving it from the corresponding analyte sensors such that the analyte level, such as the glucose level of the patient 130 may be monitored in real time. In one aspect, the analyte levels of the patient may be obtained using one or more of a discrete blood glucose testing devices such as blood glucose meters, or continuous analyte monitoring systems such as continuous glucose monitoring systems.

Additional analytes that may be monitored, determined or detected by the analyte monitoring system 110 include, for example, acetyl choline, amylase, bilirubin, cholesterol, chorionic gonadotropin, creatine kinase (e.g., CK-MB), creatine, DNA, fructosamine, glucose, glutamine, growth hormones, hormones, ketones, lactate, peroxide, prostate-specific antigen, prothrombin, RNA, thyroid stimulating hormone, and troponin. The concentration of drugs, such as, for example, antibiotics (e.g., gentamicin, vancomycin, and the like), digitoxin, digoxin, drugs of abuse, theophylline, and warfarin, may also be determined.

Moreover, within the scope of the present disclosure, the transmitter units of the analyte monitoring system 110 may be configured to directly communicate with one or more of the remote terminal 140 or the fluid delivery device 120. Furthermore, within the scope of the present disclosure, additional devices may be provided for communication in the analyte monitoring system 110 including additional receiver/data processing units, and/or remote terminals, such as a physician's terminal and/or a bedside terminal in a hospital environment, for example. In addition, within the scope of the present disclosure, one or more of the analyte monitoring system 110, the fluid delivery device 120 and the remote terminal 140 may be configured to communicate over a wireless data communication link such as, but not limited to, RF communication link, Bluetooth® communication link, infrared communication link, or any other type of suitable wireless communication connection between two or more electronic devices, which may further be unidirectional or bi-directional communication between the two or more devices. Alternatively, the data communication link may include wired cable connection such as, for example, but not limited to, RS232 connection, USB connection, or serial cable connection.

Referring back to FIG. 1, in one embodiment, the analyte monitoring system 110 includes a strip port configured to receive a test strip for capillary blood glucose testing. In one aspect, the glucose level measured using the test strip may in addition, be configured to provide periodic calibration of the analyte sensors of the analyte monitoring system 110 to assure and improve the accuracy of the analyte levels detected by the analyte sensors.

Exemplary analyte systems that may be employed are described in, for example, U.S. Pat. Nos. 6,134,461, 6,175,752, 6,121,611, 6,560,471, 6,746,582, and elsewhere, the disclosures of which are herein incorporated by reference.

Referring again to FIG. 1, the fluid delivery device 120 may include in one embodiment, but not limited to, an external infusion device such as an external insulin infusion pump, an implantable pump, a pen-type insulin injector device, an on-body patch pump, an inhalable infusion device for nasal insulin delivery, or any other type of suitable delivery system. In addition, the remote terminal 140 in one embodiment may include for example, a desktop computer terminal, a data communication enabled kiosk, a laptop computer, a handheld computing device such as a personal digital assistant (PDAs), or a data communication enabled mobile telephone.

Figure 2:
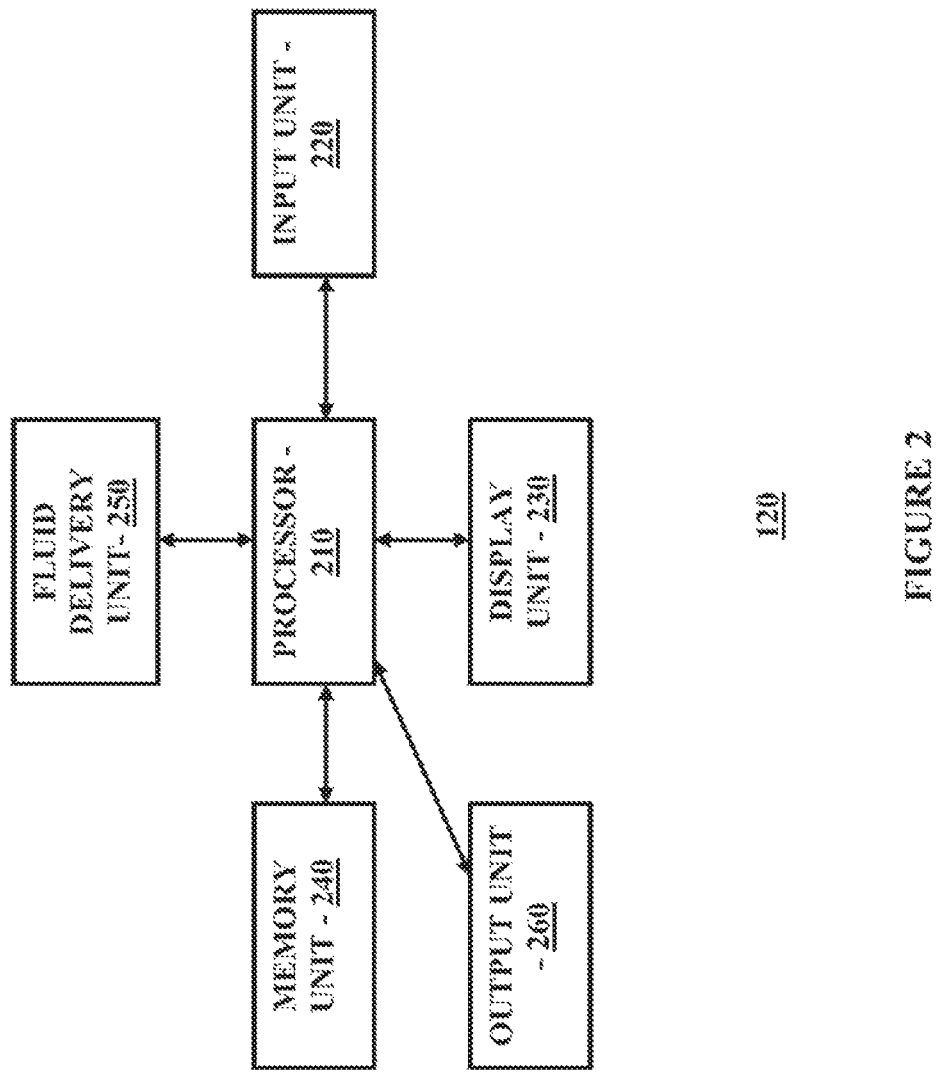
FIG. 2 is a block diagram of a fluid delivery device of FIG. 1 in one embodiment of the present disclosure.

FIG. 2 is a block diagram of an insulin delivery device of FIG. 1 in one embodiment of the present disclosure. Referring to FIG. 2, the fluid delivery device 120 in one embodiment includes a processor 210 operatively coupled to a memory unit 240, an input unit 220, a display unit 230, an output unit 260, and a fluid delivery unit 250. In one embodiment, the processor 210 includes a microprocessor that is configured to and capable of controlling the functions of the fluid delivery device 120 by controlling and/or accessing each of the various components of the fluid delivery device 120. In one embodiment, multiple processors may be provided as safety measure and to provide redundancy in case of a single processor failure. Moreover, processing capabilities may be shared between multiple processor units within the insulin delivery device 120 such that pump functions and/or control maybe performed faster and more accurately.

Referring back to FIG. 2, the input unit 220 operatively coupled to the processor 210 may include a jog dial, key pad buttons, a touch pad screen, or any other suitable input mechanism for providing input commands to the fluid delivery device 120. More specifically, in case of a jog dial input device, or a touch pad screen, for example, the patient or user of the fluid delivery device 120 will manipulate the respective jog dial or touch pad in conjunction with the display unit 230 which performs as both a data input and output units. The display unit 230 may include a touch sensitive screen, an LCD screen, or any other types of suitable display unit for the fluid delivery device 120 that is configured to display alphanumeric data as well as pictorial information such as icons associated with one or more predefined states of the fluid delivery device 120, or graphical representation of data such as trend charts and graphs associated with the insulin infusion rates, trend data of monitored glucose levels over a period of time, or textual notification to the patients.

Referring to FIG. 2, the output unit 260 operatively coupled to the processor 210 may include audible alarm including one or more tones and/or preprogrammed or programmable tunes or audio clips, or vibratory alert features having one or more pre-programmed or programmable vibratory alert levels. In one embodiment, the vibratory alert may also assist in priming the infusion tubing to minimize the potential for air or other undesirable material in the infusion tubing. Also shown in FIG. 2 is the fluid delivery unit 250 which is operatively coupled to the processor 210 and configured to deliver the insulin doses or amounts to the patient from the insulin reservoir or any other types of suitable containment for insulin to be delivered (not shown) in the fluid delivery device 120 via an infusion set coupled to a subcutaneously positioned cannula under the skin of the patient.

Referring yet again to FIG. 2, the memory unit 240 may include one or more of a random access memory (RAM), read only memory (ROM), or any other types of data storage units that is configured to store data as well as program instructions for access by the processor 210 and execution to control the fluid delivery device 120 and/or to perform data processing based on data received from the analyte monitoring system 110, the remote terminal 140, the patient 130 or any other data input source.

Figure 3:
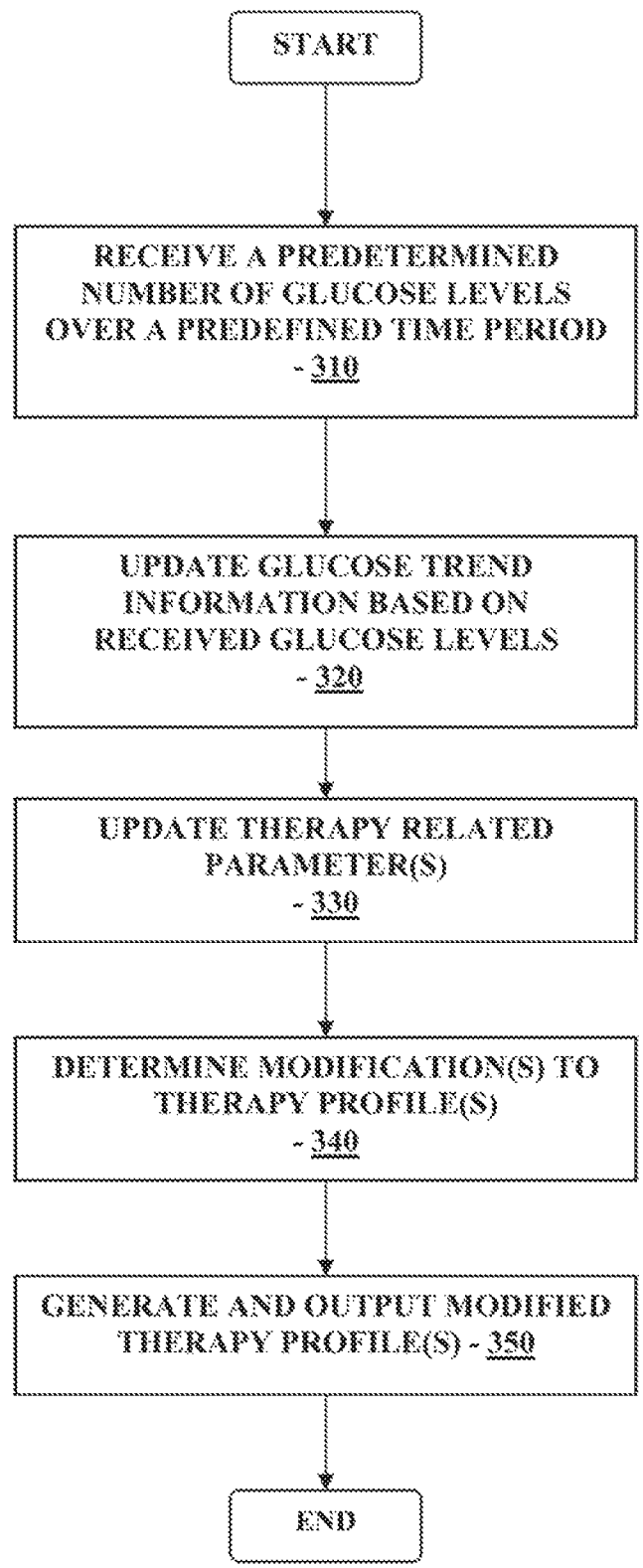
FIG. 3 is a flow chart illustrating therapy management procedure based on real time monitored analyte levels in accordance with one embodiment of the present disclosure.

FIG. 3 is a flow chart illustrating insulin therapy management procedure based on real time monitored analyte levels in accordance with one embodiment of the present disclosure. Referring to FIG. 3, in one embodiment of the present disclosure, a predetermined number of consecutive glucose levels are received or detected over a predetermined or defined time period. For example, in one embodiment, referring to FIG. 1, the monitored glucose levels of a patient is substantially continuously received or detected substantially in real time for a predetermined time period (310). In one embodiment, the predefined time period may include one or more time periods, the data within which may provide a therapeutically meaningful basis for associated data analysis.

That is, the predefined time period of the real time monitored glucose data in one embodiment may include one or more time periods sufficient to provide glucose trend information or sufficient to provide analysis of glucose levels to adjust insulin therapy on an on-going, and substantially real time basis. For example, the predefined time period in one embodiment may include one or more of a 15 minute time period, a 30 minute time period, a 45 minute time period, a one hour time period, a two hour time period and a 6 hour time period. While exemplary predefined time periods are provided herein, within the scope of the present disclosure, any suitable predefined time period may be employed as may be sufficient to be used for glucose trend determination and/or therapy related determinations (such as, for example, modification of existing basal profiles, calculation of temporary basal profile, or determination of a bolus amount).

Referring back to FIG. 3, the consecutive glucose levels received over the predefined time period in one embodiment may not be entirely consecutive due to, for example, data transmission errors and/or one or more of potential failure modes associated with data transmission or processing. As such, in one embodiment of the present disclosure, there is provided a predetermined margin of error for the received real time glucose data such that, a given number of data points associated with glucose levels which are erroneous or alternatively, not received from the glucose sensor, may be ignored or discarded.

Referring back to FIG. 3, upon receiving the predetermined number of glucose levels over a predefined time period, the glucose trend information based on the received glucose levels is updated (320). For example, in one embodiment, the glucose trend information estimating the rate of change of the glucose levels may be determined, and based upon which the projecting the level of glucose may be calculated. Indeed, in one embodiment, the glucose trend information may be configured to provide extrapolated glucose level information associated with the glucose level movement based on the real time glucose data received from the glucose sensor. That is, in one embodiment, the real time glucose levels monitored are used to determine the rate at which the glucose levels are either increasing or decreasing (or remaining substantially stable at a given level). Based on such information and over a predetermined time period, a glucose projected information may be determined.

Referring again to FIG. 3, the therapy related parameters associated with the monitored real time glucose levels are updated (330). That is, in one embodiment, one or more insulin therapy related parameters of an insulin pump such as, but not limited to, insulin on board information associated with the fluid delivery device 120 (FIG. 1), insulin sensitivity level of the patient 130 (FIG. 1), insulin to carbohydrate ratio, and insulin absorption rate. Thereafter, in one embodiment, one or more modifications to the current therapy profile are determined (340). That is, in one embodiment of the present disclosure, one or more current basal profiles, calculated bolus levels, temporary basal profiles, and/or any other suitable pre-programmed insulin delivery profiles stored in the fluid delivery device 120 (FIG. 1), for example, are retrieved and analyzed based on one or more of the received real time glucose levels, the updated glucose trend information, and the updated therapy related parameters.

Referring back to FIG. 3, after determining one or more modifications to the therapy profiles, the modified one or more therapy profiles are generated and output to the patient 130 (FIG. 1) (350) so that the patient 130 may select, store and/or ignore the one or more modified therapy profiles based on one or more of the monitored real time glucose values, updated glucose trend information, and updated therapy related parameters.

For example, in one embodiment, the patient 130 may be provided with a recommended temporary basal profile based on the monitored real time glucose levels over a predetermined time period as well as the current basal profile which is executed by the fluid delivery device 120 (FIG. 1) to deliver a predetermined level of insulin to the patient 130 (FIG. 1). Alternatively, the patient 130 in a further embodiment may be provided with one or more additional recommended actions for selection as the patient sees suitable to enhance the insulin therapy based on the real time monitored glucose levels. For example, the patient may be provided with a recommended correction bolus level based on the real time monitored glucose levels and the current basal profile in conjunction with, for example, the patient's insulin sensitivity and/or insulin on board information.

In this manner, in one embodiment of the present disclosure, based on real time monitored glucose levels, the patient may be provided with on-going, real time insulin therapy options and modifications to the pre-programmed insulin delivery basal profiles so as to improve upon the initially programmed therapy profiles based on the monitored real time glucose data.

Figure 4:
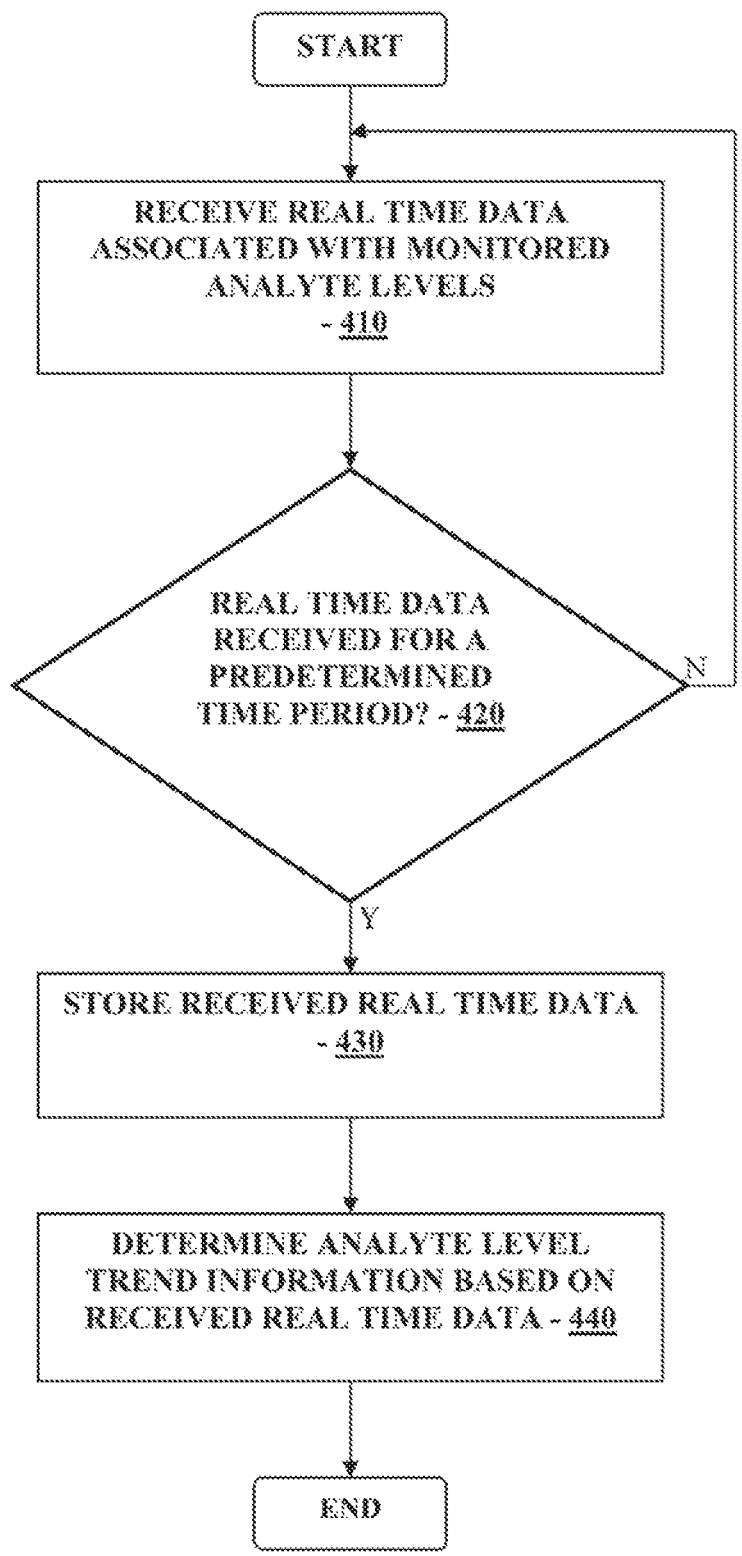
FIG. 4 is a flowchart illustrating analyte trend information updating procedure based on real time monitored analyte levels in accordance with one embodiment of the present disclosure.

FIG. 4 is a flowchart illustrating analyte trend information updating procedure based on real time monitored analyte levels in accordance with one embodiment of the present disclosure. Referring to FIG. 4, in one embodiment, real time data associated with monitored analyte levels is received (410). Thereafter it is determined whether the real time data has been received for a predetermined time period. If it is determined that the real time data has not been received for at least the predetermined time period (420), then the routine continues to receive the real time data associated with the monitored analyte levels such as glucose levels.

On the other hand, referring back to FIG. 4, if it is determined that the real time data associated with the monitored analyte levels has been received for the predetermined time period (for example, as described above in conjunction with FIG. 3), then the received real time data associated with the monitored analyte levels is stored (430). Thereafter, analyte level trend information is determined based on the received real time data associated with the monitored analyte levels (440).

For example, in one embodiment, the real time data associated with the monitored analyte levels is analyzed and an extrapolation of the data based on the rate of change of the monitored analyte levels is determined. That is, the real time data associated with the monitored analyte levels is used to determined the rate at which the monitored analyte level changed over the predetermined time period, and accordingly, a trend information is determined based on, for example, the determined rate at which the monitored analyte level changed over the predetermined time period.

In a further embodiment, the trend information based on the real time data associated with the monitored analyte levels may be dynamically modified and continuously updated based on the received real time data associated with the monitored analyte levels for one or more predetermined time periods. As such, in one embodiment, the trend information may be configured to dynamically change and be updated continuously based on the received real time data associated with the monitored analyte levels.

Figure 5:
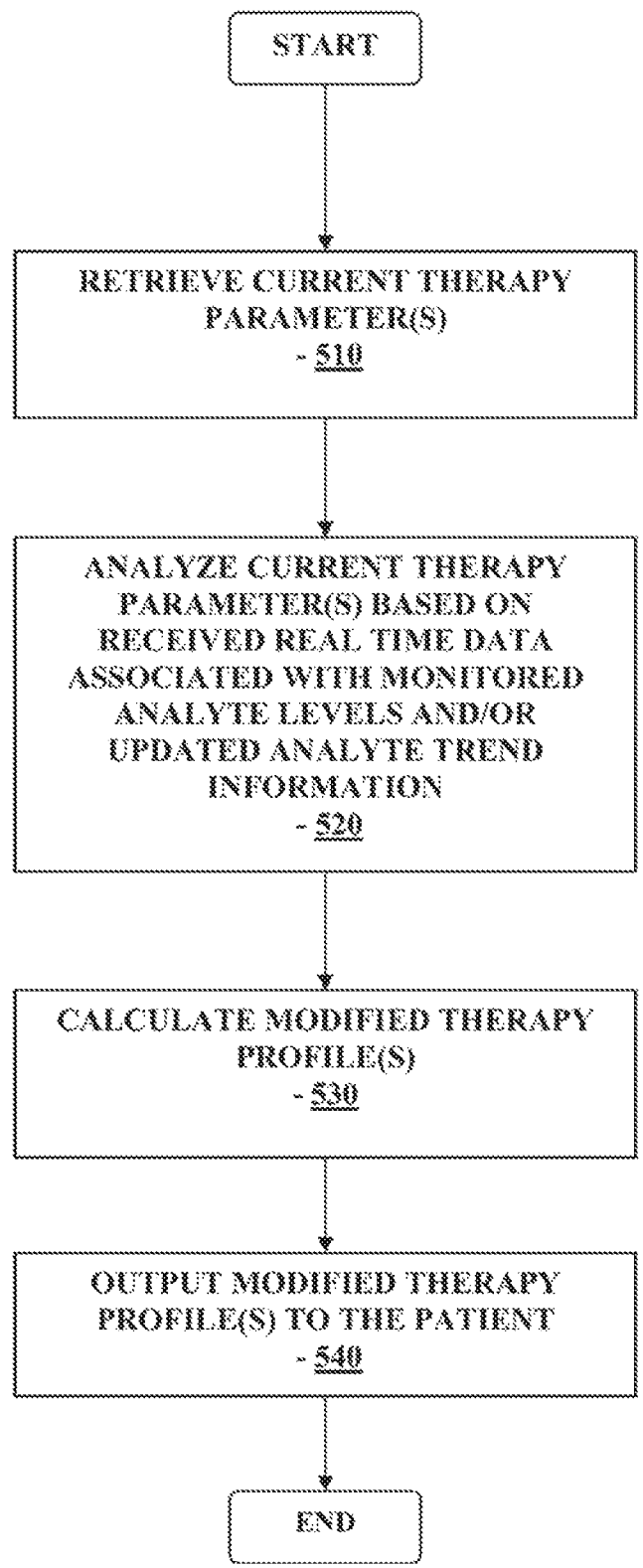
FIG. 5 is a flowchart illustrating modified therapy management procedure based on real time monitored analyte levels in accordance with one embodiment of the present disclosure.

FIG. 5 is a flowchart illustrating modified therapy management procedure based on real time monitored analyte levels in accordance with one embodiment of the present disclosure. Referring to FIG. 5, in one embodiment, the current therapy parameters are retrieved (510) and, the retrieved current therapy parameters are analyzed based on the received real time data associated with the monitored analyte levels and/or updated analyte trend information (520). For example, one or more preprogrammed basal profiles, correction bolus, carbohydrate bolus, temporary basal and associated parameters are retrieved and analyzed based on, for example, the received real time data associated with the monitored analyte levels and/or updated analyte trend information, and further, factoring in the insulin sensitivity of the patient as well as insulin on board information.

Referring to FIG. 5, based upon the analysis of the current therapy parameters, one or more modified therapy profiles are calculated (530). That is, based upon the real time glucose levels monitored by the analyte monitoring system 110 (FIG. 1), a modification or adjustment to the preprogrammed basal profiles of the fluid delivery device 120 (FIG. 1) may be determined, and the modified therapy profiles are output (540) to the patient 130 (FIG. 1). That is, the modification or adjustment to the pre-programmed basal profiles may be provided to the patient for review and/or execution to implement the recommended modification or adjustment to the pre-programmed basal profiles.

In this manner, the patient may be provided with one or more adjustments to the existing or current basal profiles or any other pre-programmed therapy profiles based on continuously monitored physiological levels of the patient such as analyte levels of the patient. Indeed, in one embodiment of the present disclosure, using continuously monitored glucose levels of the patient, modification or adjustment to the pre-programmed basal profiles may be calculated and provided to the patient for review and implementation as desired by the patient. In this manner, for example, a diabetic patient may improve the insulin therapy management and control.

Figure 6:
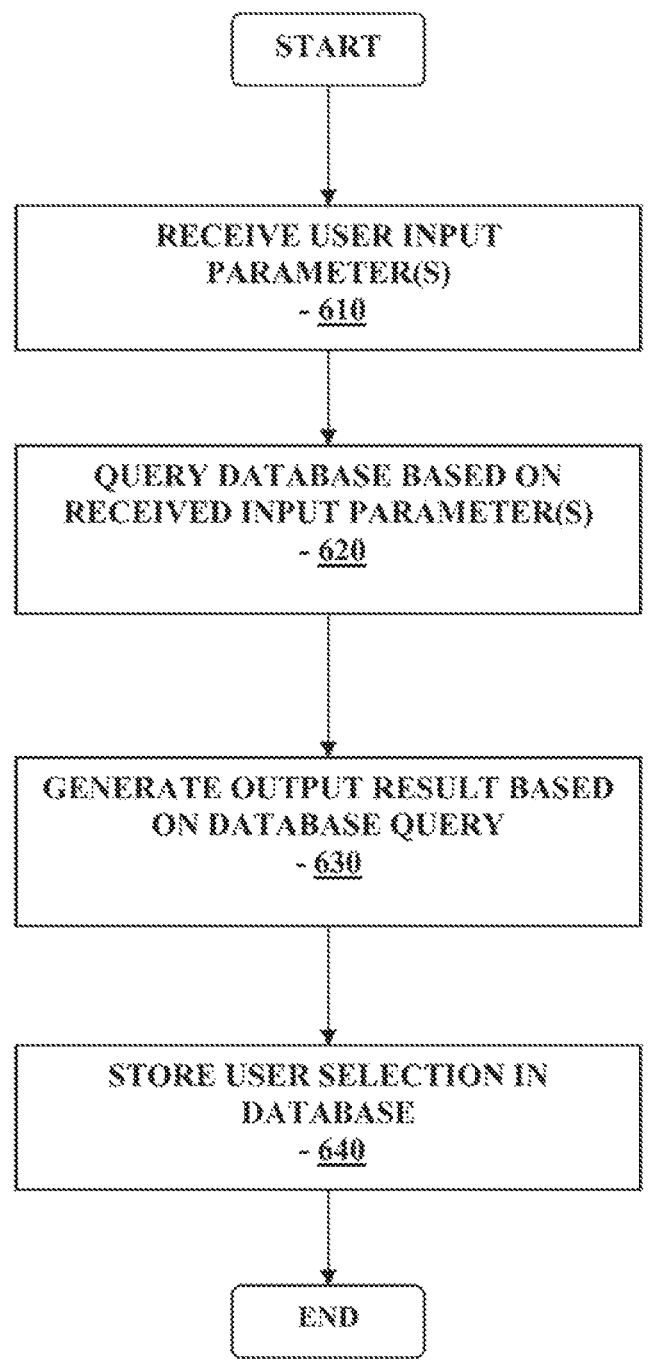
FIG. 6 is a flowchart illustrating contextual based dosage determination in accordance with one embodiment of the present disclosure.

FIG. 6 is a flowchart illustrating contextual based dosage determination in accordance with one embodiment of the present disclosure. Referring to the Figure, one or more user input parameters is received (610) such as, for example, the amount of carbohydrate to ingest, type of exercise to perform, current time of day information, or any other appropriate information that may potentially impact the determination of the suitable medication level. Based on the one or more user input parameters, one or more database is queried (620). In one embodiment, the database may be provided in the analyte monitoring system 110. Alternatively or in addition, the one or more database may be provided in the fluid delivery device 120 and/or remote terminal 140.

Referring back to FIG. 6, the database query in one embodiment may be configured to search or query for medication dosage levels that are associated with similar parameters as the received one or more user input parameters. Thereafter, the queried result is generated and provided to the user (630) which may be acted upon by the user, for example, by administering the medication dosage level based on the queried result. The user selection of the administered medication dosage level is stored in the database (640) with the associated one or more user input parameters as well as the time and date information of when the user has administered the medication dosage level.

In this manner, in one embodiment, insulin dosages and associated contextual information (e.g., user input parameters) may be stored and tracked in one or more databases. For example, a bolus amount for a diabetic patient may be determined in the manner described above using historical information without performing a mathematical calculation which takes into account variables such as sensitivity factors that vary with time and/or user's physiological conditions, and which may need to be estimated.

In particular, in one embodiment of the present disclosure, insulin dependent users may determine their appropriate insulin dosages by, for example, using historical dosage information as well as associated physiological condition information. For example, the historical data may be stored in one or more databases to allow search or query based on one or more parameters such as the user's physiological condition and other contextual information associated with each prior bolus dosage calculated and administered. In this manner, the user may be advised on the proper amount of insulin under the particular circumstances, the user may be provided with descriptive statistical information of insulin dosages under the various conditions, and the overall system may be configured to learn and customize the dosage determination for the particular user over an extended time period.

For example, in one aspect, contextual information may be stored with the insulin bolus value. The contextual data in one aspect may include one or more of blood glucose concentration, basal rate, type of insulin, exercise information, meal information, carbohydrate content estimate, insulin on board information, and any other parameters that may be used to determine the suitable or appropriate medication dosage level. Some or all of the contextual information may be provided by the user or may be received from another device or devices in the overall therapy management system such as receiving the basal rate information from the fluid delivery device 120 (FIG. 1), or receiving the blood glucose concentration from the analyte monitoring system 110 (FIG. 1).

By way of an example, a contextually determined medication dosage level in one embodiment may be provided to the user along with a suitable or appropriate notification or message to the user that after a predetermined time period since the prior administration of the medication dosage level, the blood glucose level was still above a target level. That is, the queried result providing the suitable medication dosage level based on user input or other input parameters may be accompanied by other relevant physiological condition information associated with the administration of the prior medication dosage administration. In this manner, when the user is provided with the contextually determined medication dosage level, the user is further provided with information associated with the effects of the determined medication dosage level to the user's physiological condition (for example, one hour after the administration of the particular medication dosage level determined, the user's blood glucose level changed by a given amount). Accordingly, the user may be better able to adjust or modify, as desired or needed, the contextually determined medication dosage level to the current physiological conditions.

In this manner, in one embodiment, to determine and provide the user with proper medication dosage levels, the present or current context including the patient's current physiological condition (such as current blood glucose level, current glucose trend information, insulin on board information, the current basal profile, and so on) is considered and the database is queried for one or more medication dosage levels which correlate (for example, within a predetermined range of closeness or similarity) to the one or more current contextual information associated with the user's physiological condition, among others.

Accordingly, in one embodiment, statistical determination of the suitable medication dosage based on contextual information may be determined using, one or more of mean dosage determination, using a standard deviation or other appropriate statistical analysis of the contextual information for medication dosages which the user has administered in the past. Further, in one aspect, in the case where no close match is found in the contextual query for the desired medication dosage level, the medication dosage level with the most similar contextual information may be used to interpolate an estimated medication dosage level.

In still another aspect, the database query may be configured to provide time based weighing of prior medication dosage level determinations such that, for example, more recent dosage level determination with similar contextual information may be weighed heavier than aged dosage level determination under similar conditions. For example, older or more aged bolus amounts determined may be weighed less heavily than the more recent bolus amounts. Also, over an extended period of time, in one aspect, the older or aged bolus amounts may be aged out or weighed with a value parameter that minimally impacts the current contextual based bolus determination. In this manner, in one aspect, a highly personalized and individualistic profile for medication dosage determination may be developed and stored in the database with the corresponding contextual information associated therewith.

Figure 7:
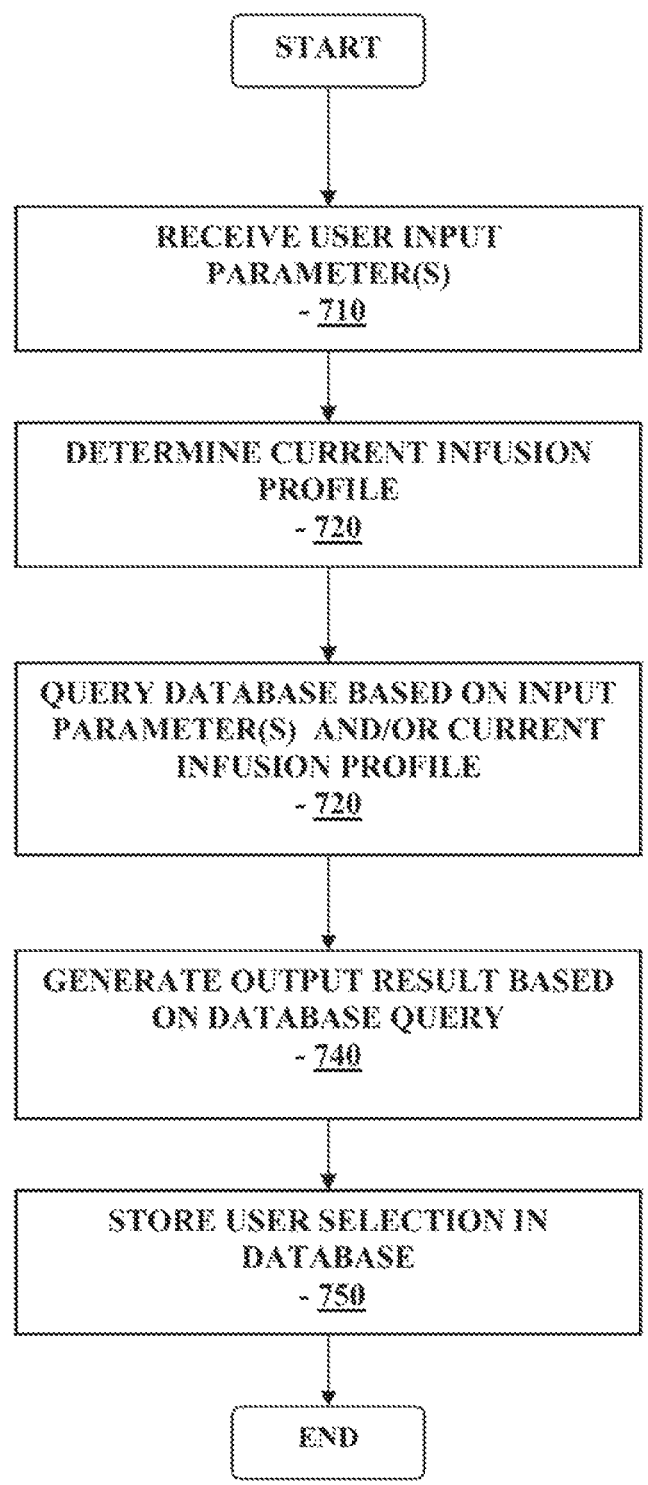
FIG. 7 is a flowchart illustrating contextual based dosage determination in accordance with one embodiment of the present disclosure.

FIG. 7 is a flowchart illustrating contextual based dosage determination in accordance with one embodiment. Referring to FIG. 7, in one aspect, when the user input parameters are received (710), the current infusion profile of the user's insulin pump is determined (720). Thereafter, the database is queried based on the input parameters and the current infusion profile (730), and which results in one or more contextually determined bolus amount associated with the input parameters and the current infusion profile (740) that is provided to the user. The determined bolus amount is then stored in the database (750) with the associated input parameters and the current infusion profile and any other contextual information associated with the determined bolus amount.

In this manner, in one aspect, in addition to the user provided input parameters, other relevant contextual information may be retrieved (for example, the current infusion profile such as basal rate from the insulin pump, the current blood glucose level and/or glucose trend information from the analyte monitoring system, and the like) prior to the database query to determine the suitable bolus amount.

As discussed above, optionally, the contextual information including the user input parameters and other relevant information may be queried to determine the suitable medication dosage level based on one or more statistical analysis such as, for example, but not limited to, descriptive statistics with the use of numerical descriptors such as mean and standard deviation, or inferential statistics including, for example, estimation or forecasting, correlation of parameters, modeling of relationships between parameters (for example, regression), as well as other modeling approaches such as time series analysis (for example, autoregressive modeling, integrated modeling and moving average modeling), data mining, and probability.

By way of a further non-limiting example, when a diabetic patient plans to administer insulin of a particular type, the patient enters contextual information such as that the patient has moderately exercised and is planning to consume a meal with a predetermined estimated carbohydrate content. The database in one embodiment may be queried for insulin dosages determined under similar circumstances in the past for the patient, and further, statistical information associated with the determined insulin dosage is provided to the user. In one aspect, the displayed statistical information associated with the determined insulin dosage may include, for example, an average amount of insulin dosage, a standard deviation or a median amount and the $25^{th}$ and the $75^{th}$ percentile values of the determined insulin dosage.

The patient may consider the displayed statistical information associated with the determined insulin dosage, and determine the most suitable or desired insulin amount based on the information received. When the patient programs the insulin pump to administer the desired insulin amount (or otherwise administer the desired insulin amount using other medication administration procedures such as injection (using a pen-type injection device or a syringe), intaking inhalable or ingestible insulin, and the like), the administered dosage level is stored in the database along with the associated contextual information and parameters.

In this manner, the database for use in the contextual based query may be continuously updated with each administration of the insulin dosage such that, each subsequent determination of appropriate insulin dosage level may be determined with more accuracy and is further customized to the physiological profile of the particular patient. Additionally, the database queried may be used for other purposes, such as, for example, but not limited to, tracking medication information, providing electronic history of the patient related medical information, and the like. Further, while the above example is provided in the context of determining an insulin level determination, within the scope of the present disclosure, other medication dosage may be determined based on the contextual based database query approaches described herein.

In a further aspect, the contextual based medication dosage query and determination may be used in conjunction with the standard or available medication dosage determination (for example, standard bolus calculation algorithms) as a supplement to provide additional information or provide a double checking ability to insure that the estimated or calculated bolus or medication dosage level is appropriate for the particular patient under the physiological condition at the time of the dosage level determination.

Within the scope of the present disclosure, the processes and routines described in conjunction with FIGS. 3-7 may be performed by the analyte monitoring system 110 (FIG. 1) and/or the fluid delivery device 120 (FIG. 1). Furthermore, the output of information associated with the context based database query for medication dosage determination may be displayed on a display unit of the receiver of the analyte monitoring system 110 (FIG. 1), or the infusion device display of the fluid delivery device 120 (FIG. 1), the display unit of the remote terminal 140 (FIG. 1), or any other suitable output device that is configured to receive the results of the database query associated with the medication dosage level determination. Alternatively, one or more such information may be output to the patient audibly as sound signal output.

In this manner, there are provided methods and system for receiving one or more parameters associated with a user physiological condition, querying a database based on the one or more parameters associated with the user physiological condition, generating a medication dosage amount based on the database query, and outputting the medication dosage amount to the user.

Optionally, statistical analysis may be performed based on the database query and factored into generating the medication dosage amount for the user.

In other aspects, there are provided methods and system for providing information associated with the direction and rate of change of analyte (e.g., glucose) levels for determination of, for example, bolus or basal rate change recommendations, for comparing expected glucose level changes to actual real time glucose level changes to update, for example, insulin sensitivity factor in an ongoing basis, and for automatically confirming the monitored glucose values within a preset time period (e.g., 30 minutes) after insulin therapy initiation to determine whether the initiated therapy is having the intended therapeutic effect.

Indeed, in accordance with the various embodiments of the present disclosure, the use of glucose trend information in insulin delivery rate determinations provides for a more accurate insulin dosing and may lead to a decrease in hypoglycemic events and improved HbA1Cs.

Accordingly, a method in one embodiment of the present disclosure includes receiving data associated with monitored analyte related levels for a predetermined time period substantially in real time, retrieving one or more therapy profiles associated with the monitored analyte related levels, generating one or more modifications to the retrieved one or more therapy profiles based on the data associated with the monitored analyte related levels.

The method may further include displaying the generated one or more modifications to the retrieved one or more therapy profiles.

In one aspect, the generated one or more modifications to the retrieved one or more therapy profiles may be displayed as one or more of an alphanumeric output display, a graphical output display, an icon display, a video output display, a color display or an illumination display.

In a further aspect, the predetermined time period may include one of a time period between 15 minutes and six hours.

The one or more therapy profiles in yet another aspect may include a basal profile, a correction bolus, a temporary basal profile, an insulin sensitivity, an insulin on board level, and an insulin absorption rate.

In still another aspect, retrieving the one or more therapy profiles associated with the monitored analyte related levels may include retrieving a current analyte rate of change information.

In yet still another aspect, generating the one or more modifications to the retrieved one or more therapy profiles may include determining a modified analyte rate of change information based on the received data associated with monitored analyte related levels.

Moreover, the method may further include generating an output alert based on the modified analyte rate of change information.

Still, the method may also include determining an analyte level projection information based on the modified analyte rate of change information.

A system for providing diabetes management in accordance with another embodiment of the present disclosure includes an interface unit, one or more processors coupled to the interface unit, memory for storing instructions which, when executed by the one or more processors, causes the one or more processors to receive data associated with monitored analyte related levels for a predetermined time period substantially in real time, retrieve one or more therapy profiles associated with the monitored analyte related levels, and generate one or more modifications to the retrieved one or more therapy profiles based on the data associated with the monitored analyte related levels.

The interface unit may include an input unit and an output unit, the input unit configured to receive the one or more analyte related data, and the output unit configured to output the one or more of the generated modifications to the retrieved one or more therapy profiles.

The interface unit and the one or more processors in a further embodiment may be operatively coupled to one or more of a housing of an infusion device or a housing of an analyte monitoring system.

The infusion device may include one of an external insulin pump, an implantable insulin pump, an on-body patch pump, a pen-type injection device, an inhalable insulin delivery system, and a transdermal insulin delivery system.

The memory in a further aspect may be configured for storing instructions which, when executed by the one or more processors, causes the one or more processors to display the generated one or more modifications to the retrieved one or more therapy profiles.

Further, the memory may be configured for storing instructions which, when executed by the one or more processors, causes the one or more processors to display the generated one or more modifications to the retrieved one or more therapy profiles as one or more of an alphanumeric output display, a graphical output display, an icon display, a video output display, a color display or an illumination display.

In one aspect, the predetermined time period may include one of a time period between 15 minutes and six hours.

The one or more therapy profiles may include a basal profile, a correction bolus, a temporary basal profile, an insulin sensitivity, an insulin on board level, and an insulin absorption rate.

In another aspect, the memory may be further configured for storing instructions which, when executed by the one or more processors, causes the one or more processors to retrieve a current analyte rate of change information.

In still another aspect, the memory may be further configured for storing instructions which, when executed by the one or more processors, causes the one or more processors to determine a modified analyte rate of change information based on the received data associated with monitored analyte related levels.

Additionally, in yet still another aspect, the memory may be further configured for storing instructions which, when executed by the one or more processors, causes the one or more processors to generate an output alert based on the modified analyte rate of change information.

Further, the memory may be further configured for storing instructions which, when executed by the one or more processors, causes the one or more processors to determine an analyte level projection information based on the modified analyte rate of change information.

A system for providing diabetes management in accordance with yet another embodiment of the present disclosure includes an analyte monitoring system configured to monitor analyte related levels of a patient substantially in real time, a medication delivery unit operatively for wirelessly receiving data associated with the monitored analyte level of the patient substantially in real time from the analyte monitoring system, a data processing unit operatively coupled to the one or more of the analyte monitoring system or the medication delivery unit, the data processing unit configured to retrieve one or more therapy profiles associated with the monitored analyte related levels, and generate one or more modifications to the retrieved one or more therapy profiles based on the data associated with the monitored analyte related levels.

In one aspect, the analyte monitoring system may be configured to wirelessly communicate with one or more of the medication delivery unit or the remote terminal such as a computer terminal (PC) or a server terminal over a radio frequency (RF) communication link, a Bluetooth® communication link, an Infrared communication link, or a wireless local area network (WLAN).

Figure 8:
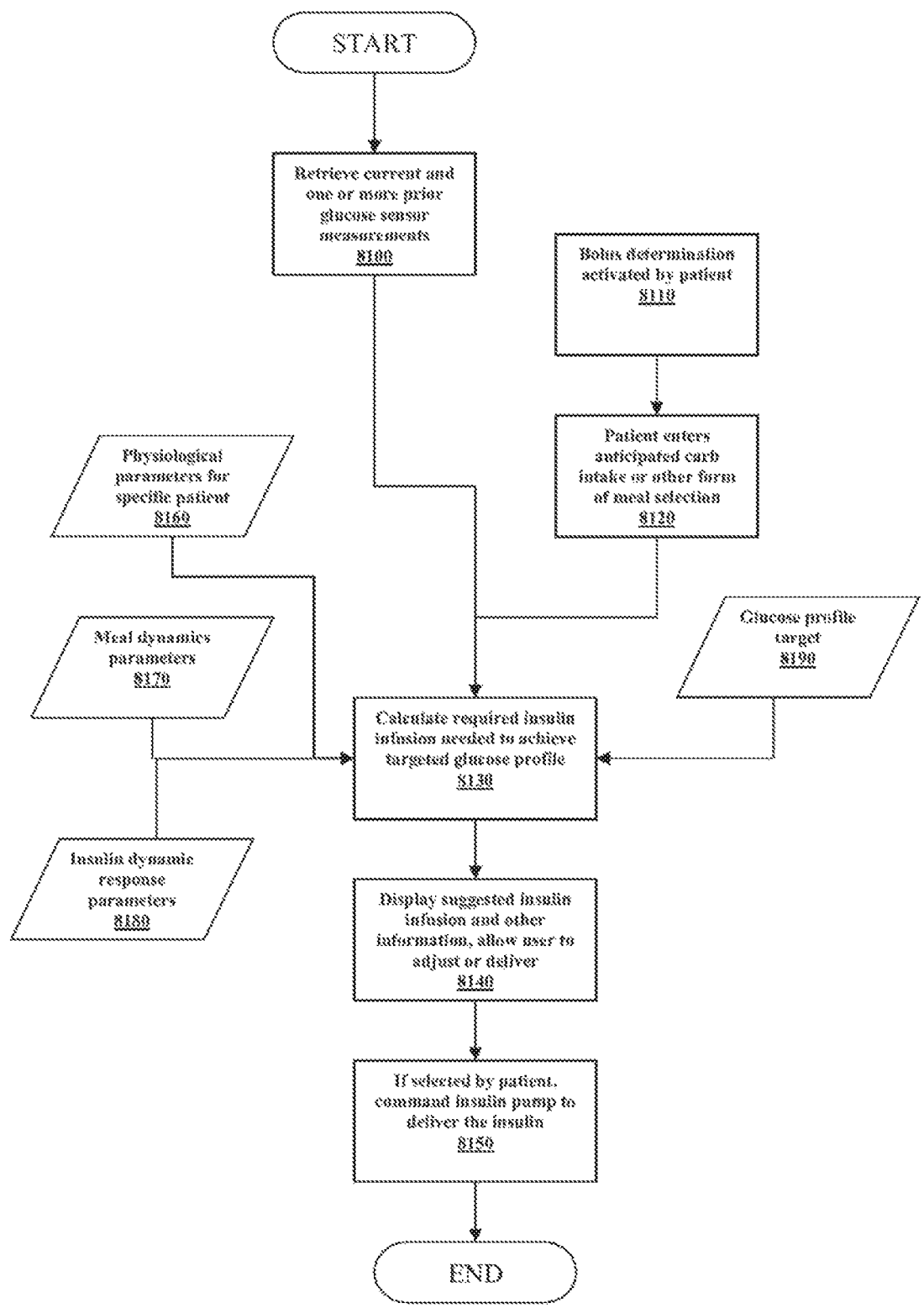
FIG. 8 illustrates dynamic medication level determination in accordance with one embodiment of the present disclosure.

FIG. 8 illustrates dynamic medication level determination in accordance with one embodiment of the present disclosure. In one aspect, the analyte monitoring system 110 (FIG. 1) may be configured to receive and store available and/or valid analyte sensor data including continuous glucose level measurement data (8100) which are indicative of the user or patient's current and past glucose levels. When the patient or the user is anticipating a meal event or any other event which may likely impact the glucose level, the patient or the user may activate or call a bolus determination function (8110) using, for example, a user interface input/output unit of the analyte monitoring system 110 (FIG. 1) or that of the fluid delivery unit 120 (FIG. 1).

Referring to FIG. 8, in one aspect the patient enters the anticipated carbohydrate intake amount, or other form of meal selection or one or more other parameters as desired for bolus determination function. With the retrieved glucose level information (8100) it is not necessary for the patient or the user to manually enter the glucose level information. In alternate embodiment, the glucose level information may be manually entered by the patient or the user. Optionally, blood glucose level may be provided to the system based on a finger stick test using a blood glucose meter device.

In one aspect, the patient or the user may enter anticipated carbohydrate information based on a pre-programmed food library stored, for example, in the analyte monitoring system 110 or the fluid delivery device 120 (FIG. 1). Such stored information may include, for example, serving size and associated carbohydrate value for different types of food, or other relevant food information related to the physiology of food update (such as fat content, for example) which may be preloaded into the analyte monitoring system 110 or the fluid delivery device 120, or alternatively, personalized by the patient or the user using custom settings and stored in the memory device of the analyte monitoring system 110 or the fluid delivery device 120.

Referring again to FIG. 8, the bolus level determination is performed in one embodiment (8110) upon patient or user activation of a user input button or component, or alternatively, in an automatic manner upon user entry of the meal information (8120). In one aspect, the bolus determination may include glucose level information from the analyte monitoring system 110 (FIG. 1) and the meal information received from the patient or the user, in conjunction with one or more of other relevant parameters described below, to propose an insulin dosage or level information to attain an anticipated blood glucose level or the future or target glucose profile (8190). In one aspect, the future or target glucose profile may be preset or alternatively, may be adjusted or modified based, for example, on the patient or user's physiological condition or profile. In one aspect, the future or target glucose profile may include a single glucose target value, or a range of desired glucose levels. Other parameters may be included in the target or future glucose profile such as, for example, maximum peak glucose value, minimum glucose value, time to achieve within 5% of the target glucose value, or other dynamic parameters. In a further aspect, the future or target glucose profile may be specified as a cost function to minimize, such as, the area defined by the accumulation in time of deviations from a target value and control sensitivity parameters, such as overshoot and undershoot. Within the scope of the present disclosure, other glucose target profiles and/or cost functions may be contemplated.

Referring back to FIG. 8, the determination of required insulin infusion to achieve the target glucose profile (8130) may include other parameters which may be predefined or patient adjustable, and/or automatically adjusted using, for example, an adaptive learning algorithm or routine that may be configured to tune the particular parameter based on a particular patient/user's physiological condition or therapy profile.

For example, one input parameter may be associated with the patient's physiological glucose response to meal intake and/or insulin intake (8160). Factors such as carbohydrate ratio and insulin sensitivity are contemplated. In one aspect, this parameter may be configured to be responsive to the various meal types or components, response time parameters and the like, such that it is updated, in real time or semi real-time, based on the change to the patient's physiological condition related to the glucose level monitored by, for example, the analyte monitoring system 110 (FIG. 1).

Another input parameter may include factors associated with the meal—meal dynamics parameters (8170). In one aspect, the meal dynamics parameters may include the timing of the meal (for example, meal event starts immediately), and the full carbohydrate intake is an impulse function—that is, the meal is substantially ingested in a short amount of time. Alternatively, factors associated with the meal dynamics parameters may be specified or programmed such as, for example, time to meal intake onset (relative to the start time of the bolus delivery), carbohydrate intake profile over time (for example, carbohydrate intake may be configured to remain substantially constant over a predetermined time period). Within the scope of the present disclosure, other elaborate intake models are contemplated.

Referring again to FIG. 8, a further input parameter may include insulin dynamic response parameters (8180) which may include physiological dynamic glucose response associated with the different types of insulin that may be delivered by, for example, fluid delivery device 120 (FIG. 1). For example, a factor associated with the insulin dynamic response parameters may include time to peak effect of the relevant insulin formulation, or a time constant associated with the glucose response which may be established by the type of insulin for delivery.

In one aspect, the calculation of the required insulin to attain the targeted glucose profile (8130) may be configured in different manners. For example, the determination may be configured as a lookup table, with input values as described above, and associated outputs of insulin profiles. In one aspect, the dynamic functional relationship that defines the physiological glucose response to the measurement inputs and parameters described above may be incorporated for determination of the desired insulin amount. The calculation or determination function may be incorporated in a regulator control algorithm that may be configured to model functional relationships and measured input values or parameters to define a control signal to drive the therapy system 100 (FIG. 1) to achieve the desired response. That is, in one aspect, the dynamic functional relationship may be defined by the physiological relationships and/or the parameter inputs. The measured input values may include the current and prior glucose values, for example, received from the analyte sensor in the analyte monitoring system 110 (FIG. 1) and the user or patient specified meal related information. The control signal discussed above may include determined or calculated insulin amount to be delivered, while the desired response includes the target or desired future glucose profile.

Referring yet again to FIG. 8, the determined insulin level, based on the calculation described above, may be displayed optionally with other relevant information, to the patient or the user (8140). In one aspect, the patient or the user may modify the determined insulin level to personalize or customize the dosage based on the user's knowledge of her own physiological conditions, for example. The patient or the user may be also provided with a function or a user input command to execute the delivery of the determined bolus amount (8150), which, upon activation, is configured to control the fluid delivery device 120 (FIG. 1) to deliver the determined amount of insulin to the patient. A further embodiment may not permit the patient modification of the determined bolus amount, and/or include automatic delivery of the determined insulin amount without patient or user intervention. In still a further embodiment, based on the monitored analyte levels of the patient, the determined insulin amount may be displayed to the user with a recommendation to defer the activation or administration of the determined insulin amount for a predetermined time period.

Figure 9:
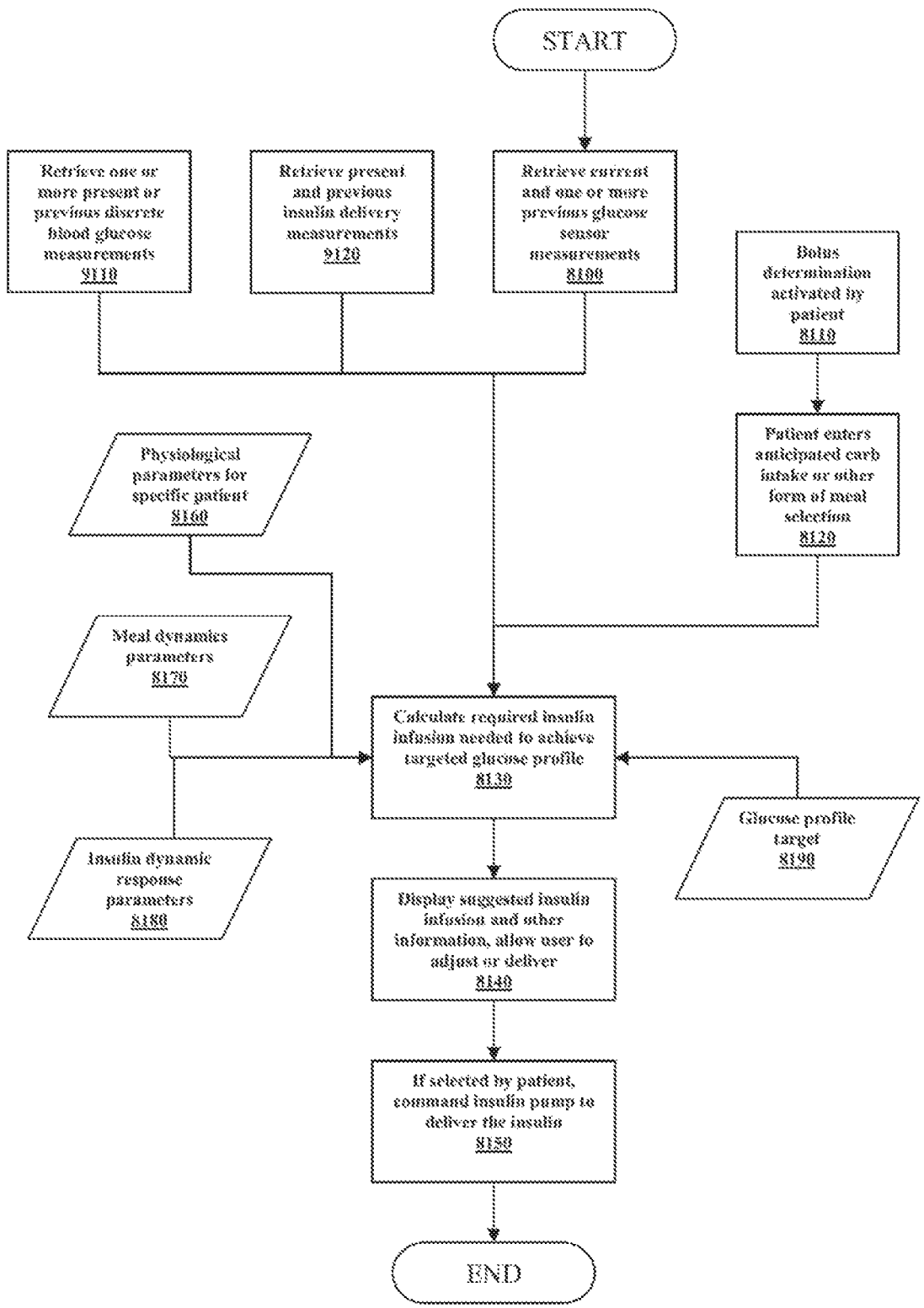
FIG. 9 illustrates dynamic medication level determination in accordance with another embodiment of the present disclosure.

FIG. 9 illustrates dynamic medication level determination in accordance with another embodiment of the present disclosure. Referring to FIG. 9, in another embodiment, the bolus determination function may include additional data from the analyte monitoring system 110 (FIG. 1), the fluid delivery device 120 (FIG. 1), and/or the remote terminal 140 (FIG. 1). More specifically, in one aspect, one or more blood glucose measurement data (9110) and/or the current and previous insulin administration profiles or measurements (9120) may be retrieved from one or more of the analyte monitoring system 110, the fluid delivery device 120 and/or the remote terminal 140 of the therapy management system 100 (FIG. 1).

Each of the measured or monitoring data or information such as analyte sensor data, blood glucose measurements, insulin delivery information and the like, in one aspect, are associated with a time stamp and stored in the one or more memory devices of the therapy management system 100. Thus, this information may be retrieved for therapy related determination such as bolus dosage calculation, or further data analysis for therapy management for the patient.

In accordance with aspects of the present disclosure, there are various sources of glucose level determination (in some instances redundant), used in several different ways. For example, Kalman filter may be used to provide for multiple measurements of the same measurable quantity. The Kalman filter may be configured to use the input parameters and/or factors discussed above, to generate an optimal estimate of the measured quantity. In a further configuration, the Kalman filter may be configured to validate the analyte sensor data based on the blood glucose measurements, where one or more sensor data may be disqualified if the blood glucose data in the relevant time period deviates from the analyte sensor data by a predetermined level or threshold. Alternatively, the blood glucose measurements may be used to validate the analyte sensor data or otherwise, calibrate the sensor data.

In a further aspect, the bolus determination function may include a subroutine to indicate unacceptable error in one or more measured data values. For example, in the case where analyte sensor data include attenuations (or "dropouts"), in one aspect, a retrospective analysis may be performed to detect the incidence of such signal attenuation in the analyte sensor data, and upon detection, the bolus determination function may be configured to ignore or invalidate this portion of data in its calculation of the desired insulin amount. Additionally, the therapy management system 100 may be configured such that insulin dosage or level calculation or determination includes a validation of analyte sensor data and/or verification of the sensor data for use in conjunction with the bolus determination (or any other therapy related determination) function.

In a further aspect of the present disclosure, various metrics may be determined to summarize a patient's monitored glucose data and related information such as, but not limited to, insulin delivery data, exercise events, meal events, and the like, to provide indication of the degree or status of the management and control of the patient's diabetic conditions. Metrics may be determined or calculated for a specified period of time (up to current time), and include, but not limited to, average glucose level, standard deviation, percentage above/below a target threshold, number of low glucose alarms, for example. The metrics may be based on elapsed time, for example, since the time of the patient's last reset of particular metric(s), or based on a fixed time period prior to the current time. Such determined metrics may be visually or otherwise provided to the patient in an easy to understand and navigate manner to provide the progression of the therapy management to the user and also, with the option to adjust or modify the related settings or parameters.

In one aspect, the output of the determined metrics may be presented to the user on the output unit 260 (FIG. 2) of the fluid delivery device 120 (FIG. 1), a display device on the analyte monitoring system 110, a user interface, and/or an output device coupled to the remote terminal 140 (FIG. 1). In one aspect, the metrics may be configured to provide a visual indication, tactile indication, audible indication or in other manner in which the patient or the user of the therapy management system 100 (FIG. 1) is informed of the condition or status related to the therapy management. Each metric may be user configurable to allow the patient or the user to obtain additional information related to the metric and associated physiological condition or the operational state of the devices used in the therapy management system 100. The metric may be associated with indicators or readings other than glucose, such as, for example, the amount and/or time of insulin delivered, percentage of bolus amount as compared to the total insulin delivered, carbohydrate intake, alarm events, analyte sensor replacement time periods, and in one aspect, the user or the patient may associate one or more alarms, alerts or notification with one or more of the metrics as may be desired.

Figure 10:
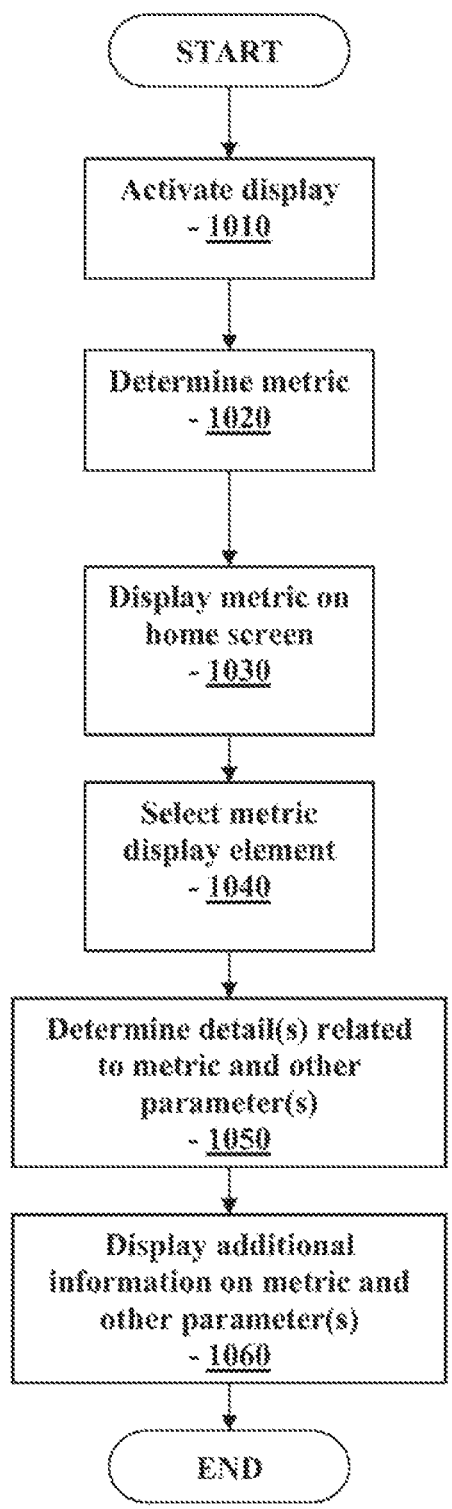
FIG. 10 illustrates metric analysis in accordance with one embodiment of the present disclosure.

FIG. 10 illustrates metric analysis in accordance with one embodiment of the present disclosure. Referring to FIG. 10, upon activation of the display (1010) or a user interface device coupled to the one or more devices in the therapy management system 100 (FIG. 1), the desired metric information is determined (1020), for example, based on the current available information (e.g., the insulin delivery information for the past 2 hours). After determining the metric information, the determined metric information is displayed on the main or home screen or display of the user interface device (1030).

In one aspect, as shown in FIG. 10, the displayed metric may be selected, for example, based on user activation on a display element (1040). Upon detecting the selection of the particular metric displayed, additional detail information related to the selected metric as well as, optionally, other related information are determined or calculated (1050), and thereafter provided to the user or the patient on the user interface device (1060). In this manner, in one aspect, the user interface device may be configured with layered menu hierarchy architecture for providing current information associated with a particular metric or condition associated with the therapy management system. The patient or the user may configure the user interface device to display or output the desired metrics at a customizable level of detail based on the particular patient or the user's settings. While the above description is provided in conjunction with a visual indication on the user interface device, within the scope of the present invention, other output indications may be similarly configured and used, such as audible notifications, vibratory or tactile notifications, and the like, each of which may be similarly configured by the patient or the user.

Within the scope of the present disclosure, the metrics may be provided on other devices that may be configured to receive periodic updates from the user interface device of the therapy management system. In one aspect, such other devices may include mobile telephones, personal digital assistants, pager devices, Blackberry® devices, remote care giver devices, remote health monitoring system or device, which may be configured for communication with the therapy management system 100, and that may be configured to process the data from the therapy management system 100 to determine and output the metrics. This may be based on real time or substantially real time data communication with the therapy management system 100. In other aspects, the therapy management system 100 may be configured to process and determine the various metrics, and transmit the determined metrics to the other devices asynchronously, or based on a polling request received from the other devices by the therapy management system 100.

The user interface device in the therapy management system 100 may be configurable such that the patient or the user may customize which metric they would like to view on the home screen (in the case of visual indication device such as a display unit). Moreover, other parameters associated with the metrics determination, such as, for example, but not limited to, the relevant time period for the particular metric, the number of metrics to be output or displayed on a screen, and the like may be configured by the user or the patient.

In a further aspect, the metric determination processing may include routines to account for device anomalies (for example, in the therapy management system 100), such as early signal attenuation (ESA) or dropouts, analyte sensor calibration, or other physiological conditions associated with the patient as well as operational condition of the devices in the therapy management system such as the fluid delivery device 120 (FIG. 1) or the analyte monitoring system 110 (FIG. 1).

Some glucose measurement anomalies may not be detected in real time and thus require retrospective detection and/or compensation. When processing a batch of current and past analyte sensor data to, for example, determine a particular metric, determine a desired bolus dosage amount, evaluate data to detect glucose control conditions, perform a data fit function to a model to execute therapy simulations, or perform any other process that may be contemplated which requires the processing of prior glucose related data, anomalies such as signal attenuation, dropouts, noise burse, calibration errors or other anomalies may be detected and/or compensated. For example, a signal dropout detector may be used to invalidate a portion of the prior glucose related data, to invalidate an entire data set, or to notify the patient or the user of the corresponding variation or uncertainly in accuracy in a predetermined one or more metrics or calculations.

Figure 11:
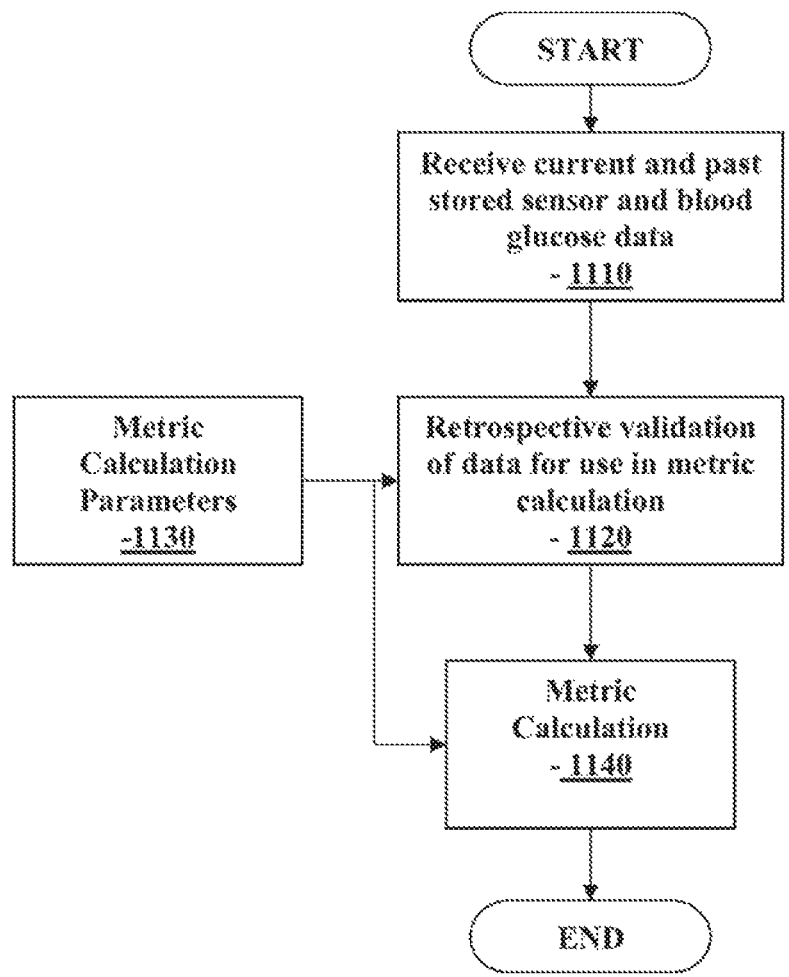
FIG. 11 illustrates metric analysis in accordance with another embodiment of the present disclosure.

For example, referring to FIG. 11 which illustrates metric analysis in accordance with another embodiment of the present disclosure, based on current and past stored sensor data and blood glucose data received (1110), retrospective validation of data used in metric calculation is performed (1120), which includes one or more metric calculation parameters (1130). Referring to FIG. 11, in one aspect, the metric calculation parameters (1130) may be used in the metric calculation (1140) which, as shown, may be performed after the data to be used in the metric calculation is retrospectively validated.

In one aspect, the metrics may be determined or recalculated after each received analyte sensor data and thereafter, displayed or provided to the user or the patient upon request, or alternatively, automatically, for example, by refreshing the display screen of the user interface device in the therapy management system 100 (FIG. 1), or otherwise providing an audible or vibratory indication to the patient or the user.

Figure 12:
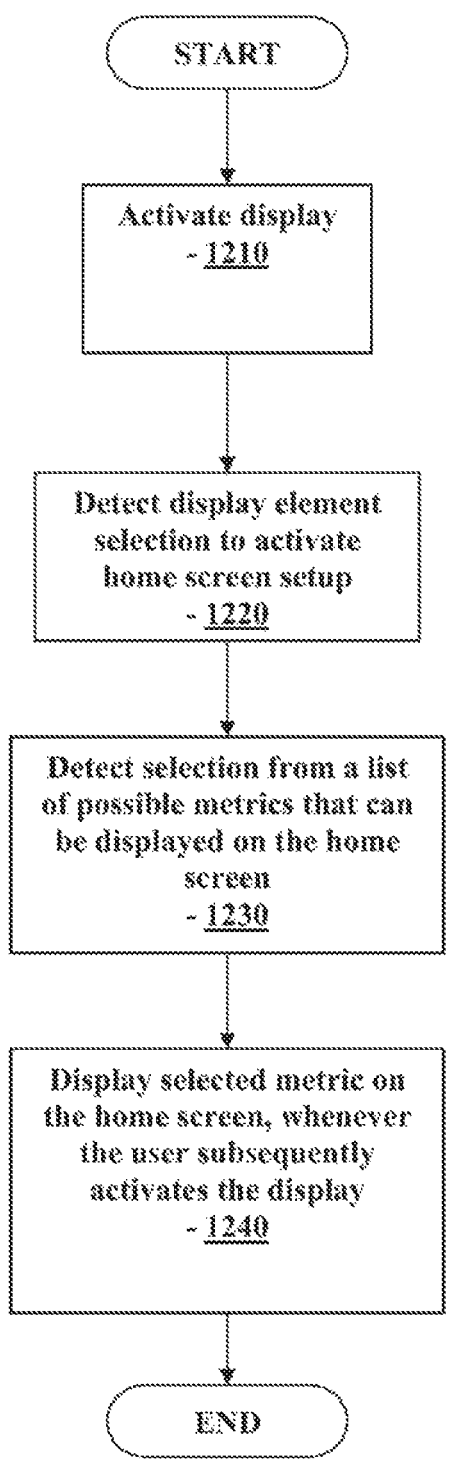
FIG. 12 is illustrates metric analysis in accordance with yet another embodiment of the present disclosure.

FIG. 12 illustrates metric analysis in accordance with yet another embodiment of the present disclosure. Referring to FIG. 12, upon detection of display activation (1210), the user interface device may be configured to activate a home screen or main menu configuration or setup function based on detected display element selection (1220). That is, in one aspect, the user or the patient may call a configuration function to customize the displayed menu associated with the display or output indication of the metrics.

Referring to FIG. 12, from the configuration menu on the user interface device, the user or patient selection of one or more metrics to be displayed or output on the main menu or home screen on the user interface device is detected (1230). After storing the user defined or selected metrics related configuration, the user interface device is configured to display or output the selected one or more metrics on the home screen or the main menu each time the user interface device is activated (1240). In this manner, in one aspect, the user or the patient may be provided with an option to display or output a particular subset of available metrics on the main display screen of the user interface device. In another aspect, the user interface device in the therapy management system 100 may be configured to include a default set of metrics to be displayed and/or updated, either in real time, or substantially in real time, or based in response to another related event such as an alarm condition, or a monitored glucose level. The system may be configured to not output any metrics.

Figure 13:
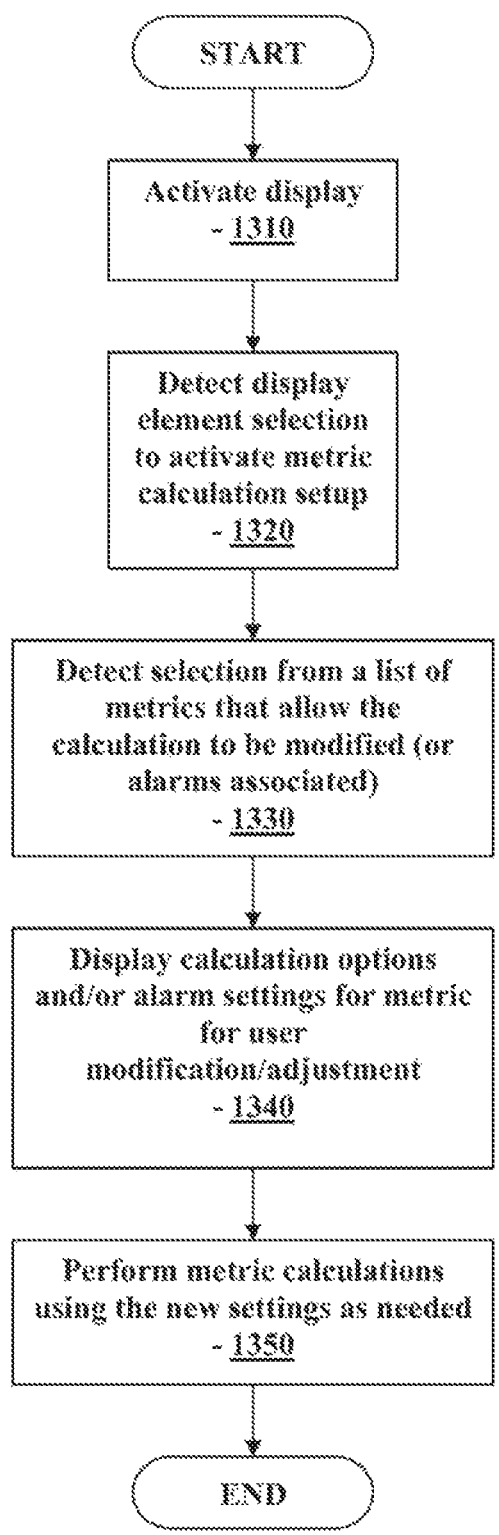
FIG. 13 illustrates metric analysis in accordance with a further embodiment of the present disclosure.

FIG. 13 illustrates metric analysis in accordance with a further embodiment of the present disclosure. Referring to FIG. 13, upon detection of the display or user interface device activation (1310), metric calculation setup function is called based on detection of a display selection to activate the same (1320), and detection of a selection from a list of metrics that allow the calculations to be modified (or alarms associated) (1330). The configuration options including metric calculation parameters, for example, are displayed (1340) in one embodiment, and the selected metric may be calculated, with one or more parameters modified or otherwise programmed, and optionally with one or more alarm conditions or settings associated with the selected metric (1350).

In this manner, the patient or the user may in one embodiment interact with the user interface device to customize or program the determination or calculation of the particular one or more metrics for display, and further, to modify the parameters associated with the calculation of the various metrics. Accordingly, in one aspect of the present disclosure, therapy related information may be configured for output to the user to, among others, provide the patient or the user of the associated physiological condition and the related therapy compliance state.

In accordance with still another aspect of the present disclosure, the therapy management system 100 (FIG. 1) may be configured to monitor potential adverse conditions related to the patient's physiological conditions. For example, a prevalence of glucose levels for a predetermined time period, pre-prandial, may be analyzed to determine if the prevalence exceeds a predefined threshold, with some consistency. Upon detection of the predefined adverse condition, the user interface device may be configured to provide a notification (visual or otherwise) to the patient or the user, and varying degrees of detailed information associated with the detected adverse condition may be provided to the patient or the user. Such notification may include text information such as, for example "Your pre-meal glucose tends to be high", or graphically by use of an arrow icon or other suitable visual indication, or a combination of text and graphics.

Adverse conditions that are not related to the monitored analyte level, such as insulin delivery data that is consistent with insulin stacking may be detected. Other examples include mean bolus event that appear to occur too late relative to the meal related glucose increases may be detected, or excessive use of temporary basal or bolus dosage or other modes of enhanced insulin delivery beyond the basal delivery profiles. Also device problems such as excessive signal dropouts from the analyte sensor may be detected and reported to the user.

In one aspect, the user interface device may be configured to customize or program the visual output indication such as icon appearance, such as enabling or disabling the icon appearance or one or more alarms associated with the detection of the adverse conditions. The notification to the user may be real time, active or passive, such that portions of the user interface device is updated to provide real time detection of the adverse conditions. Moreover, the adverse condition detection thresholds may be configured to be more or less sensitive to the triggering event, and further, parameters associated with the adverse condition detection determination may be adjusted—for example, by the time period for calculating a metric.

In a further aspect, the user interface device may provide indication of a single adverse detection condition, based on a priority list of possible adverse conditions, a list of detected adverse conditions, optionally sorted by priority, or prior detection of adverse conditions. Also, the user interface device may provide treatment recommendation related to the detected adverse condition, displayed concurrently, or options to resolve the detected adverse condition along with the detected adverse condition. In still another aspect, the notification of the detected adverse condition may be transmitted to another device, for example, that the user or the patient is carrying or using such as, for example, a mobile telephone, a pager device, a personal digital assistant, or to a remote device over a data network such as a personal computer, server terminal or the like.

In still another embodiment, some or all aspects of the adverse condition detection and analysis may be performed by a data management system, for example, by the remote terminal 140 (FIG. 1) or a server terminal coupled to the therapy management system 100. In this case, the analysis, detection and display of the adverse condition may be initiated upon the initial upload of data from the one or more analyte monitoring system 110 or the fluid delivery device 120, or both. Additionally, the adverse condition process may also account for potential measurement anomalies such as analyte sensor attenuation conditions or dropouts, or sensor calibration failures.

Figure 14:
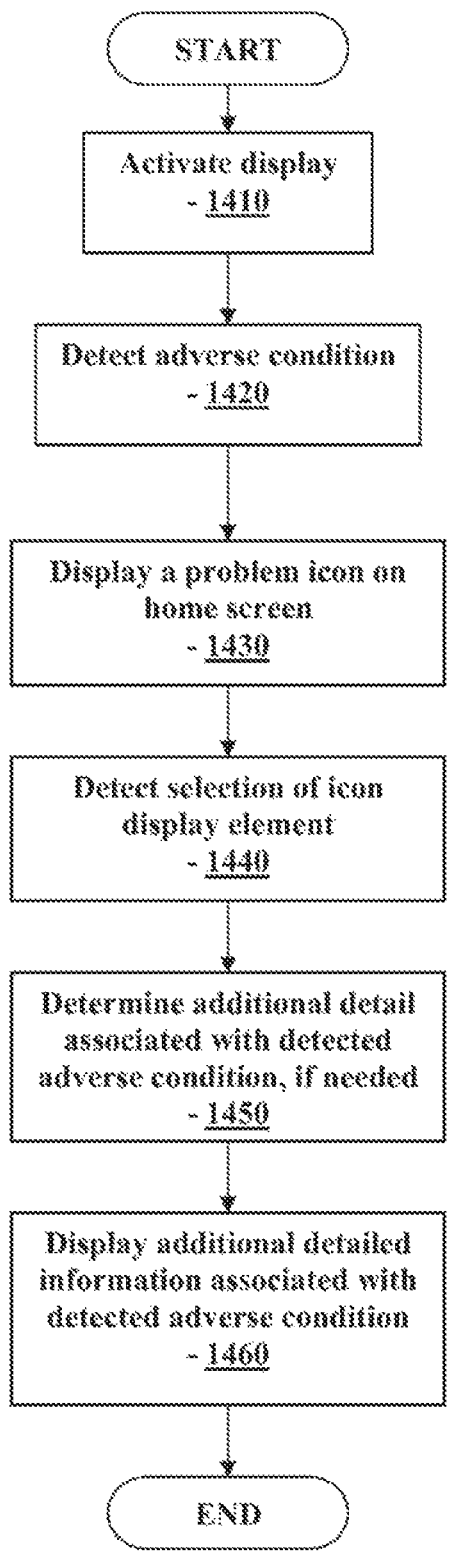
FIG. 14 illustrates condition detection or notification analysis in accordance with one embodiment of the present disclosure.

FIG. 14 illustrates condition detection or notification analysis in accordance with one embodiment of the present disclosure. Referring to FIG. 14, upon user interface device activation detection (1410) such as activation of a display device in the therapy management system 100 (FIG. 1), preprogrammed or predefined adverse condition is detected (1420), and displayed (1430) on the home screen of the user interface device using, for example, a problem icon. When the selection of the icon display element associated with the adverse condition is detected (1440), for example, indicating that the patient or the user desires additional information associated with the detected adverse condition, additional detailed information associated with the adverse condition is determined, as appropriate (1450), and thereafter, the additional detailed information is displayed to the user (1460).

Figure 15:
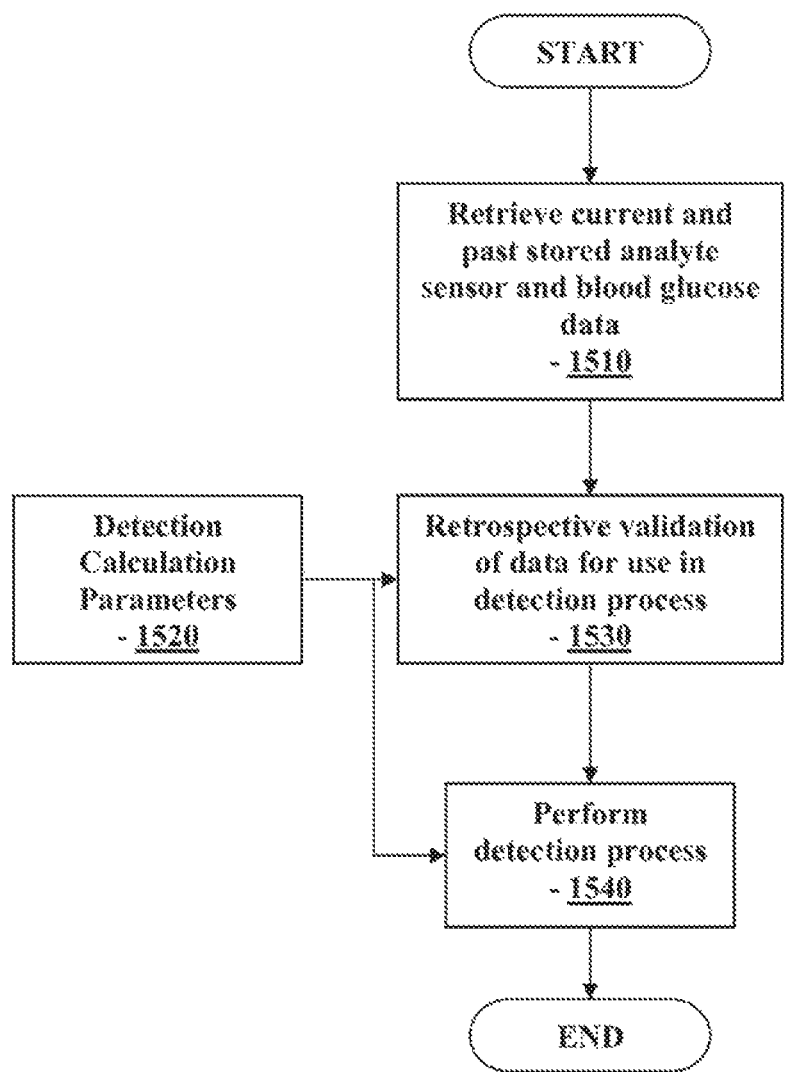
FIG. 15 illustrates condition detection or notification analysis in accordance with another embodiment of the present disclosure.

FIG. 15 illustrates condition detection or notification analysis in accordance with another embodiment of the present disclosure. Referring to FIG. 15, current and prior stored analyte sensor data and blood glucose data are retrieved (1510) and retrospective validation of the data for use in the adverse condition detection process is performed (1530), based also, at least in part, on the detection calculation parameters (1520) which may be user input or preprogrammed and stored. Thereafter, the adverse condition detection process is performed (1540), for example, the parameters associated with the programmed adverse conditions are monitored and upon detection, notified to the patient or the user.

Figure 16:
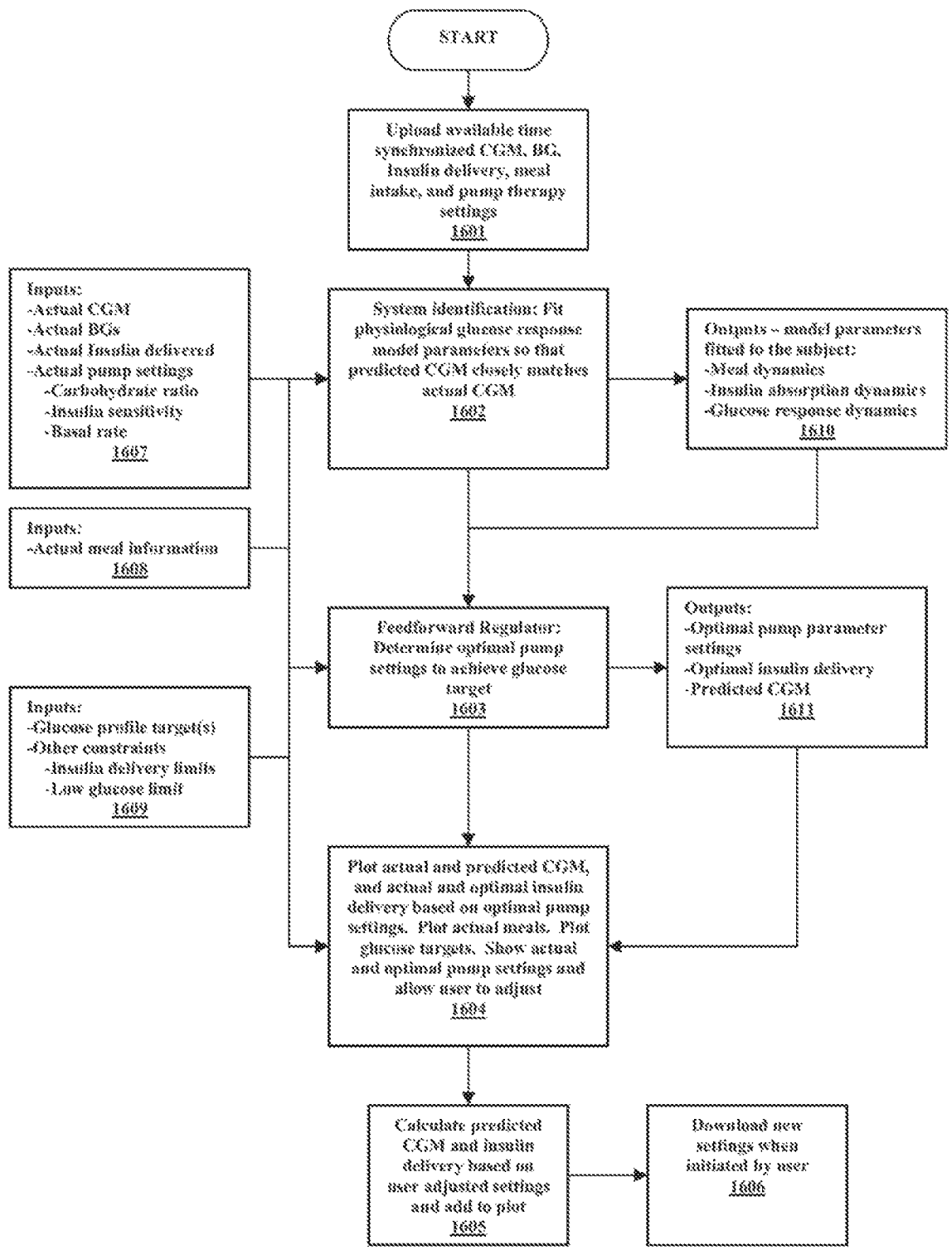
FIG. 16 illustrates therapy parameter analysis in accordance with one embodiment of the present disclosure.

In accordance with yet a further aspect of the present disclosure, therapy analysis system is provided. In one aspect, the therapy management system 100 (FIG. 1) may be used to collect and store patient related data for analysis to optimize therapy profiles and associated parameters for providing treatment to the patients. More specifically, FIG. 16 illustrates therapy parameter analysis in accordance with one embodiment of the present disclosure. As shown, data from a continuous glucose monitoring system (CGM) such as an analyte monitoring system 110 (FIG. 1) and an insulin pump such as, for example, fluid delivery device 120 (FIG. 1) are collected or stored over a predetermined time period. In addition, during this time period, meal intake information may be stored, along with other relevant data such as, exercise information, and other health related information. All data is stored with a corresponding date and time stamp and are synchronized.

After the predetermined time period, the stored data including, for example, time synchronized analyte sensor data (CGM), blood glucose (BG) data, insulin delivery information, meal intake information and pump therapy settings, among others, are uploaded to a personal computer, for example, such as the remote terminal 140 (FIG. 1) for further analysis (1601). The received data is used as input data including, for example, actual glucose data (CGM), actual blood glucose data (BG), actual insulin amount delivered, actual pump settings including carbohydrate ratio, insulin sensitivity, and basal rate, among others (1607), as well as actual meal information (1608), to perform a system identification process (1602).

More specifically, the system identification process (1602) in one embodiment is configured to fit the received input data to a generic physiological model that dynamically describes the interrelationship between the glucose levels and the delivered insulin level as well as meal intake. In this manner, in one aspect, the system identification process (1602) is configured to predict or determine glucose levels that closely matches the actual glucose level (CGM) received as one of the input parameters.

Referring to FIG. 16, as shown, the parameters of the generic physiological model are adjusted so that the model output (glucose level) closely matches the actual monitored glucose level when the measured inputs are applied (1610). That is, a newly identified model is generated based, at least in part, on meal dynamics, insulin absorption dynamics, and glucose response dynamics. Thereafter, based on the newly identified model (1610), actual meal information representing carbohydrate intake data (1608), and the glucose profile target(s) as well as any other constraints such as insulin delivery limits, low glucose limits, for example (1609), to determine the optimal pump setting to obtain the target glucose profile(s) (1603). That is, in one aspect, based on a predefined cost function such as minimizing the area about a preferred glucose level, or some other boundaries, predicted glucose levels are determined based on optimal pump therapy settings, and optimal insulin delivery information (1611).

Based on the analysis performed as described above, a report may be generated which shows model day results, with median and quartile traces, and illustrating the actual glucose levels and glucose levels predicted based on the identified model parameters, actual insulin delivery information and optimal insulin delivery information, actual mean intake information, and actual and optimal insulin therapy settings (1604). Other report types can be generated as desired. In one aspect, a physician or a treatment provider may modify one or more parameters to view a corresponding change in the predicted glucose values, for example, that may be more conservative to reduce the possibility of hypoglycemia.

Referring again to FIG. 16, a new predicted glucose and insulin delivery information based on the adjusted setting are determined (1605). The predicted glucose values and insulin delivery information are added to the plot displayed and in one aspect, configured to dynamically change, in real time, in response to the parameter adjustments. Upon determination of an acceptable therapy profile, the settings and/or parameters associated with the insulin delivery, including, for example, modified basal profiles, for the insulin pump, may be downloaded (1606) to the pump controller from the computer terminal (for example, the remote terminal 140) for execution by the insulin pump, for example, the fluid delivery device 120 (FIG. 1).

Figure 17:
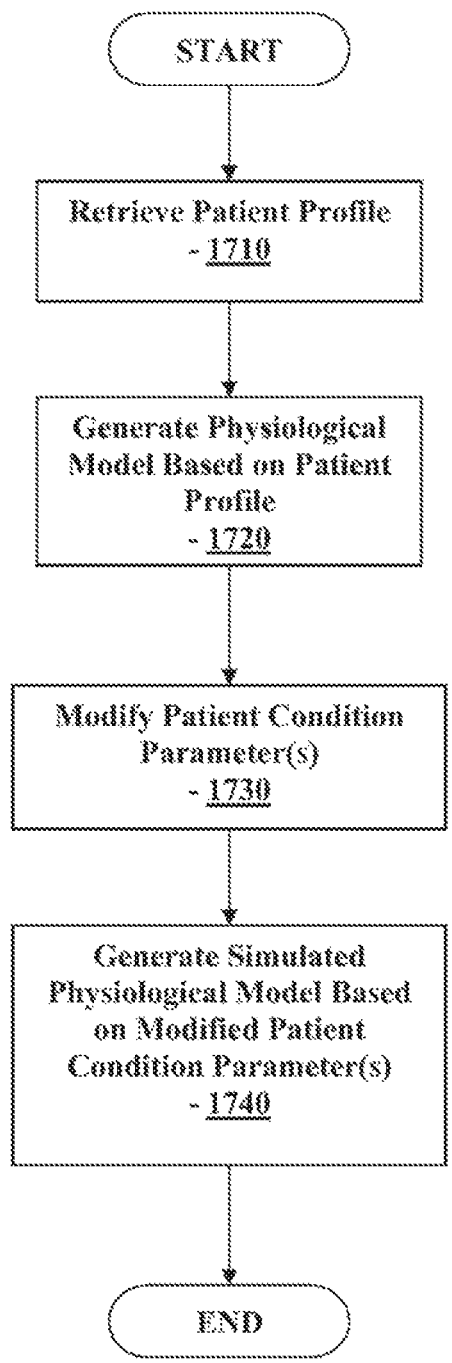
FIG. 17 is a flowchart illustrating dynamic physiological profile simulation routine in accordance with one embodiment of the present disclosure.

FIG. 17 is a flowchart illustrating a dynamic physiological profile simulation routine in accordance with one embodiment of the present disclosure. Referring to FIG. 17, in one aspect of the present disclosure, the physiological profile of a patient or user based on data collected or received from one or more of the analyte monitoring system 110 (FIG. 1) or the fluid delivery device (120) for example, are retrieved (1710). For example, based on a collection of data associated with monitored analyte levels of a patient and/or the therapy information such as the actual or programmed insulin delivery profiles, the profile of a patient which represents the physiological condition of the patient is retrieved. Other relevant data could be collected, for example, but not limited to, the patient's physical activities, meal consumption information including the particular content of the consumed meal, medication intake including programmed and executed basal and/or bolus profiles, other medication ingested during the relevant time period of interest.

Thereafter, a simulation of a physiological model based on the retrieved physiological condition is generated (1720). In one aspect, the generated physiological model includes one or more parameters associated with the patient's physiological condition including, for example, insulin sensitivity, carbohydrate ratio and basal insulin needs. In one aspect, the relevant time period of interest for physiological simulation may be selected by the patient, physician or the care provider as may be desired. In one aspect, there may be a threshold time period which is necessary to generate the physiological model, and thus a selection of a time period shorter than the threshold time period may not result in accurate physiological modeling. For example, in one aspect, the data processing system or device may be configured to establish a seven day period as the minimum number of days based on which, the physiological modeling may be achieved.

Referring to FIG. 17, with the generated physiological model based on the patient's profile, one or more patient condition parameters may be modified (1730). For example, the basal profile for the infusion device of the patient may be modified and entered into the simulation module. Alternatively or in addition, the patient's profile may be modified. For example, the type or amount of food to be ingested may be provided into the simulation module. Within the scope of the present disclosure, the patient, the physician or the care provider may modify one or more of the condition parameters to determine the simulated effect of the modified condition parameter or profile component to the physiological model generated. More specifically, referring back to FIG. 17, when one or more patient condition parameters or one or more profile components is modified, the simulated physiological model is modified or altered in response to the modified condition parameter(s) (1740).

That is, in one aspect, the simulation of the initial physiological profile of a patient may be generated based on collected/monitored data. Thereafter, one or more parameters may be modified to show the resulting effect of such modified one or more patient condition parameters on the simulation of the patient's physiological model. In this manner, in one aspect, the patient, physician or the healthcare provider may be provided with a simulation tool to assist in the therapy management of the patient, where a model based on the patient's condition is first built, and thereafter, with adjustment or modification of one or more parameters, the simulation model provides the resulting effect of the adjustment or modification so as to allow the patient, physician or the healthcare provider to take appropriate actions to improve the therapy management of the patient's physiological condition.

Figure 18:
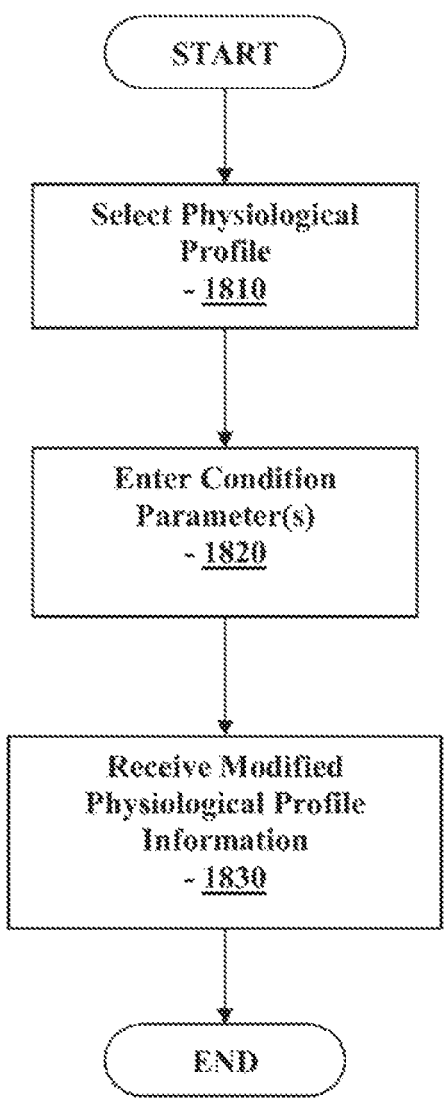
FIG. 18 is a flowchart illustrating dynamic physiological profile simulation routine in accordance with another embodiment of the present disclosure.

FIG. 18 is a flowchart illustrating dynamic physiological profile simulation routine in accordance with another embodiment of the present disclosure. Referring to FIG. 18, in another embodiment, a user selects, using one or more user input devices of a personal computer or other computing or data processing device, the desired physiological profile (1810), and thereafter, one or more condition parameters displayed to the user may be selected as desired. For example, the user may be prompted to select an insulin level adjustment setting, to view a simulation of the physiological profile model responding to such insulin level adjustment setting.

In another aspect, the user may select an activity adjustment setting to view the effect of the selected activity on the physiological profile model. For example, the user may select to exercise for 30 minutes before dinner every day. With this adjustment to the condition parameter, the physiological profile model simulation module may be configured to modify the generated physiological model to show the resulting effect of the exercise on the glucose level of the patient in view of the existing insulin delivery profile, for example. In this manner, one or more parameters associated with the patient's physiological condition may be modified as a condition parameter and provided to the model simulation module to determine the resulting effect of such modified condition parameter (1820). Indeed, referring back to FIG. 18, with the entered condition parameter(s) selected by the patient, physician or the healthcare provider, the simulation module in one aspect may be configured to generate a modified physiological profile model which is received or output to the user, patient, physician or the healthcare provider, visually, graphically, in text form, or one or more combinations thereof (1830).

Figure 19:
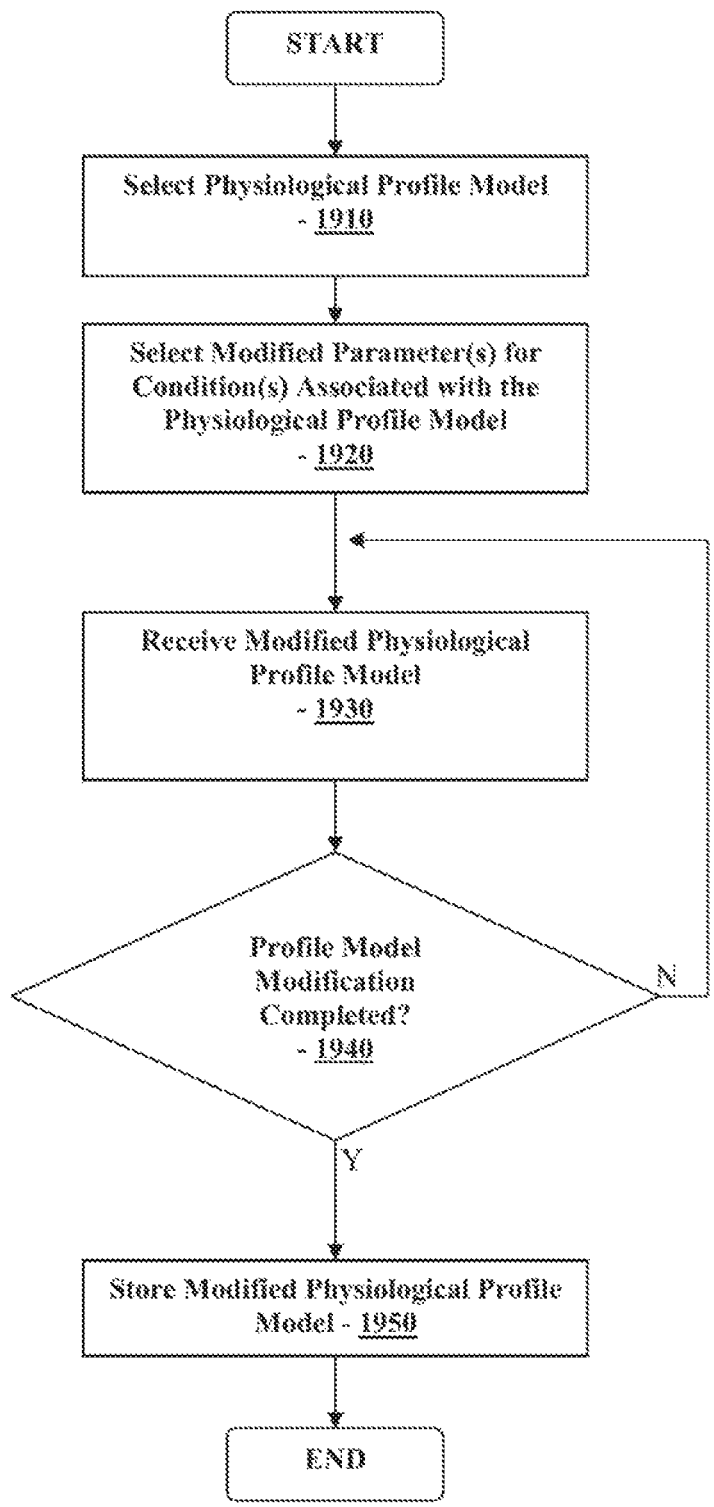
FIG. 19 is a flowchart illustrating dynamic physiological profile simulation routine in accordance with still another embodiment of the present disclosure.

FIG. 19 is a flowchart illustrating dynamic physiological profile simulation routine in accordance with still another embodiment of the present disclosure. Referring to FIG. 19, in one aspect, when the physiological profile model is selected (1910) and the desired modified parameter(s) is selected for the condition(s) associated with the physiological profile model (1920), a modified physiological model is received (1930) or output to the user on a display device of the data processing terminal or computer. Thereafter, the simulation module may prompt the patient, the user, physician or the healthcare provider to either enter additional or different condition parameters to view the resulting effect on the simulated physiological model, or alternatively, select the option to indicate the completion of the modification to the condition parameters (1940).

In this manner, an iteration may be provided such that the patient, user, physician or the healthcare provider may modify one or more conditions associated with the patient's physiological condition, and in response, view or receive in real time, the resulting effect of the modified one or more conditions to the modeled physiological condition simulation. Thereafter, optionally, the modified as well as the initial physiological profile model (and including any intermediate modification to the physiological profile model based on one or more parameter inputs) may be stored in the memory or storage unit of the data processing terminal or computer (1950).

In this manner, in one aspect, when the simulation module has sufficient data associated with the patient's physiological condition or state to define the simulation model parameters, the patient, healthcare provider, physician or the user may model different treatment scenarios to determine strategies for managing the patient's condition such as the diabetic condition in an interactive manner, for example. Thus, changes to the resulting physiological model may be displayed or provided to the patient, physician or the healthcare provider based on one or more potential changes to the treatment regimen.

Figure 20:
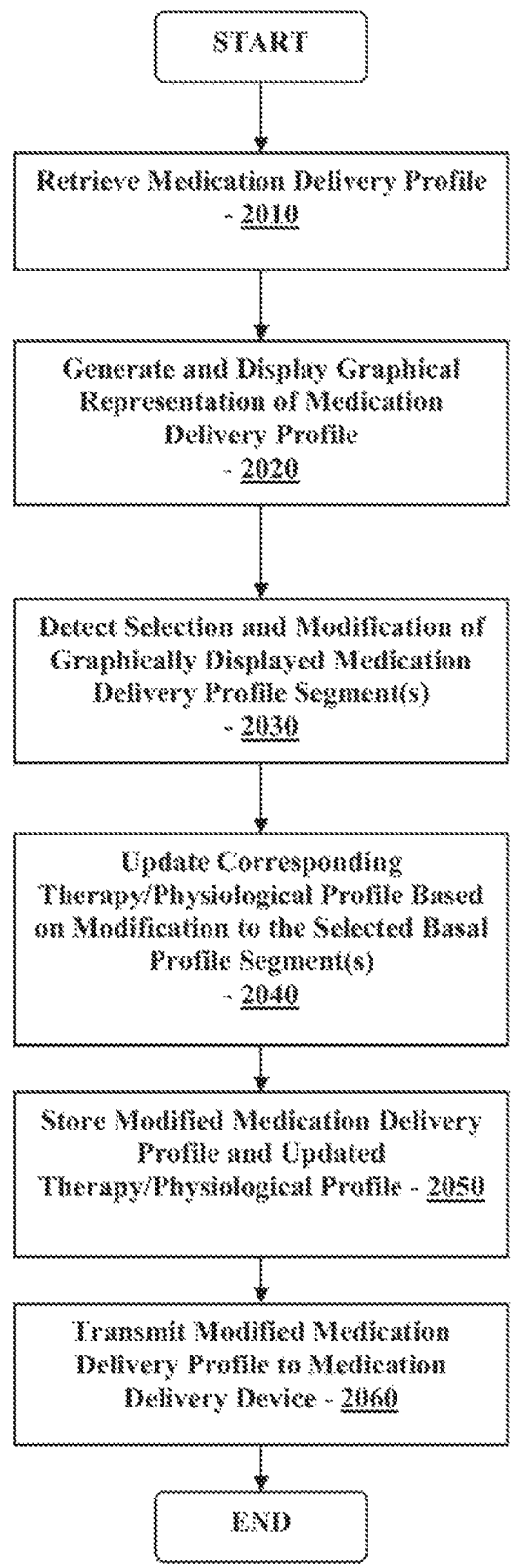
FIG. 20 is a flowchart illustrating visual medication delivery profile programming in accordance with one embodiment of the present disclosure.

FIG. 20 is a flowchart illustrating visual medication delivery profile programming in accordance with one embodiment of the present disclosure. Referring to FIG. 20, medication delivery profile such as a basal rate profile is retrieved (2010), for example, from memory of the remote terminal 140 (FIG. 1) or received from the fluid delivery device 120 (FIG. 1) such as an insulin pump. Thereafter, a graphical representation of the medication delivery profile is generated and displayed (2020) on the display unit of the remote terminal 140. For example, the graphical representation of the medication delivery profile may include a line graph of the insulin level over a predetermined time period for the corresponding medication delivery profile.

In one aspect, the graphically displayed medication delivery profile may be configured to be manipulated using an input device for the remote terminal 140 such as, for example, a computer mouse, a pen type pointing device, or any other types of user input device that is configured for manipulation of the displayed objects on the display unit of the remote terminal 140. In addition to the graphical display of the medication delivery profile, one or more of a corresponding therapy or physiological profile for a particular patient or user may be displayed. For example, in one embodiment, based on data received from the analyte monitoring system 110 and/or the fluid delivery device 120, the remote terminal 140 may be configured to display the basal profile programmed in the fluid delivery device 120 indicating the amount of insulin that has been programmed to administer to the patient, and the corresponding monitored analyte level of the patient, insulin sensitivity, insulin to carbohydrate ratio, and any other therapy or physiological related parameters.

Referring to FIG. 20, the patient or the user including a physician or the healthcare provider may manipulate the user input device such as the computer mouse coupled to the remote terminal 140 to select and modify one or more segments of the graphically displayed medication delivery profile (2030). In response to the display manipulation/modification, the corresponding displayed therapy/physiological profile may be dynamically updated (2040). For example, using one or more of the user input devices, the user or the patient may select a portion or segment of the basal profile line graph, and either move the selected portion or segment of the line graph in vertical or horizontal direction (or at an angle), to correspondingly modify the level of the medication segment for a given time period as graphically displayed by the line graph.

In one aspect, the medication delivery profile in one aspect may be displayed as a line graph with time of day represented along the X-axis and the value or level of the medication on the Y-axis. When the computer mouse is moved near a segment of the line graph, the cursor displayed on the remote terminal 140 display unit may be configured to change to indicate that the portion of the line graph may be selected and dragged on the displayed screen. For example, the horizontal portions of the line graph may be dragged in a vertical direction to increase or decrease the setting or the medication level for that selected time period, while the vertical portions of the line graph may be dragged in the horizontal direction to adjust the time associated with the particular medication level selected.

Referring again to FIG. 20, in one aspect, the modified medication delivery profile and the updated therapy/physiological profile are stored (2050) in a storage unit such as a memory of the remote terminal 140, and thereafter, may be transmitted to one or more of the fluid delivery device 120 or the analyte monitoring system 110 (2060). In this manner, in one aspect, the patient or the user may be provided with an intuitive and graphical therapy management tool which allows manipulation of one or more parameters associated with the patient's condition such as diabetes, and receive real time visual feedback based on the manipulation of the one or more parameters to determine the appropriate therapy regimen.

For example, when the user or the patient wishes to maintain his or her blood glucose level within a predetermined range, the user may manipulate the line graph associated with the insulin delivery rate, for example, to receive feedback on the effect of the change to the insulin amount on the blood glucose level. The modeling of the physiological parameters associated with the patient in one aspect may be generated using computer algorithms that provide simulated model of the patient's physiological condition based on the monitored physiological condition, medication delivery rate, patient specific conditions such as exercise and meal events (and the types of exercise and meal for the particular times), which may be stored and later retrieved for constructing or modeling the patient's physiological conditions.

Figure 21:
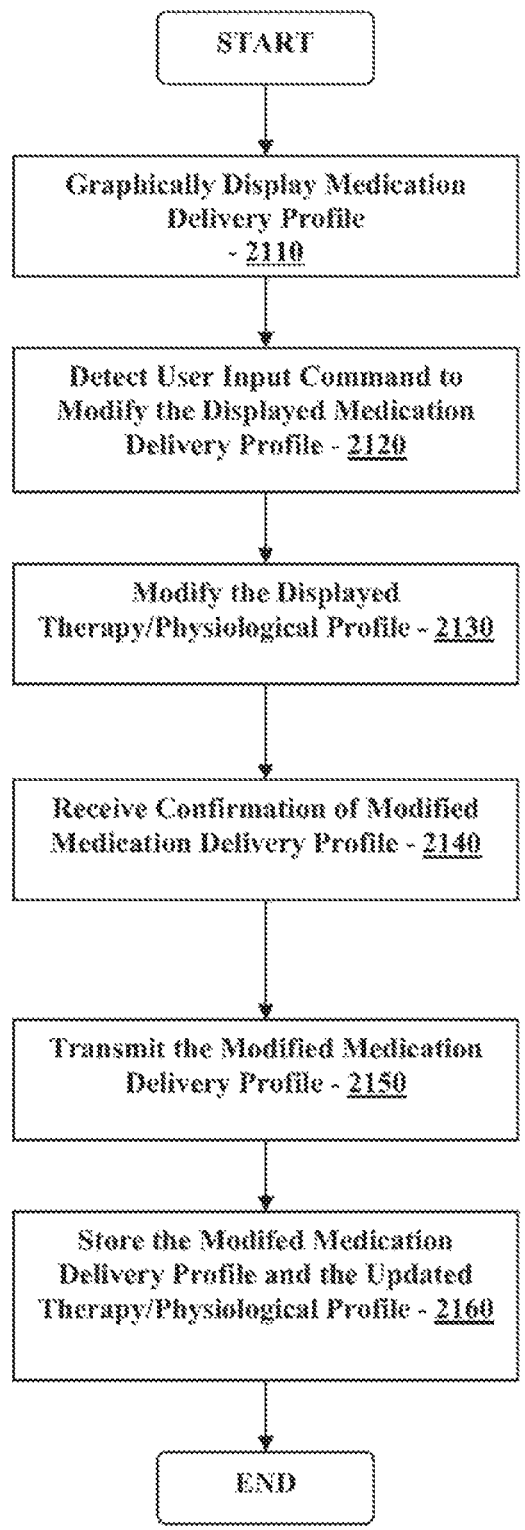
FIG. 21 is a flowchart illustrating visual medication delivery profile programming in accordance with another embodiment of the present disclosure.

FIG. 21 is a flowchart illustrating visual medication delivery profile programming in accordance with another embodiment of the present disclosure. Referring to FIG. 21, medication delivery profile for a particular patient may be graphically displayed (2110), and thereafter, upon detection of an input command to modify the displayed medication delivery profile (2120), the corresponding displayed therapy physiological profile is modified (2130). As discussed above, the input command may be received from an input device such as a computer mouse executing select and drag functions, for example, on the display screen of the remote terminal 140. In one aspect, in response to the input command, the displayed medication delivery profile as well as the corresponding displayed therapy/physiological profile may be graphically updated to provide visual feedback to the patient or the user of the effect resulting from the input command modifying the medication delivery profile.

Referring to FIG. 21, when the confirmation of the modified medication delivery profile is received (2140), for example, via the user input device, the modified medication delivery profile may be transmitted (2150) and, the modified medication delivery profile and the updated therapy/physiological profile are stored (2160). That is, when the user or the patient confirms or accepts the modification or update to the medication delivery profile based, for example, on the visual feedback received corresponding to the change to the therapy/physiological profile, in one aspect, the modified medication delivery profile may be transmitted to the fluid delivery device 120 to program the device for execution, for example. The transmission may be wireless using RF communication, infrared communication or any other suitable wireless communication techniques, or alternatively, may include cabled connection using, for example, USB or serial connection.

In this manner, in one aspect, there is provided an intuitive and easy to use visual feedback mechanism to improve treatment of a medical condition such as diabetes, by providing visual modeling of the therapy regimen that can be dynamically adjusted to show the effect of such adjustment to the physiological condition.

Figure 22:
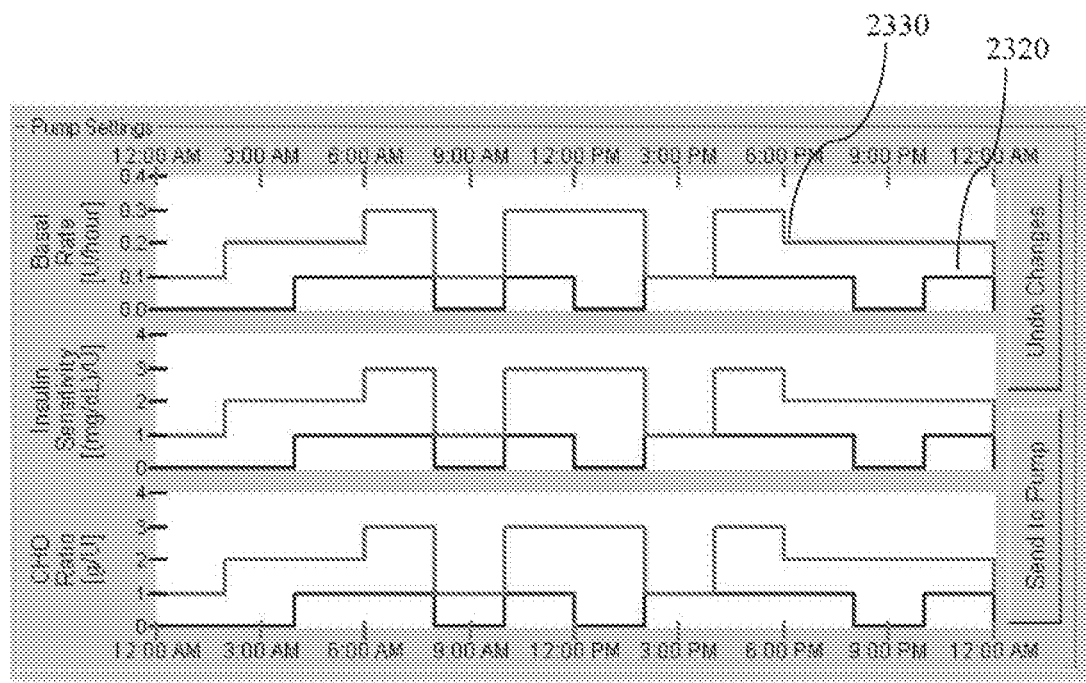
FIG. 22 is an exemplary screen display of a medication delivery profile.
Figure 23:
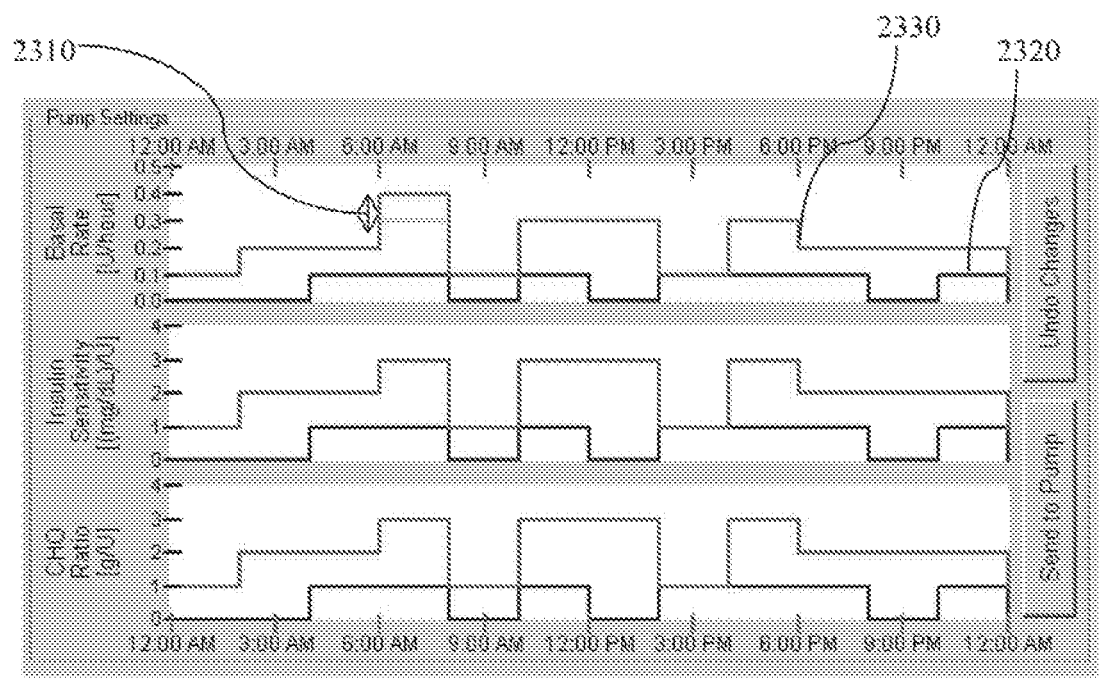
FIG. 23 is an exemplary screen display illustrating vertical modification of the medication delivery profile.
Figure 24:
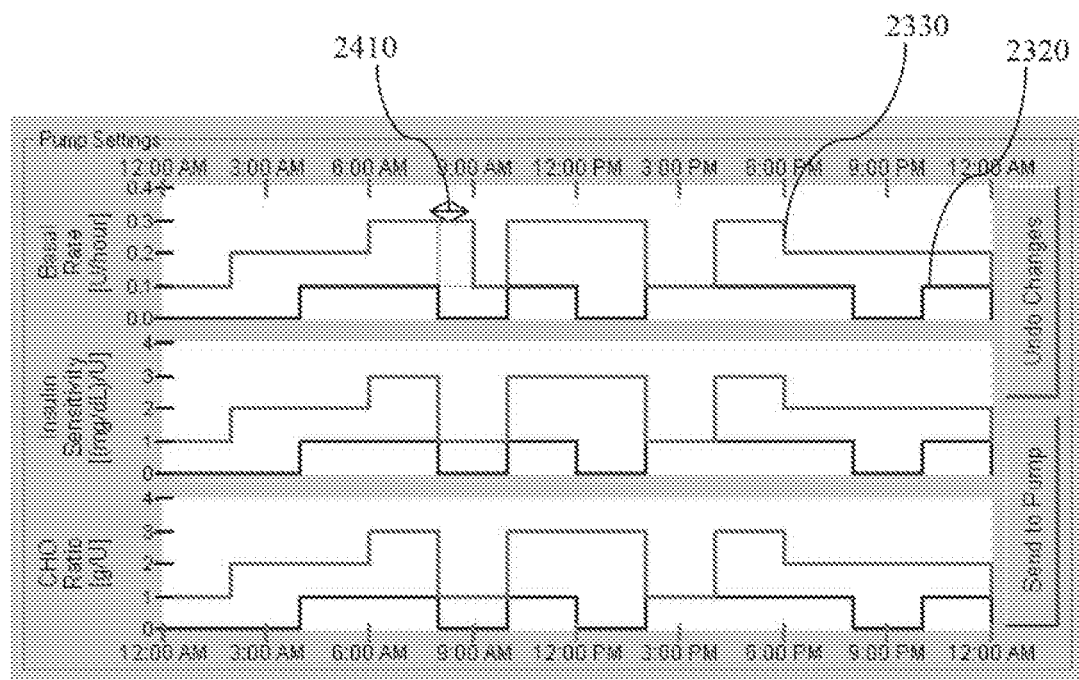
FIG. 24 is an exemplary screen display illustrating horizontal modification of the medication delivery profile.
Figure 25:
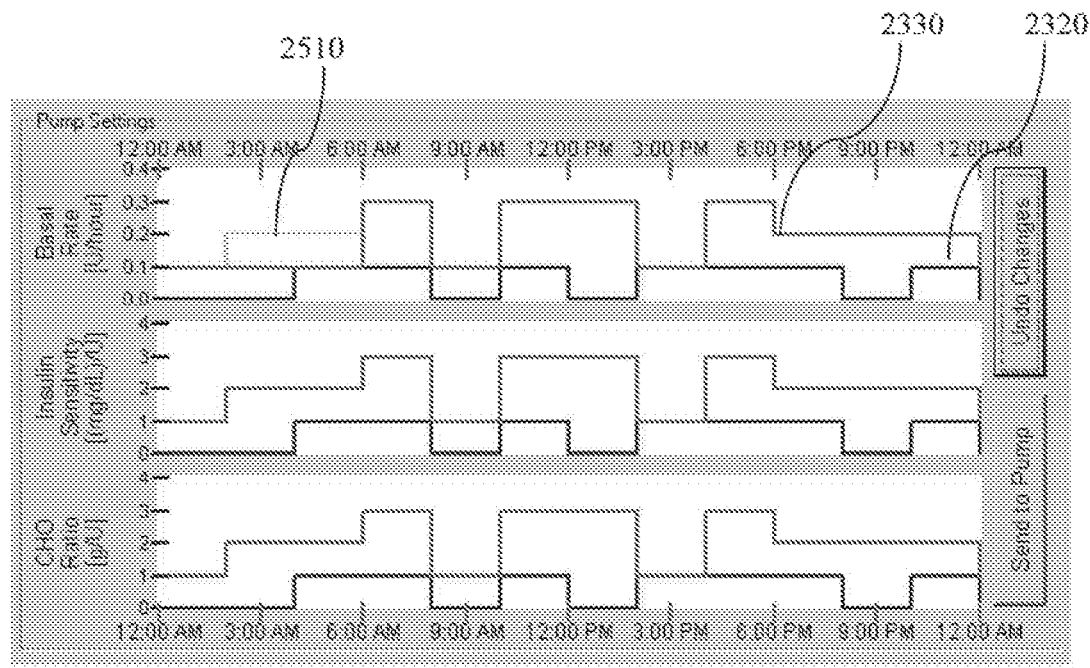
FIG. 25 is an exemplary screen display illustrating addition of a transition in the medication delivery profile.
Figure 26:
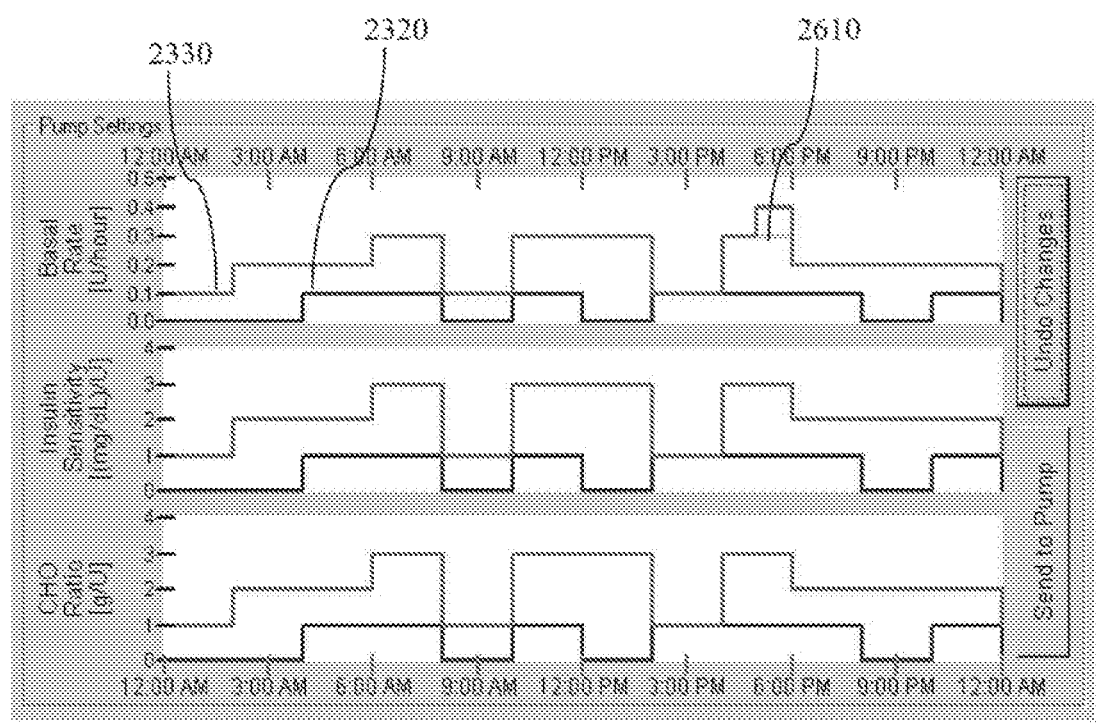
FIG. 26 is an exemplary screen display illustrating deletion of a transition in the medication delivery profile.

FIG. 22 is an exemplary screen display of a medication delivery profile. As can be seen, in one aspect, the basal rate, insulin sensitivity and the insulin to carbohydrate ratio (CHO) are shown on the Y-axis, while the X-axis represents the corresponding time of day. For each of these therapy parameters, the existing profile is shown 2320 and the optimal profile proposed by the therapy calculator is shown 2330. FIG. 23 is an exemplary screen display illustrating vertical modification of the proposed medication delivery profile as shown by the directional arrow 2310, while FIG. 24 illustrates an exemplary screen display with horizontal modification of the proposed medication delivery profile shown by the directional arrow 2410. Referring still to the Figures, FIG. 25 illustrates addition of a transition 2510 in the medication delivery profile, while FIG. 26 illustrates deletion 2610 of a transition in the medication delivery profile.

In this manner, in one aspect, the visual modeling and dynamic feedback in therapy management provides immediate feedback on the anticipated results or effect of a proposed modification to the therapy profile such as increase or decrease of insulin administration to the patient. Accordingly, the patient, the physician or the healthcare provider may be provided with a graphical treatment tool to assist in the treatment of the patient's condition.

In another aspect, the visual modeling and dynamic feedback in the therapy management includes illustration of a current physiological profile such as the glucose level and one or more time corresponding parameter values associated with the current physiological profile such that, when the user, patient or healthcare provider modifies the displayed one or more parameter values (such as, but not limited to, the corresponding medication level including basal profile, insulin sensitivity, and/or insulin to carbohydrate ratio), the corresponding current physiological profile is responsively modified and displayed in real time, while leaving a trace (referred to herein as a phantom plot) of the current physiological profile and the time corresponding one or more parameter values associated with the current physiological profile.

That is, by manipulating the display of the therapy related parameter value to a modified level (for example, using a conventional click and drag operation of an input device such as a computer mouse), the displayed current physiological profile is modified on the screen accordingly, while maintaining the display of the current physiological profile as well as the initial or current therapy related parameter value. In other words, in one aspect, the display or screen is configured to represent both the initial profile and the modified profile so that the user, patient or healthcare provider can readily see the change to the plotted physiological profile in response to the modification to the one or more parameter values, for example, the initial profile or plot shown as a lighter trace (phantom plot) or of a different color or representation, while maintaining a darker color or thickness of the plot for the modified profile/plot.

For example, with a plot of a glucose level information and a corresponding basal profile on the screen, when the user, patient or the healthcare provider selects the basal profile and moves or modifies one or more sections of the basal profile, the initial position of the glucose level remains displayed as a trace (phantom plot), while displaying the new or modified glucose level. In addition, both the initial and the modified basal profile of the time corresponding basal profile are displayed on the same chart or plot. In this manner, in one aspect, the display of the remote terminal 140 (FIG. 1) and/or the display of the analyte monitoring system 110 or the display of the fluid delivery device 120 may be manipulated using, for example, user interface capabilities such as an input device (computer mouse for use with the remote terminal 140), input/select buttons on the analyte monitoring system 110 or the fluid delivery device 120 to provide visual indications of the extent of adjustment to one or more parameters from the initial or recommended settings or profiles and the corresponding modification to the associated physiological or other monitored profile such as glucose levels in addition to the initial displayed profile.

Figure 27:
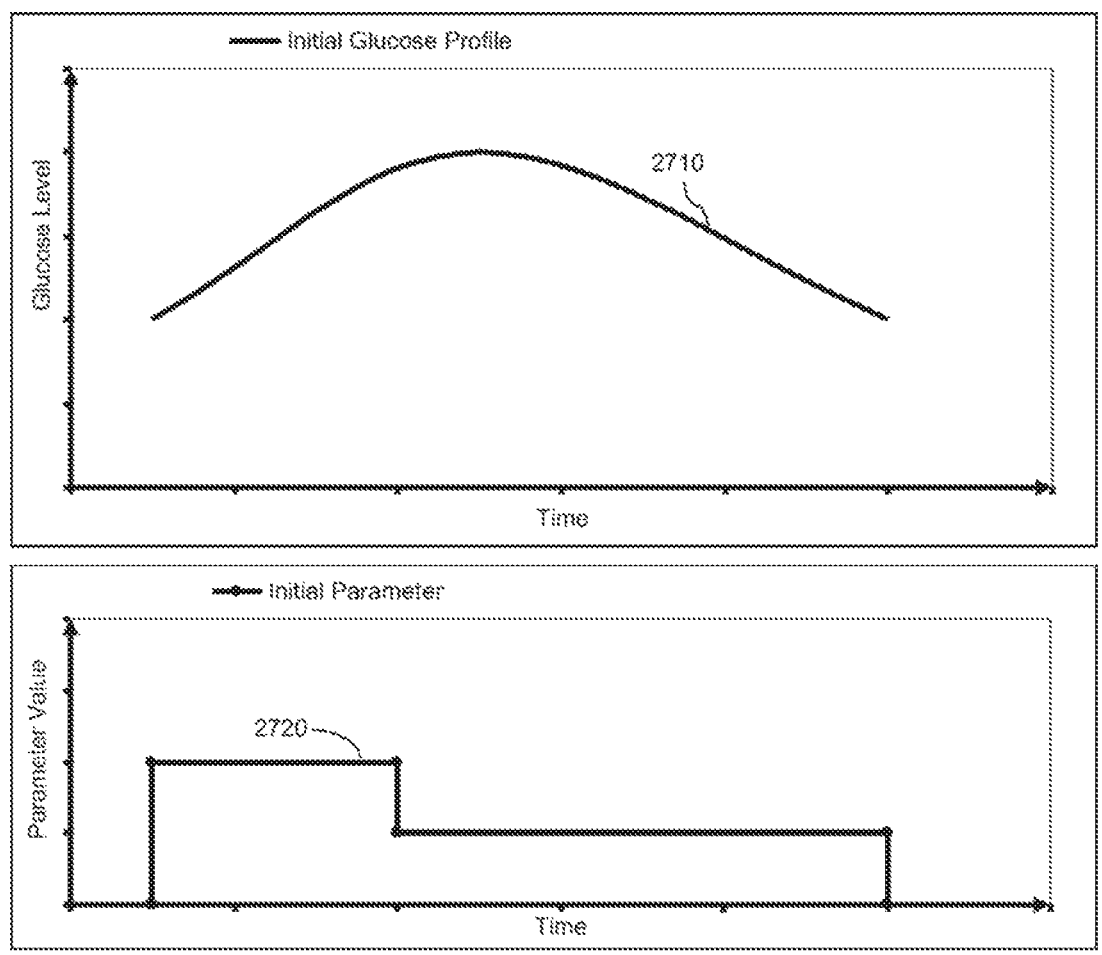
FIG. 27 is an exemplary display illustrating an initial glucose level and a corresponding parameter value as a function of time in one embodiment.
Figure 28:
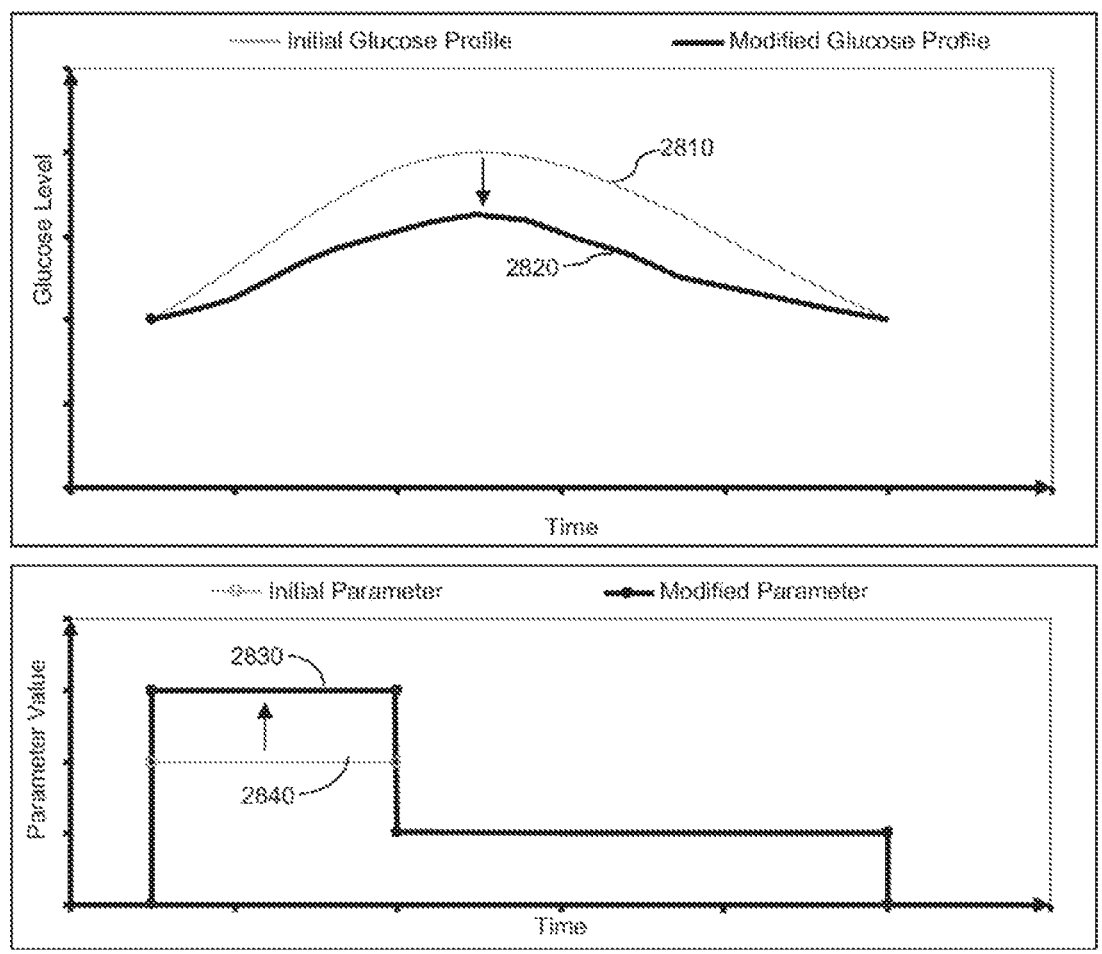
FIG. 28 is an exemplary display illustrating response to the manipulation of the initial parameter value of FIG. 27 and corresponding modification to the displayed glucose profile as a function of time in one embodiment.
Figure 29:
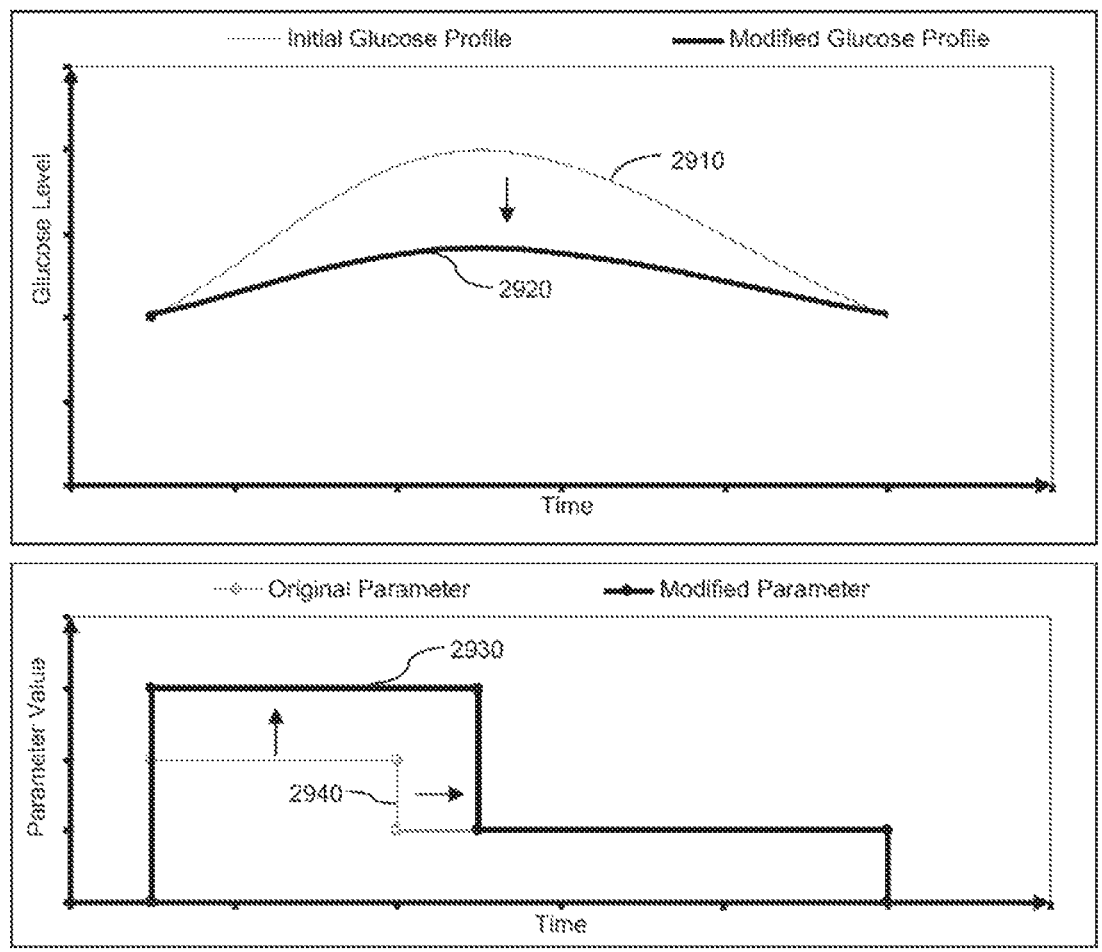
FIG. 29 is an exemplary display illustrating response to the manipulation of the initial parameter value of FIG. 27 and corresponding modification to the displayed glucose profile as a function of time in another embodiment.

FIG. 27 is an exemplary display illustrating an initial glucose level and a corresponding parameter value, and FIGS. 28-29 are exemplary displays illustrating response to the manipulation of the parameter plot or value segment of FIG. 27 and corresponding modification to the displayed glucose profile as a function of time in one embodiment. Referring to FIGS. 27-29, an initial display of one parameter value 2720 (FIG. 27) is plotted along with a time corresponding plot of the glucose level 2710 (FIG. 27). In one aspect, the user, patient or the healthcare provider may move the computer mouse to position the cursor over and select a segment of the plotted parameter value 2720 (for example, between two displayed dots at each transition point in the displayed plot). With the selected segment of the plotted parameter, the user, patient or the healthcare provider may move the selected segment in a vertical direction as shown in FIG. 28, in a horizontal direction, or in both a horizontal and vertical direction as shown in FIG. 29.

Referring back to FIG. 28, when the selected segment of the displayed parameter 2840 is moved in an upward vertical direction to a new position 2830 as shown, the corresponding initial glucose profile 2810 is updated to the modified glucose profile 2820. As shown in FIG. 28, it can be seen that both the initial position and the modified position of the parameter plot and those of the glucose levels are shown. In particular, in one embodiment, when a modification to the parameter value is effected, the segment of the initial position or plot of the parameter value (and the corresponding initial display of the glucose level) is displayed as a lighter trace or of a different color (for example, the initial parameter segment 2840 and the initial glucose profile 2810) to be distinguishable with the modified parameter segment 2830 and the corresponding modified glucose profile 2820. In one aspect, the particular type of display modes (different color, thickness, legend indicating the initial and modified chart or profile segment) may be user definable or configurable.

Referring to FIG. 29, when a segment 2940 of the parameter displayed is modified in both the vertical and the horizontal direction to the modified position 2930 as shown, the corresponding displayed initial glucose level display 2910 is updated to a modified profile 2920 in the direction shown by the arrow illustrating a movement from the initial display 2910 to the modified display 2920 in addition to the display of the initial glucose profile 2910 and the initial parameter value 2940.

In this manner, in one aspect, proposed or recommended modification to therapy profiles such as basal profiles may be displayed including the initial and modified profiles, and the corresponding initial and modified physiological profiles recalculated or determined in response to the proposed or recommended modification to the therapy profiles may be visually output to the user, patient or the healthcare provider to enhance visual representation of the proposed or recommended modification to the therapy profiles in the course of the treatment and therapy of physiological conditions such as diabetes. In this manner, the user, patient or the healthcare provider may easily and visually understand the degree of parameter change and effect of the change on the output values such as insulin delivery and glucose level.

While a single parameter plot is shown in conjunction with the discussion above and FIGS. 27-29, in accordance with the embodiments of the present disclosure, multiple parameter values or profiles may be displayed and modified by the user, patient, or the healthcare provider. In such cases, for each parameter displayed, when a modification to the parameter is performed, both the initial and the modified profile or plot may be displayed. Moreover, while glucose level is discussed above in the physiological profile displayed, embodiments of the present disclosure may be used to display other physiological profiles and associated parameters that affect the physiological profile, such as blood pressure level or other physiological conditions.

In accordance with the embodiments of the present disclosure, other variations of the embodiments discussed above are contemplated. For example, the phantom plots may be associated with the plots that are adjusted rather than the plots that stay in the same position. Also, as discussed above, the phantom plots may be represented other than as a thinner line (compared to the non-phantom or the modified profile), including, such as, for example, with different colors, line types, icon indication, legends, labels and the like. In addition, the modification to the initial profile or parameter may be represented in tabular form with numeric value entries, with some table elements associated with the original or initial values and other table elements representing the adjusted/modified values.

In a further embodiment, for multiple adjustments or modifications, the phantom (original) plot may be updated or modified after each adjustment, relative to the immediately prior modification position. In this case, optionally, multiple phantom plots may be displayed (using different indications such as gradually increasing thickness of the plotted line, or different color or legend, for example) such that the modifications may be visually represented in a graphically sweeping manner, illustrating each modification to the parameter(s) and the corresponding modification to the physiological profile in, for example, a single chart or display.

Moreover, other mechanisms may be contemplated to allow the user, patient or the healthcare provider to make the adjustments to the parameters. For example, a table may be provided and displayed with numeric values associated with parameter segments, and the user, patient or the healthcare provider may edit the numeric values in the table. After the adjustment or modification to the numeric value in the table, the corresponding plots may be modified as described above, in a similar manner as when the graphical segment is modified using, for example, the computer mouse by click and drag operation.

In addition, adjustment or modification to the parameters may be performed in other manner. For example, segments of the parameter plots may be predefined, for instance, at a segment of 15 minutes or other time periods. Alternatively, the segments may be defined by changes in time for the original parameter value. Additionally, new segments may be defined by the user using for example, the computer mouse by clicking the mouse button with a cursor near a point on the parameter plot, where the selected or clicked point representing the end of a segment with the beginning of a segment already defined on the plot (as indicated by a dot on the plot). Also, a segment may be defined by the user with a mouse click once near one point on a plot and again near a second point, where the points define a segment. In this aspect, the segment may be visually highlighted (for example, made thicker) to indicate to the user that it can be dragged or otherwise adjusted or modified. Furthermore, these defined segments may be limited to a predefined time resolution as defined by the insulin delivery device, for example. That is, fluid delivery device 120 (FIG. 1) may be limited to a 15 minute resolution of parameter changes, in which case, the plotting routine may locate the 15 minute point on the plot closest to where the user selected with the mouse.

In another aspect, the display discussed above may include one or more error indication. For example, the glucose display may show, along with the median glucose profile, the upper and lower glucose quartiles. This information may be useful to the user when making corresponding adjustments to the therapy profile. For example, if the user, patient or the healthcare provider desires to make parameter adjustments in order to lower the median glucose profile, they may understand from the lower quartile plot that there is a high degree of glucose variation and that it may not be safe or desirable to lower the median profile as much as they intended or desired. In one aspect, the phantom plots discussed above may be associated with these types of displayed error indications.

As described above, the profile modification and the corresponding displays may be based on data organized around time-of-day information. In another aspect, the modifications or determinations and the corresponding display plots may be based on meal markers or meal bolus events recorded in time. These events may be entered into the system manually (for instance a meal event may be entered into the system by the user) or automatically (the system may record a meal bolus when it is delivered, using, for example, the fluid delivery device 120). The parameter, insulin delivery and glucose data may be organized in data sets, with time relative to the meal bolus event. A resulting data set for each may be generated using a median calculation or average calculation, or other appropriate calculation, to generate a profile in time relative to the meal bolus event. For example, each data set may be defined one hour prior to and 5 hours after when meals bolus event occurs. Adjustments, as described above for plots over time-of-day, may be made similarly for plots over time-relative-to-meal-events. Also, determination and display of parameters, insulin delivery and glucose profiles may be made for data sets generated relative to correction bolus events.

In one aspect, the user may select from a list of possible parameters to adjust or modify based on one or more indications presenting the parameters available for modification. For example, if the basal parameter adjustment is selected, then the determination or modification and display may be associated with time-of-day. In this case, when the user adjusts the glucose values, the basal profile parameter may be adjusted to correlate with glucose level adjustments. As a further example, if the carbohydrate ratio parameter is selected, the modification and display may be associated with time relative to meal bolus or meal events. As yet a further example, when the insulin sensitivity parameter adjustment is selected, the modification and display may be associated with time relative to a correction bolus.

Additionally, when modifications and displays are associated with time relative to an event, they may be restricted to time of day periods. For example, the profile modification determination may be restricted to one or more meal bolus that occurs in a morning period, for instance, between 6 am and 11 am. This restriction may be used to associate a single carbohydrate ratio parameter for this time period. Also, the resulting modified parameters may be constrained by resolution restrictions imposed by the insulin delivery device 120 discussed above.

In an alternative embodiment, the parameter and/or physiological profile display may include both actual and recommended glucose traces, insulin traces and therapy parameter traces, in addition to the modified traces, and further, may be user definable or configurable.

Within the scope of the present disclosure, data mining techniques may be used to generate and/or modify the physiological profile models based on the patient's data as well as data from other patients that have similar physiological characteristics. Such data mining techniques may be used to filter and extract physiological profile models that meet a predetermined number of criteria and ranked in a hierarchy of relevance or applicability to the particular patient's physiological condition. The simulation module may be implemented by computer software with algorithm that defines the parameters associated with the patient's physiological conditions, and may be configured to model the various different conditions of the patient's physiology.

Within the scope of the present disclosure, the therapy analysis system described above may be implemented in a database management system and used for treatment of diabetic patients by a general practitioner. Additionally, the therapy analysis system may be implemented based on multiple daily doses of insulin (using, for example, syringe type insulin injector, or inhalable insulin dispenser) rather than based on an insulin pump, where the insulin related information may be recorded by the patient and uploaded or transferred to the data management system (for example, the remote terminal 140 (FIG. 1)). Also, some or all of the data analysis and display described above may be performed by the analyte monitoring system 110 (FIG. 1) or the fluid delivery device 120, or by a separate controller configured for communication with the therapy management system 100.

In one embodiment, a method may comprise displaying a first representation of a medication treatment parameter profile, displaying a first representation of a physiological profile associated with the medication treatment parameter profile, detecting a modification to a segment of the medication treatment parameter profile, displaying a modified representation of the medication treatment parameter profile and the physiological profile based on the detected modification to the segment of the medication treatment parameter profile, modifying an attribute of the first representation of the medication treatment parameter profile, and modifying an attribute of the first representation of the physiological profile.

In one aspect modifying the attribute of the first representation of the medication treatment parameter profile may include modifying a visual attribute without modifying the underlying value associated with the profile.

Moreover, the visual attribute may include one or more of a color representation, a line representation, visual contrast representation.

In another aspect, the modified representation and the first representation of the medication treatment parameter profile may include at least an overlapping displayed segment.

In yet another aspect the modified representation and the first representation of the physiological profile may be substantially non-overlapping.

In one aspect, the medication treatment parameter profile may include one or more of a basal rate profile, an insulin sensitivity profile, an insulin to carbohydrate ratio, a meal event, a bolus event, or an insulin type profile.

In another aspect, the physiological profile may include a glucose level profile, an oxygen level profile, or a blood pressure level profile.

In yet another aspect, modifying the attribute of the first representation of the physiological profile may include modifying a visual attribute without modifying the underlying value associated with the profile.

Moreover, when the attribute of the first representation of the medication treatment parameter profile is modified, the displayed position of the first representation of the medication treatment parameter profile is not changed.

Moreover, when the attribute of the first representation of the physiological profile is modified, the displayed position of the first representation of the physiological profile is not changed.

Furthermore, the displayed first representation of the medication treatment parameter profile and the physiological profile respectively may include one or more of a line graph, a bar graph, a 2-dimensional graph, or a 3-dimensional graph.

In another embodiment, an apparatus may comprise, a display unit, one or more processing units coupled to the display unit, and a memory for storing instructions which, when executed by the one or more processing units, may cause the one or more processing units to display a first representation of a medication treatment parameter profile, display a first representation of a physiological profile associated with the medication treatment parameter profile, detect a modification to a segment of the medication treatment parameter profile, display a modified representation of the medication treatment parameter profile and the physiological profile based on the detected modification to the segment of the medication treatment parameter profile, modify an attribute of the first representation of the medication treatment parameter profile, and modify an attribute of the first representation of the physiological profile.

In one aspect, the memory for storing instructions which, when executed by the one or more processing units, may cause the one or more processing units to modify a visual attribute associated with the physiological profile without modifying the underlying value associated with the first representation of the physiological profile, and to modify a visual attribute associated with the first representation of the medication treatment parameter profile without modifying the underlying value associated with the medication treatment parameter profile.

Moreover, the visual attribute may include one or more of a color representation, a line representation, visual contrast representation.

In another aspect, the modified representation and the first representation of the medication treatment parameter profile may include at least an overlapping displayed segment.

Furthermore, the modified representation and the first representation of the physiological profile may be substantially non-overlapping.

In yet another aspect, the medication treatment parameter profile may include one or more of a basal rate profile, an insulin sensitivity profile, an insulin to carbohydrate ratio, a meal event, a bolus event, or an insulin type profile.

Moreover, the physiological profile may include a glucose level profile, an oxygen level profile, or a blood pressure level profile.

In yet another aspect, when the attribute of the first representation of the medication treatment parameter profile is modified, the displayed position of the first representation of the medication treatment parameter profile may not be changed, and further, when the attribute of the first representation of the physiological profile is modified, the displayed position of the first representation of the physiological profile may not be changed.

The various processes described above including the processes performed by the processor 210 (FIG. 2) in the software application execution environment in the fluid delivery device 120 (FIG. 1) as well as any other suitable or similar processing units embodied in the analyte monitoring system 110, the fluid delivery device 120, and/or the remote terminal 140, including the processes and routines described in conjunction with FIGS. 3-16, may be embodied as computer programs developed using an object oriented language that allows the modeling of complex systems with modular objects to create abstractions that are representative of real world, physical objects and their interrelationships. The software required to carry out the inventive process, which may be stored in the memory unit 240 (or similar storage devices in the analyte monitoring system 110 and the remote terminal 140) and executed by the processor 210, may be developed by a person of ordinary skill in the art and may include one or more computer program products.

Various other modifications and alterations in the structure and method of operation of this disclosure will be apparent to those skilled in the art without departing from the scope and spirit of the disclosure. Although the present disclosure has been described in connection with specific preferred embodiments, it should be understood that the present disclosure as claimed should not be unduly limited to such specific embodiments. It is intended that the following claims define the scope of the present disclosure and that structures and methods within the scope of these claims and their equivalents be covered thereby.

What is claimed is:
1. A system comprising:
   a data receiver configured to receive, over a communication link, information corresponding to a detected glucose level of a user from an analyte sensor;
   an insulin infusion device communicatively coupled with the data receiver and configured to deliver insulin to the user's body;
   one or more processors communicatively coupled with the data receiver and the insulin infusion device, at least one of the one or more processors programmed to control the delivery of insulin from the insulin infusion device based on the information corresponding to the detected glucose level of the user and a modified glucose level;
   a display unit communicatively coupled to the one or more processors and a memory, wherein the memory stores instructions that, when executed by the one or more processors, causes the one or more processors to simultaneously display on the display unit:
      a first representation of an insulin treatment parameter profile comprising a vertical basal insulin axis and a first trace line of basal insulin over a horizontal time scale represented by at least one time axis;
      a modified representation of the insulin treatment parameter profile comprising the vertical basal insulin axis and a second trace line of basal insulin over the horizontal time scale based on a detected horizontal and/or vertical user modification to the first trace line of basal insulin;
      a first representation of a physiological profile associated with the insulin treatment parameter profile comprising a vertical glucose parameter axis and a first trace line of a glucose parameter over the horizontal time scale; and
      a modified representation of the physiological profile comprising the vertical glucose parameter axis and a second trace line of the glucose parameter over the horizontal time scale based on a determined corresponding modification to the glucose parameter due to the detected user modification to the first trace line of basal insulin, wherein the second trace line of the glucose parameter comprises the modified glucose level.

2. The system of claim 1, further comprising an infusion tube and an infusion cannula, the infusion tube coupled with the insulin infusion device.

3. The system of claim 1, further comprising a data transmitter configured to transmit the information corresponding to the detected glucose level from the analyte sensor and to the data receiver over the communication link.

4. The system of claim 3, wherein the data transmitter is configured to transmit the information corresponding to the detected glucose level of the user over the Bluetooth communication link substantially in real time.

5. The system of claim 4, wherein the data transmitter is configured to transmit information corresponding to a plurality of detected glucose levels substantially in real time over a predefined time period, and wherein the one or more processors are further programmed to control the delivery of insulin from the insulin infusion device based on a rate of change of the detected glucose levels over the predefined time period.

6. The system of claim 3, wherein the communication link is a Bluetooth communication link.

7. The system of claim 1, wherein the memory further stores instructions that, when executed by the one or more processors, causes the one or more processors to modify a visual attribute associated with the physiological profile without modifying an underlying value associated with the first representation of the physiological profile, and to modify a visual attribute associated with the first representation of the insulin treatment parameter profile without modifying the underlying value associated with the insulin treatment parameter profile.

8. The system of claim 1, wherein the memory further stores instructions which, when executed by the one or more processors, causes the one or more processors to display one or more boundaries associated with the physiological profile.

9. The system of claim 8, wherein the memory further stores instructions which, when executed by the one or more processors, causes the one or more processors to output an error indication when the modified representation of the physiological profile exceeds the one or more boundaries.

10. The system of claim 1, wherein the memory further stores instructions which, when executed by the one or more processors, causes the one or more processors to monitor data related to the physiological profile based on a rate of change of the physiological profile, and determine trend data based on the rate of change of the physiological profile.

11. The system of claim 1, wherein the glucose parameter of the physiological profile includes at least one of a median glucose profile, an upper quartile glucose profile, and a lower quartile glucose profile.

12. The system of claim 1, wherein the glucose parameter of the physiological profile includes a median glucose profile, an upper quartile glucose profile, and a lower quartile glucose profile.

13. The system of claim 1, wherein the horizontal time scale is represented by a first time axis in the first representation of the insulin treatment parameter profile, and wherein the horizontal time scale is represented by a second time axis in the first representation of the physiological profile.

14. A system comprising:
   a data receiver configured to receive, over a communication link, information corresponding to a detected analyte level of a user from an analyte sensor;
   a medication delivery device communicatively coupled with the data receiver and configured to deliver medication to the user's body;

one or more processors communicatively coupled with the data receiver and the medication delivery device, at least one of the one or more processors programmed to control the delivery of the medication from the medication delivery device based on the information corresponding to the detected analyte level of the user and a modified analyte level;

a display unit communicatively coupled to the one or more processors and a memory, wherein the memory stores instructions that, when executed by the one or more processors, causes the one or more processors to simultaneously display on the display unit:

a first medication treatment parameter profile trace line comprising a medication axis over a time scale, the time scale represented by at least one time axis;

a modified second medication treatment parameter profile trace line comprising the medication axis over the time scale, the modified second medication treatment parameter profile based on a detected user modification to the first medication treatment parameter profile trace line;

a first physiological profile trace line associated with the medication treatment parameter profile, the first physiological profile trace line comprising a physiological profile axis over the time scale; and a modified second physiological profile trace line comprising the physiological profile axis over the time scale, the modified second physiological profile trace based on a determined corresponding modification to the medication treatment parameter profiled due to the detected user modification to the first medication treatment parameter profile trace line.

15. The system of claim 14, wherein the medication treatment parameter profile is selected from the group consisting of a basal insulin rate profile, an insulin sensitivity profile, an insulin to carbohydrate ratio, a meal event, or a bolus insulin event.

16. The system of claim 14, wherein the physiological profile is selected from the group consisting of a glucose level profile, an oxygen level profile, or a blood pressure level profile.

17. The system of claim 14, further comprising a data transmitter configured to transmit the information corresponding to the detected glucose level from the analyte sensor and to the data receiver over the communication link.

18. The system of claim 14, wherein the communication link is a Bluetooth communication link.

19. A system comprising:

a display unit;

one or more processors and a memory communicatively coupled to the display unit, wherein the memory stores instructions that, when executed by the one or more processors, causes the one or more processors to simultaneously display on the display unit:

a first medication treatment parameter profile trace line comprising a medication axis over a time scale, the time scale represented by at least one time axis;

a modified second medication treatment parameter profile trace line comprising the medication axis over the time scale, the modified second medication treatment parameter profile based on a detected user modification to the first medication treatment parameter profile trace line;

a first physiological profile trace line associated with the medication treatment parameter profile, the first physiological profile trace line comprising a physiological profile axis over the time scale; and a modified second physiological profile trace line comprising the physiological profile axis over the time scale, the modified second physiological profile trace based on a determined corresponding modification to the medication treatment parameter profiled due to the detected user modification to the first medication treatment parameter profile trace line.

20. The system of claim 19, wherein the modified second physiological profile trace comprises a modified analyte level, and further comprising a medication delivery device communicatively coupled with a data receiver and configured to deliver medication to a user's body based on information corresponding to a detected analyte level of the user from an analyte sensor and the modified analyte level.

* * * * *